(12) United States Patent
Watanabe et al.

(10) Patent No.: US 11,096,957 B2
(45) Date of Patent: Aug. 24, 2021

(54) HIGH MOLECULAR WEIGHT GLUCAN HAVING LOW DIGESTION RATE

(71) Applicant: EZAKI GLICO, CO., LTD., Osaka (JP)

(72) Inventors: Hiroshi Watanabe, Osaka (JP); Yoshinobu Terada, Osaka (JP)

(73) Assignee: EZAKI GLICO CO., LTD., Osaka (JP)

( * ) Notice: Subject to any disclaimer, the term of this patent is extended or adjusted under 35 U.S.C. 154(b) by 220 days.

(21) Appl. No.: 16/473,168

(22) PCT Filed: Dec. 22, 2017

(86) PCT No.: PCT/JP2017/046224
§ 371 (c)(1),
(2) Date: Feb. 13, 2020

(87) PCT Pub. No.: WO2018/123901
PCT Pub. Date: Jul. 5, 2018

(65) Prior Publication Data
US 2020/0206259 A1    Jul. 2, 2020

(30) Foreign Application Priority Data
Dec. 27, 2016 (JP) .............................. JP2016-253555

(51) Int. Cl.
*C12P 19/18* (2006.01)
*A61K 31/718* (2006.01)
(Continued)

(52) U.S. Cl.
CPC .............. *A61K 31/718* (2013.01); *A23L 2/52* (2013.01); *A23L 33/10* (2016.08); *A23L 33/125* (2016.08);
(Continued)

(58) Field of Classification Search
None
See application file for complete search history.

(56) References Cited

U.S. PATENT DOCUMENTS 5,827,697 A    10/1998  Takaha et al.
6,248,566 B1    6/2001  Imanaka et al.
(Continued)

FOREIGN PATENT DOCUMENTS

EP    0 710 674 A3    6/1996
EP    1 943 908 A1    7/2008
(Continued)

OTHER PUBLICATIONS

English Translation of International Search Report and Written Opinion, dated Mar. 20, 2018, for International Application No. PCT/JP2017/046224, 2 pages.
(Continued)

*Primary Examiner* — Eric Olson
(74) *Attorney, Agent, or Firm* — Seed Intellectual Property Law Group LLP

(57) ABSTRACT

One purpose of the present invention is to provide a high molecular weight glucan having both properties low digestion rate and high digestibility. A high molecular weight glucan that has property digested slowly and contains almost no indigestible ingredients is produced by enzymatic reactions of (1) a specific concentration of branching enzyme and (2) 4-α-glucanotransferase and/or an exo-type amylase to a branched glucan used as a substrate.

14 Claims, 7 Drawing Sheets

(51) Int. Cl.
*A23L 33/125* (2016.01)
*A61P 3/10* (2006.01)
*A23L 2/52* (2006.01)
*A61K 9/00* (2006.01)
*C08B 30/18* (2006.01)
*C12P 19/04* (2006.01)
*C12P 19/20* (2006.01)
*C12P 19/22* (2006.01)
*C08B 30/20* (2006.01)
*A23L 33/10* (2016.01)

(52) U.S. Cl.
CPC ............... *A61K 9/0053* (2013.01); *A61P 3/10* (2018.01); *C08B 30/18* (2013.01); *C08B 30/20* (2013.01); *C12P 19/04* (2013.01); *C12P 19/18* (2013.01); *C12P 19/20* (2013.01); *C12P 19/22* (2013.01); *A23V 2002/00* (2013.01)

(56) References Cited

U.S. PATENT DOCUMENTS

| | | | |
|---|---|---|---|
| 9,562,247 | B2 | 2/2017 | Takaha et al. |
| 10,149,809 | B2 | 12/2018 | Sambe et al. |
| 10,543,159 | B2 | 1/2020 | Kobayashi |
| 2003/0215562 | A1 | 11/2003 | Shi et al. |
| 2004/0115778 | A1 | 6/2004 | Fujii et al. |
| 2010/0099864 | A1 | 4/2010 | van der Maarel et al. |
| 2011/0020496 | A1 | 1/2011 | Shimada et al. |
| 2013/0295163 | A1 | 11/2013 | Takaha et al. |
| 2013/0302405 | A1 | 11/2013 | Takaha et al. |

FOREIGN PATENT DOCUMENTS

| | | |
|---|---|---|
| EP | 2 248 907 A1 | 11/2010 |
| JP | 8-134104 A | 5/1996 |
| JP | 11-236401 A | 8/1999 |
| JP | 2001-11101 A | 1/2001 |
| JP | 2004-131682 A | 4/2004 |
| JP | 2009-524439 A | 7/2009 |
| JP | 2010-514443 A | 5/2010 |
| JP | 2012-120471 A | 6/2012 |
| JP | 2015-109868 A | 6/2015 |
| WO | 2007/088676 A1 | 9/2007 |
| WO | 2008/085529 A2 | 7/2008 |

OTHER PUBLICATIONS

Kasprzak et al., "Effect of Enzymatic Treatment of Different Starch Sources on the in Vitro Rate and Extent of Starch Digestion," *International Journal of Molecular Sciences* 13:929-942, 2012.

Kittisuban et al., "Slow glucose release property of enzyme-synthesized highly branched maltodextrins differs among starch sources," *Carbohydrate Polymers* 107:182-191, 2014.

Lee et al., "Enzyme-Synthesized Highly Branched Maltodextrins Have Slow Glucose Generation at the Mucosal α-Glucosidase Level and Are Slowly Digestible In Vivo," *PLOS One* 8(4):e59745, 2013. (10 pages).

Shimada et al., "Enzymatically Produced Maltodextrin with Different Linkage Mode and Its Effect on Blood Glucose Elevation," *The Japanese Society of Applied Glycoscience* 61:45-51, 2014.

Shin et al., "Slowly Digestible Starch from Debranched Waxy Sorghum Starch: Preparation and Properties," *Cereal Chemistry* 81(3):404-408, 2004.

Sorndech et al., "Structure of branching enzyme- and amylomaltase modified starch produced from well-defined amylose to amylopectin substrates," *Carbohydrate Polymers* 152:51-61, 2016.

Sorndech et al., "Synergistic amylomaltase and branching enzyme catalysis to suppress cassava starch digestibility," *Carbohydrate Polymers* 132:409-418, 2015.

Zhang et al., "Slowly Digestible Starch: Concept, Mechanism, and Proposed Extended Glycemic Index," *Critical Reviews in Food Science and Nutrition* 49:852-866, 2009.

Kaur et al., "Progress in starch modification in the last decade," *Food Hydrocolloids* 26:398-404, 2012.

Analysis result of enzymatically hydrolyzed product of working example 1-3

Analysis result of enzymatically hydrolyzed product of working example 1-6

Standard
(Peaks: (from left) glucose, maltose, maltotriose, maltotetraose, maltopentaose, maltohexaose, maltoheptaose)

Rise in blood glucose after glucose ingestion

Rise in blood insulin level after glucose ingestion

Rise in blood glucose level after glucose ingestion

Rise in blood insulin level after glucose ingestion

HIGH MOLECULAR WEIGHT GLUCAN HAVING LOW DIGESTION RATE

BACKGROUND

Technical Field

The present invention relates to a high molecular weight glucan that achieves both properties of low digestion rate and high digestibility. The present invention further relates to a method for producing the high molecular weight glucan and to products using the high molecular weight glucan.

Description of the Related Art

Carbohydrates are an essential nutrient as an energy source, typical examples of which include starches. Use of native starches as the raw material of processed foods, however, may raise some issues, for example, low processability due to insolubility in water, and poor storage stability due to retorogradation. To address these issues, high molecular weight glucan partially hydrolyzed in acid or enzyme, generally called dextrin, has so far been developed. While the dextrin is improved in properties including treatability and storage stability, its digestion rate is fast, which leads to spikes in blood glucose level and/or in blood insulin level after the dextrin ingestion. Such rapid raise in blood glucose level and/or blood insulin level after ingestion are considered to be a cause of obesity and/or diabetes. Under the circumstances, there are ongoing attempts to modify the chemical structure of dextrin through chemical and/or enzymatic reactions in order to slow down the rate of digestion (Non-Patent Document 1).

Among the methods that have been developed and reported to enzymatically modify the dextrin's structure in order to slow down digestion are; enhancement of the dextrin's crystallinity to make digestive enzymes poorly reactive (Patent Document 1, Non-Patent Document 2), increase of the ratio of α-1,6-glucoside bonds included in dextrin (Patent Documents 3 and 5, Non-Patent Document 3), and increase of any other bonds but α-1,6-glucoside bonds, i.e., α-1,2-glucoside bonds and α-1,3-glucoside bonds (Patent Document 6). All of these methods are, however, which attempt to adequately slow down the digestion rate of dextrin (slower than native glycogens) may result to increase the ratio of indigestible (indigestible structure) moieties and sacrifice structural moieties that can be used as energy sources.

Some reports say that certain considerations on types and amounts of enzymes to be used may lead to successful synthesis of dextrin slow to digest and containing less indigestible moiety (Patent Document 2, Non-Patent Document 4). In order to lower the rate of digestion, however, such dextrin includes α-1,3-glucoside bonds which are not digested by any human digestive enzymes, and at least any part of its structure including such bonds is not usable as energy source. Another issue to be addressed with these types of dextrin is their lowering the molecular weight as a result of exhaustive enzymatic reactions to make digestion rate slower. This may invite the risks of higher osmotic pressure in solutions used and elevated reducing sugar levels. The osmotic pressure is desirably lower, because drinks with high osmotic pressure are likely to cause diarrhea and abdominal distension. Large amount of reducing sugar may cause discoloration during storage of products.

Thus, a high molecular weight glucan having the properties of low digestion rate and high digestibility may be valuable in terms of physiological functionality and treatability. Yet, such a glucan is, in fact, virtually unknown to this date.

PRIOR ART DOCUMENTS

Non-Patent Documents

Non-Patent Document 1: Critical Reviews in Food Science and Nutrition 49, 852-867 (2009)
Non-Patent Document 2: Cereal Chemistry 81, 404-408 (2004)
Non-Patent Document 3: Carbohydrate Polymers 132, 409-418 (2015)
Non-Patent Document 4: Journal of Applied Glycoscience 61, 45-51 (2014)

PATENT DOCUMENTS

Patent Document 1: Japanese Patent Laid-open Publication No. 2004-131682
Patent Document 2: Japanese Patent Laid-open Publication No. 2015-109868
Patent Document 3: Japanese Patent Laid-open Publication No. 2001-11101
Patent Document 4: Japanese Patent Laid-open Publication No. 2009-524439
Patent Document 5: Japanese Patent Laid-open Publication No. 2012-120471
Patent Document 6: Japanese Patent Laid-open Publication No. H11-236401

BRIEF SUMMARY

Problems to be Solved by the Invention

An object of the present invention is to provide a high molecular weight glucan that achieves both properties of low digestion rate and high digestibility. Another object of the present invention is to provide products using the high molecular weight glucan.

Means for Solving the Problem

The present inventors were committed to finding solutions to the issues described above, and they conducted various researches, studies, and tests for the purpose. The inventors were then led to the finding that a high molecular weight glucan slow to digest, containing substantially no indigestible component, and achieving both properties of low digestion rate and high digestibility may be obtained by making (1) a branching enzyme having a certain concentration, and (2) 4-α-glucanotransferase and/or exo-type amylase react with a branched glucan which is used as substrate, selected from, for example, starches, amylopectin, glycogen, dextrin, enzymatically synthesized branched glucan, and highly-branched cyclic glucan.

Other findings in regard to structural features of the high molecular weight glucan are; branched chains of α-1,6-glucoside bonds are linked to main chains of α-1,4-glucoside bonds, and the high molecular weight glucan has an average molecular weight of 10,000 to 500,000 and the following properties (i) to (iii) are fulfilled by an HPAEC-PAD analysis result of a unit chain length distribution obtained after the α-1,6-glucoside bonds are hydrolyzed by isoamylase, (i) the ratio of the total value of the peak areas for degrees of polymerization of 1 to 5 to the total value of the peak areas for degrees of polymerization of 6 to 10 (($DP_{1-5}/DP_{6-10}$)×100) is 33% to 50%.

(ii) the ratio of the total value of the peak areas for degrees of polymerization of 11 to 15 to the total value of the peak areas for degrees of polymerization of 6 to 10 (($DP_{11-15}/DP_{6-10}$)×100) is 80% to 125%.

(iii) the ratio of the total value of the peak areas for degrees of polymerization of 26 to 30 to the total value of the peak areas for degrees of polymerization of 6 to 10 (($DP_{26-30}/DP_{6-10}$)×100) is 16% to 43%.

The present invention was finally accomplished through further studies and discussions based on these findings. The present invention described herein provides the following technical aspects.

Technical Aspect 1

High molecular weight glucan having a structure in which a branched chain is linked by α-1,6-glucoside bond to a main chain of α-1,4-glucoside bond, and further characterized in that the high molecular weight glucan has an average molecular weight of 10,000 to 500,000 and satisfies the following properties. The following properties i) to iii) are based on HPAEC-PAD analysis result of a unit chain length distribution obtained after the α-1,6-glucoside bond is hydrolyzed by isoamylase and decomposed into a linear unit chain length, (i) the ratio of the total value of the peak areas for degrees of polymerization of 1 to 5 to the total value of the peak areas for degrees of polymerization of 6 to 10 (($DP_{1-5}/DP_{6-10}$)×100) is 33% to 50%, (ii) the ratio of the total value of the peak areas for degrees of polymerization of 11 to 15 to the total value of the peak areas for degrees of polymerization of 6 to 10 (($DP_{11-15}/DP_{6-10}$)×100) is 80% to 125%, and (iii) the ratio of the total value of the peak areas for degrees of polymerization of 26 to 30 to the total value of the peak areas for degrees of polymerization of 6 to 10 (($DP_{26-30}/DP_{6-10}$)×100) is 16% to 43%.

Technical Aspect 2

The high molecular weight glucan according to the technical aspect 1, wherein at least one of the following properties iv) to vii) is further fulfilled by an analysis result of the unit chain length distribution, (iv) the ratio of the total value of the peak areas for degrees of polymerization of 16 to 20 to the total value of the peak areas for degrees of polymerization of 6 to 10 (($DP_{16-20}/DP_{6-10}$)×100) is 53% to 85%, (v) the ratio of the total value of the peak areas for degrees of polymerization of 21 to 25 to the total value of the peak areas for degrees of polymerization of 6 to 10 (($DP_{21-25}/DP_{6-10}$)×100) is 31% to 62%, (vi) the ratio of the total value of the peak areas for degrees of polymerization of 31 to 35 to the total value of the peak areas for degrees of polymerization of 6 to 10 (($DP_{31-35}/DP_{6-10}$)×100) is 8% to 30%, and (vii) the ratio of the total value of the peak areas for degrees of polymerization of 36 to 40 to the total value of the peak areas for degrees of polymerization of 6 to 10 (($DP_{36-40}/DP_{6-10}$)×100) is 3% to 21%.

Technical Aspect 3

The high molecular weight glucan as described in the technical aspect 1 or 2, wherein an initial digestion rate coefficient k calculated in the following in vitro digestibility test is less than 0.029, and the ratio of indigestible components in 120 minutes after start of the enzyme reaction is less than 10%;

How to Perform In Vitro Digestibility Test a mixture of 100 μL of a 5 w/v % high molecular weight glucan aqueous solution, 20 μL of a 1M acetic acid buffer (pH 5.5) and 716 μL of distilled water is prepared, and further 4 μL of a porcine pancreatic α-amylase solution and 160 μL of a 250 U/mL rat small intestine acetone powder solution equivalent to 0.3 U/mL α-glucosidase activity are added to the mixture, and then start the digestive reaction at 37° C. The concentration of free glucose hydrolyzed from high molecular weight glucan during the reaction is measured over time. The initial digestion rate coefficient k is calculated by the following formula, $$\ln(1-C_t)=-kt, \quad \text{Formula 1:}$$

where t is reaction time (min.), $C_t$ is (amount of glucose produced until reaction time t is reached)/(total amount of glucose in high molecular weight glucan), and the initial digestion rate coefficient k is calculated from slope of a primary regression line on plotted time t and $\ln(1-C_t)$ in 30 minutes since reaction time=0 minute.

Technical Aspect 4

The high molecular weight glucan according to any one of the technical aspects 1 to 3, wherein, in the in vitro digestibility test described above, the ratio of the high molecular weight glucan hydrolyzed within 20 minutes from the start of the enzyme reaction is less than 45%, and the ratio of the high molecular weight glucan hydrolyzed from 20 minutes to 120 minutes after the start of the enzyme reaction is greater than or equal to 50%.

Technical Aspect 5

The high molecular weight glucan according to any one of the technical aspects 1 to 4, wherein a non-reducing end of the main chain of the α-1,4-glucoside bond does not have a branching structure formed by the α-1,6-glucoside bond.

Technical Aspect 6

A food and/or a drink comprising the high molecular weight glucan according to any one of the technical aspects 1 to 5.

Technical Aspect 7

The food and/or the drink according to the technical aspect 6 for use in control of rise in blood glucose level and/or in blood insulin level.

Technical Aspect 8

An infusion including the high molecular weight glucan according to any one of the technical aspects 1 to 5.

Technical Aspect 9

A pharmaceutical product including the high molecular weight glucan according to any one of the technical aspects 1 to 5.

Technical Aspect 10

A method for producing the high molecular weight glucan according to any one of the technical aspects 1 to 5, the method comprising:

making 100 to 4,000 U/g substrate of branching enzyme and 4-α-glucanotransferase react to a branched glucan used as substrate at the same time or stepwisely in any order; and terminating the reactions at a point in time after the high molecular weight glucan according to any one of the technical aspects 1 to 5 is produced.

Technical Aspect 11

A method for producing the high molecular weight glucan according to any one of the technical aspects 1 to 5, the method comprising:

making 100 to 4,000 U/g substrate of a branching enzyme react with a branched glucan which is used as substrate, and then making an exo-type amylase react with the branched glucan which is used as substrate; and terminating the reactions at a point in time after the high molecular weight glucan according to any one of the technical aspects 1 to 5 is produced.

Technical Aspect 12

The production method as described in the technical aspect 10 and further characterized in that the 4-α-glucanotransferase is amylomaltase and/or cyclodextrin glucanotransferase.

Technical Aspect 13

The method according to the technical aspect 11, wherein the exo-type amylase is β-amylase.

Technical Aspect 14

The method according to the technical aspects 10 to 13, wherein the branched glucan is waxy starch.

Technical Aspect 15

Use of the high molecular weight glucan according to any one of the technical aspects 1 to 4 for the production of an agent for use in controlling a rise in blood glucose level and/or in blood insulin level.

Technical Aspect 16

A method for controlling a rise in blood glucose level and/or in blood insulin level, comprising administration of the high molecular weight glucan according to any one of the technical aspects 1 to 4 to a human subject who needs to control a rise in his/her blood glucose level and/or blood insulin level.

Advantages of the Invention

The high molecular weight glucan according to the present invention thus having a specific unit chain length distribution may achieve a lower rate of digestion. This high molecular weight glucan, when ingested, is slowly digested in the body, and may prevent spikes in blood glucose level and/or blood insulin level. The high molecular weight glucan according to the present invention includes substantially no indigestible component and may accordingly achieve high digestibility. This high molecular weight glucan, therefore, may be useful as an efficient source of energy. Such a high molecular weight glucan that achieves both properties of low digestion rate and high digestibility, which has not so far been reported, may be a prospective alternative for the known branched glucans (for example, starches, dextrin) in fields and applications associated with foods, drinks, and medical products.

DETAILED DESCRIPTION

1. Definition

Figure 1:
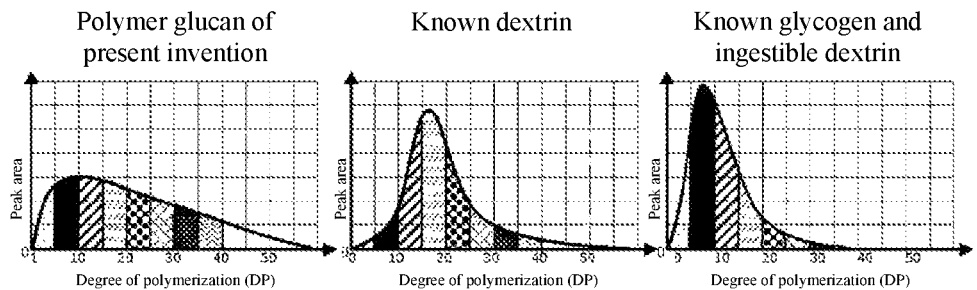
FIG. 1 presents model diagrams that respectively illustrate unit chain length distributions of high molecular weight glucan according to the present invention, and a dextrin, a glycogen, and an indigestible dextrin of the known art.

In this description, "low digestion rate" means that the high molecular weight glucan is slowly digested after being orally ingested. This may specifically mean that, in the high molecular weight glucan, its initial digestion rate coefficient k is less than 0.029 in the in vitro digestibility test described later.

In this description, "high digestibility" means that the high molecular weight glucan includes less or substantially no indigestible component, and includes more components usable as energy after orally ingestion. For example, the in vitro digestibility test described later finds that, the high molecular weight glucan has less than 10% of components which are not degraded to glucose in 120 minute of hydrolysis reaction by digestive enzyme.

In this description, one unit (1U) of isoamylase, α-amylase, glucoamylase, or α-glucosidase indicates the following enzyme amounts.

Isoamylase 1U: enzyme amount that produces 1 μmol of reducing sugar in 1 minute from oyster-derived glycogen, α-amylase 1U: enzyme amount that produces 1 mg of maltose in 3 minutes from soluble starch, Glucoamylase 1U: enzyme amount that produces 10 mg of glucose in 30 minutes from soluble starch, α-glucosidase 1U: enzyme amount that liberates 1 μmol of 4-nitrophenol in 1 minute from p-nitrophenyl-α-D-glucopyranoside.

In this description, "rat small intestine acetone powder" refers to a crude enzyme preparation in the form of powder containing α-glucosidase, which is obtained as follows; acetone is added to a homogenate of rat small intestine, the acetone-added homogenate is then cooled, and a precipitate is collected from this mixture and then dried.

2. High Molecular Weight Glucan

The present invention provides high molecular weight glucan characterized in that a branched chain is linked by α-1,6-glucoside bond to a main chain of α-1,4-glucoside bond. Further, this high molecular weight glucan has an average molecular weight of 10,000 to 500,000, and exhibits a specific unit chain length distribution when the α-1,6-glucoside bond is hydrolyzed by isoamylase and decomposed into a linear unit chain length. The high molecular weight glucan according to the present invention is hereinafter described in detail.

2-1. Linking Modes of D-Glucose

The high molecular weight glucan according to the present invention is a branched α-1,4-glucan with α-1,6-glucoside bonds.

In the high molecular weight glucan according to the present invention, the branch frequency by the α-1,6-glucoside bonds is not particularly limited insofar as a unit chain length distribution described later is fulfilled. For example, the branch frequency may be greater than or equal to approximately 7%, preferably greater than or equal to approximately 7.5%, or more preferably greater than or equal to approximately 8%. The upper limit of the branch frequency is also not particularly limited insofar as the unit chain length distribution described later is fulfilled. For example, the branch frequency may be less than or equal to approximately 11%, preferably less than or equal to approximately 10.5%, or more preferably less than or equal to approximately 10%. Specifically, the branch frequency in the high molecular weight glucan according to the present invention may range from approximately 7 to approximately 11%, preferably range from approximately 7.5 to approximately 10.5%, or more preferably range from approximately 8 to approximately 10%.

According to the present invention, the branch frequency by the α-1,6-glucoside bonds may be a value calculated by the following formula.

Branch frequency (%) caused by α-1,6-glucoside bond={number of α-1,6-glucoside bonds/total glucose unit number in molecule}×100  Formula 2:

In the high molecular weight glucan according to the present invention, the branched chains by the α-1,6-glucoside bonds may be either evenly or unevenly distributed relative to the main chains.

A suitable linking mode in the high molecular weight glucan of the present invention is distinct in that a non-reducing end of the main chain of the α-1,4-glucoside bond does not have a branching structure formed by the α-1,6-glucoside bond.

2-2. Average Molecular Weight and Average Degree of Polymerization

The average molecular weight of the high molecular weight glucan according to the present invention is 10,000 to 500,000. According to one aspect of the high molecular weight glucan described herein, the average molecular weight may preferably be greater than or equal to approximately 50,000, or may more preferably be greater than or equal to approximately 100,000. According to one aspect of the high molecular weight glucan described herein, the average molecular weight may preferably be less than or equal to approximately 300,000, or may more preferably be less than or equal to approximately 200,000. According to a preferred aspect of the high molecular weight glucan of the present invention, the average molecular weight may preferably be approximately 50,000 to approximately 300,000, or may more preferably be approximately 100,000 to approximately 200,000. Any increase in osmotic pressure may be suppressed in drinks containing the high molecular weight glucan having an average molecular weight within these numerical ranges. Further advantageously, the increase of reducing sugar level may be controlled in various products in which this high molecular weight glucan is used.

The average molecular weight of the high molecular weight glucan according to the present invention refers to a weight-average molecular weight measured by the GPC-MALS method. Specific conditions for measurement of the average molecular weight of the high molecular weight glucan will be given later in the description of working examples.

The average degree of polymerization of the high molecular weight glucan according to the present invention is not particularly limited insofar as the average molecular weight stays within the before-mentioned numerical ranges. For example, the average degree of polymerization may be greater than or equal to approximately 60, preferably greater than or equal to approximately 80, more preferably greater than or equal to approximately 100, or even more preferably greater than or equal to approximately 120. The upper-limit average degree of polymerization of the high molecular weight glucan according to the present invention is also not particularly limited insofar as the average molecular weight stays within the before-mentioned numerical ranges. For example, the degree of polymerization may be less than or equal to approximately $3.5 \times 10^3$, preferably less than or equal to approximately $3 \times 10^3$, more preferably less than or equal to approximately $2.5 \times 10^3$, or even more preferably less than or equal to approximately $2 \times 10^3$. Specifically, the average degree of polymerization of the high molecular weight glucan according to the present invention may be, for example, approximately 60 to approximately $3.5 \times 10^3$, preferably approximately 80 to approximately $3 \times 10^3$, more preferably approximately 100 to approximately $2.5 \times 10^3$, or even more preferably approximately 120 to $2 \times 10^3$.

In the present invention, the average degree of polymerization of the high molecular weight glucan is a weight-average molecular weight measured by the GPC-MALS method and divided by 162; value calculated by subtracting the molecular weight of water molecules from the molecular weight of glucose. The average degree of polymerization of the substrate used is also measured in a similar manner, which will be described later.

2-3. Unit Chain Length Distribution

Branched α-1,4-glucan having α-1,6-glucoside bonds such as starches, when acted upon by a suitable enzyme like isoamylase, allows the α-1,6-glucoside bonds alone to be completely hydrolyzed and can be thoroughly converted into linear α-1,4-glucan. The linear α-1,4-glucan obtained after decomposition of the branched α-1,4-glucan is called as unit chain of the branched α-1,4-glucan, and its degree of polymerization is called as unit chain length. The unit chains obtained from the branched α-1,4-glucan have variously different degrees of polymerization, and a concentration distribution of the unit chain lengths for different degrees of polymerization (unit chain length distribution) is obtained by the HPAEC-PAD method and the like.

FIG. 1 presents model diagrams that respectively illustrate unit chain length distributions of the high molecular weight glucan according to the present invention, dextrin, glycogen, and indigestible dextrin of the known art. As illustrated in FIG. 1, the unit chain length distribution of the high molecular weight glucan according to the present invention, as compared with the unit chain length distribution of the known dextrin, exhibits peaks representing higher concentrations in a region of shorter chain lengths (degrees of polymerization of approximately 5 to 15). The unit chain length distribution of the high molecular weight glucan according to the present invention is further distinct from the known dextrin, glycogen, and indigestible dextrin in that its distribution is gently curved on the whole, with no prominent peak, and exhibits peaks representing higher concentrations in a region of shorter chain lengths with degrees of polymerization of 10 or less and in a region of longer chain lengths with degrees of polymerization of 25 or more. Thus, one advantageous feature of the high molecular weight glucan according to the present invention is its unique unit chain length distribution. Though the inventors have no intention of the present invention being narrowly interpreted, such a unique unit chain length distribution may be considered to allow the high molecular weight glucan described herein to have a good balance between two desirable properties; low digestion rate and high digestibility.

Specifically, the structural characteristics of the high molecular weight glucan according to the present invention satisfy the following properties (i) to (iii). The following properties (i) to (iii) are based on HPAEC-PAD analysis result of the unit chain length distribution obtained by isoamylase treatment which hydrolyze the α-1,6-glucoside bonds of the high molecular weight glucan into linear unit chain length, (i) the ratio of the total value of the peak areas for degrees of polymerization of 1 to 5 to the total value of the peak areas for degrees of polymerization of 6 to 10 (($DP_{1-5}/DP_{6-10}$)×100) is 33% to 50%, (ii) the ratio of the total value of the peak areas for degrees of polymerization of 11 to 15 to the total value of the peak areas for degrees of polymerization of 6 to 10 (($DP_{11-15}/DP_{6-10}$)×100) is 80% to 125%, and (iii) the ratio of the total value of the peak areas for degrees of polymerization of 26 to 30 to the total value of the peak areas for degrees of polymerization of 6 to 10 (($DP_{26-30}/DP_{6-10}$)×100) is 16% to 43%.

The high molecular weight glucan according to the present invention is characterized in that the $DP_{1-5}$ ratio defined in (i) is 33% to 50%, and its distribution exhibits peaks representing higher concentrations in a region of shorter chain lengths, in contrast to the known dextrin (see FIG. 1). To more effectively reduce the rate of digestion, the $DP_{1-5}$ ratio defined in (i) may preferably be 35% to 48%, or may more preferably be 35% to 45%.

The high molecular weight glucan according to the present invention is further characterized in that the $DP_{11-15}$ ratio defined in (ii) is 80% to 125%, and the total value of peak areas for degrees of polymerization of 6 to 10 and the total value of peak areas for degrees of polymerization of 11 to 15 have relatively approximate values. On the other hand, the $DP_{11-15}$ ratio of the known dextrin is way beyond 125%, and the high molecular weight glucan according to the present invention is thus structurally distinct from the known dextrin in terms of the $DP_{11-15}$ ratio as well (see FIG. 1). To more effectively reduce the rate of digestion, the $DP_{11-15}$ ratio defined in (ii) may preferably be 85% to 120%, or may more preferably be 90% to 110%.

The high molecular weight glucan according to the present invention is further characterized in that the $DP_{26-30}$ ratio defined in (iii) is 16% to 43%, and its distribution exhibits peaks representing higher concentrations in a region of longer chain lengths in contrast to the known dextrin (see FIG. 1). To more effectively reduce the rate of digestion, the $DP_{26-30}$ ratio defined in (iii) may preferably be 18% to 42%, or may more preferably be 20% to 41%.

The high molecular weight glucan according to the present invention characterized as follows may be more structurally suitable; the unit chain length distribution measured as described earlier fulfills, in addition to the properties (i) to (iii), at least one of, preferably three of, or more preferably all of the following four properties (iv) to (vii), (iv) the ratio of the total value of the peak areas for degrees of polymerization of 16 to 20 to the total value of the peak areas for degrees of polymerization of 6 to 10 (($DP_{16-20}/DP_{6-10}$)×100, which may be hereinafter referred to as "$DP_{16-20}$ ratio") is 53% to 85%, (v) the ratio of the total value of the peak areas for degrees of polymerization of 21 to 25 to the total value of the peak areas for degrees of polymerization of 6 to 10 (($DP_{21-25}/DP_{6-10}$)×100, which may be hereinafter referred to as "$DP_{21-25}$ ratio") is 31% to 62%, (vi) the ratio of the total value of the peak areas for degrees of polymerization of 31 to 35 to the total value of the peak areas for degrees of polymerization of 6 to 10 (($DP_{31-35}/DP_{6-10}$)×100, which may be hereinafter referred to as "$DP_{31-35}$ ratio")) is 8% to 30%, and (vii) the ratio of the total value of the peak areas for degrees of polymerization of 36 to 40 to the total value of the peak areas for degrees of polymerization of 6 to 10 (($DP_{36-40}/DP_{6-10}$)×100, which may be hereinafter referred to as "$DP_{36-40}$ ratio") is 3% to 21%.

The $DP_{16-20}$ ratio defined in (iv) may preferably be 55% to 84%, or may more preferably be 60% to 83%.

The $DP_{21-25}$ ratio defined in (v) may preferably be 35% to 61%, or may more preferably be 39% to 60%.

The $DP_{31-35}$ ratio defined in (vi) may preferably be 11% to 29%, or may more preferably be 14% to 29%.

The $DP_{36-40}$ ratio defined in (vii) may preferably be 5% to 20%, or may more preferably be 7% to 20%.

In one aspect of the high molecular weight glucan according to the present invention, the ratio of the total value of peak areas for degrees of polymerization of 1 to 5 to a total value of peak areas for degrees of polymerization of 1 to 50 in the unit chain length distribution measured as described earlier may be 7.0% to 14.0%, preferably 8% to 12%, or more preferably 8% to 10%.

In one aspect of the high molecular weight glucan according to the present invention, the ratio of a total value of peak areas for degrees of polymerization of 1 to 7 to the total value of peak areas for degrees of polymerization of 1 to 50 in the unit chain length distribution measured as described earlier may be 14% to 24%, preferably 15% to 22%, or more preferably 16% to 20%.

In one aspect of the high molecular weight glucan according to the present invention, the ratio of a total value of peak areas for degrees of polymerization of 1 to 10 to the total value of peak areas for degrees of polymerization of 1 to 50 in the unit chain length distribution measured as described earlier may be 24% to 40%, preferably 26% to 40%, or more preferably 18% to 36%.

In one aspect of the high molecular weight glucan according to the present invention, the ratio of a total value of peak areas for degrees of polymerization of 11 to 24 to the total value of peak areas for degrees of polymerization of 1 to 50 in the unit chain length distribution measured as described earlier may be 45% to 55%, preferably 46% to 53%, or more preferably 47% to 50%.

In one aspect of the high molecular weight glucan according to the present invention, the ratio of the total value of peak areas for degrees of polymerization of 6 to 10 to the total value of peak areas for degrees of polymerization of 1 to 50 in the unit chain length distribution measured as described earlier may be 20% to 30%, preferably 20% to 28%, or more preferably 20% to 26%.

In one aspect of the high molecular weight glucan according to the present invention, the ratio of a total value of peak areas for degrees of polymerization of 6 to 15 to the total value of peak areas for degrees of polymerization of 1 to 50 in the unit chain length distribution measured as described earlier may be 40% to 55%, preferably 40% to 54%, or more preferably 40% to 50%.

In one aspect of the high molecular weight glucan according to the present invention, the ratio of a total value of peak areas for degrees of polymerization of 6 to 40 to the total value of peak areas for degrees of polymerization of 1 to 50 in the unit chain length distribution measured as described earlier may be 85% to 90%, preferably 86% to 90%, or more preferably 87% to 90%.

In one aspect of the high molecular weight glucan according to the present invention, in the unit chain length distribution, a summed value of peak areas for degrees of polymerization of 1 to 10 and peak areas for degrees of polymerization of 25 to 50 is divided by the total planer dimension of peak areas for degrees of polymerization of 11 to 24, and a value calculated by the division, $(\{(DP_{1-10})+(DP_{25-50})\}/DP_{11-24})$ may be, for example, 1.0±0.2, or may preferably be 1.0±0.1.

In one suitable aspect of the high molecular weight glucan according to the present invention, the unit chain length distribution measured as described earlier exhibits no prominent value in any peak area ratios calculated for degrees of polymerization incremented/decremented by 1. Specifically, the ratio of the value of a peak area for each of degrees of polymerization of 1, . . . , 50 to the total value of peak areas for degrees of polymerization of 1 to 50 may be less than or equal to 6% or may preferably be less than or equal to 5%.

In one suitable aspect of the high molecular weight glucan according to the present invention, "slope of 20%-60% cumulative plotting" in the formula below which is calculated from the unit chain length distribution measured as described earlier may be less than or equal to 6 or may preferably be less than or equal to 5.5. The slope of 20%-60% cumulative plotting is correlated with the extent of unit chain length distribution. The value of this slope increases with more unit chain lengths associated with a particular range of degrees of polymerization.

Slope of 20%-60% cumulative plotting=$(DP_{1-X2}-DP_{1-X1})/(X2-X1)$,　　Formula 3:

where

X1: Smallest degree of polymerization among degrees of polymerization with total peak area ratios of 20% or more which is obtained by adding one by one, starting with "1" in degrees 1 to 50, the ratio of a peak area for each of degrees of polymerization of 1, . . . , 50 to a total peak area for degrees of polymerization of 1 to 50.

X2: Largest degree of polymerization among degrees of polymerization with total peak area ratios of 60% or less which is obtained by adding one by one, starting with "1" in degrees 1 to 50, the ratio of a peak area for each of degrees of polymerization of 1, . . . , 50 to a total peak area for degrees of polymerization of 1 to 5.

$DP_{1-X1}$: Ratio of a total peak area for degrees of polymerization of 1 to X1 to a total peak area for all of degrees of polymerization of 1 to 50.

$DP_{1-X2}$: Ratio of a total peak area for degrees of polymerization of 1 to X2 to a total peak area for all of degrees of polymerization of 1 to 50.

Among all of the degrees of polymerization in the unit chain length distribution, the degrees of polymerization of 1 to 50 may suffice to determine properties of the unit chain length distribution. In the unit chain length distribution thus measured, however, peaks may be distributed in a range of degrees of 1 to 1,000, preferably 1 to 200, or more preferably 1 to 100.

In order to obtain linear unit chain lengths by digesting α-1,6-glucoside bonds of the high molecular weight glucan using isoamylase to measure the unit chain length distribution, incubation under the following conditions is suggested; incubated at 37° C. for approximately 18 hours in a reaction solution containing 2.5 mg/mL of the high molecular weight glucan; measurement target, and 10 U/mL of isoamylase (20 mM acetic acid buffer solution, pH 5.5). The HPAEC-PAD method may confirm whether the unbranched linear unit chain lengths have been obtained. The isoamylase used then may be *Pseudomonas isoamylase* available from Megazyme Corporation.

2-4. In Vitro Digestibility

The high molecular weight glucan according to the present invention thus advantageously characterized may have the following two digestive properties; low digestion rate which is slowly digested in the body and dose not raise rapidly blood glucose level and blood insulin level, and high digestibility which is enabled by the substantial absence of indigestible components in the high molecular weight glucan.

Specifically, according to one aspect of the digestive properties of the high molecular weight glucan described herein, in the in vitro digestibility test described later, a digestion rate coefficient (initial digestion rate coefficient) k in 30 minutes of the reaction being initiated is less than 0.029, preferably 0.010 to 0.028, or more preferably 0.020 to 0.027.

According to one aspect of the digestive properties of the high molecular weight glucan described herein, in the in vitro digestibility test described later, the ratio of remained components in 120 minutes of the enzymatic reaction being initiated (indigestible fraction) is less than 10%, preferably 0% to 9%, or more preferably 0% to 8%.

According to one aspect of the digestive properties of the high molecular weight glucan described herein, in the in vitro digestibility test described later, the ratio of hydrolysis components in 20 minutes of the enzymatic reaction being initiated (rapid-digestible fraction) is less than 45%, preferably 10% to 43%, or more preferably 20% to 41%.

According to one aspect of the digestive properties of the high molecular weight glucan described herein, in the in vitro digestibility test described later, the ratio of hydrolysis components in 120 minutes after 20 minutes of the enzymatic reaction being initiated (slow-digestible fraction) is greater than or equal to 50%, preferably 51% to 90%, or more preferably 52% to 80%.

The in vitro digestibility test is performed as in the following procedure.

How to Perform In Vitro Digestibility Test

The method proposed by Englyst et al. (European Journal of Clinical Nutrition, 1992, 46, S33~S50) was altered and used in the digestibility test. The following materials are mixed; 100 µL of a 5 w/v % high molecular weight glucan aqueous solution, 20 µL of a 1 M acetic acid buffer (pH 5.5), and 716 µL of distilled water. Then, 4 µL of porcine pancreas α-amylase solution prepared in the concentration of 250 U/mL, and 160 µL of an extract of rat small intestine acetone powder prepared in a concentration equivalent to 0.3 U/mL of α-glucosidase activity are further added to the obtained mixture, and then reacted at 37° C. To obtain the extract of rat small intestine acetone powder, 150 mg of rat small intestine acetone powder is suspended in 3 mL of a 50 mM acetic acid buffer (pH 5.5), and a centrifuge supernatant is prepared as a crude enzyme solution for rat small intestine acetone powder. Over time during the reaction, a glucose concentration in each reaction solution is measured, and the content of glucose liberated from the high molecular weight glucan is measured. More specifics of the testing method will be described in working examples later. As the porcine pancreas α-amylase and rat small intestine acetone powder may be used products available from Sigma Chemical Co.

The initial digestion rate coefficient k is obtained by the Logarithm of the slope (LOS) plotting proposed by Butterworth et al., (Carbohydrate Polymers 87 (2012) 2189-2197). Specifically, the initial digestion rate coefficient k is calculated by the following formula.

$$\ln(1-C_t)=-kt,\qquad\text{Formula 4:}$$

where t is reaction time (min.), and $C_t$ is (amount of glucose produced until reaction time t is reached)/(total amount of glucose in high molecular weight glucan), the initial digestion rate coefficient k is calculated from slope of a primary regression line on plotted time t and $\ln(1-C_t)$ in 30 minutes from reaction time=0 minute.

The rapid-digestible fraction, slow-digestible fraction, and indigestible fraction (%) included in the high molecular weight glucan are calculated by the following formulas.

Rapid-digestible fraction (%)={(amount of glucose produced in 20 minutes of reaction being initiated)/(total amount of glucose)}×100

Slow-digestible fraction (%)={(amount of glucose produced in 120 minutes of reaction being initiated)−(amount of glucose produced in 20 minutes of reaction being initiated)/(total amount of glucose)}×100

Indigestible fraction (%)={(total amount of glucose)−(amount of glucose produced in 120 minutes of digestion being initiated)/(total amount of glucose)}×100      Formula 5:

2-5. Applications of High Molecular Weight Glucan

Applications of the high molecular weight glucan according to the present invention may be similar to those of the known starches. Specifically, the high molecular weight glucan according to the present invention may be applicable to a diverse range of products including drinks, foods, infusions, food additives, pharmaceutical products, and adhesives. When the high molecular weight glucan according to the present invention is dissolved in water, the resulting gelatinized fluid has a relatively low viscosity. The high molecular weight glucan according to the present invention, therefore, may be useful as, for example, raw materials of biodegradable plastics, intermediate materials in starch-used cyclodextrin making processes, and raw materials used in starch processing industry.

The high molecular weight glucan according to the present invention; effective energy source for human bodies, may be suitable ingredients of drinks and foods. The high molecular weight glucan according to the present invention achieving both of low digestion rate and high digestibility may be suitable for drinks and foods prepared for those who need to control spikes in their blood glucose level and blood insulin level, and such drinks and foods may be offered as diet products targeted for those need to control spikes in their blood glucose level and blood insulin level. Suitable examples of foods and drinks to which the high molecular weight glucan according to the present invention is addable may include coffees, soy sauces, dipping sauce, dipping broths for noodles, sauces, instant bouillons, stew sauce mixes, soup stock cubes, seasoning mixes, curry sauce mixes, jellies, caramels, chewing gums, chocolates, cookies, crackers, ice creams, sherbets, juices, powdered juices, fresh Japanese confectionery, fresh Western confectionery, frozen foods, chilled foods, rice cakes, rice balls, drinks and foods ingested during or after playing sports (sports drinks and foods), and medical foods and drinks targeted for patients under peritoneal dialysis, or patients with diabetes or kidney disease.

When the high molecular weight glucan according to the present invention is added to these products, its content may be suitably decided in accordance with types, shapes, and forms of such products. For example, a food and/or drink composition may contain 100 mass % or less, preferably 75 mass % or less, or more preferably 50 mass % or less of the high molecular weight glucan according to the present invention. While the lower-limit content of the high molecular weight glucan according to the present invention added to such a composition is not particularly limited, the high molecular weight glucan content in such a composition may be greater than or equal to 0.1 mass %, preferably greater than or equal to 1 mass %, more preferably greater than or equal to 3 mass %, even more preferably greater than or equal to 8 mass %, or most preferably greater than or equal to 10 mass %. The content of the high molecular weight glucan according to the present invention in such a composition may specifically range from 0.1 to 100 mass %, preferably from 1 to 100 mass %, more preferably from 3 to 100 mass %, even more preferably from 8 to 75 mass %, or most preferably from 10 to 50 mass %.

As described earlier, the high molecular weight glucan according to the present invention may be useful as an energy source for human bodies and may enable control of spikes in blood glucose level and/or blood insulin level. The high molecular weight glucan according to the present invention, therefore, may be an effective agent for control of rise in blood glucose level and/or blood insulin level that can be added to, for example, foods, drinks, and pharmaceutical products. Thus, the present invention further provides use of the high molecular weight glucan according to the present invention to product as agent that controls rise in blood glucose level and/or a blood insulin level. The present invention further provides a method for controlling rise in blood glucose level and/or blood insulin level, including administering the high molecular weight glucan, as a carbohydrate source, to a person who needs to control rise in blood glucose level and/or blood insulin level. In this method, the high molecular weight glucan may be administered in a dose of, for example, approximately 1 g to 200 g.

3. Production Method for High Molecular Weight Glucan

While the production method for the high molecular weight glucan according to the present invention is not particularly limited, suitable examples of the method may be 1) a method including: making 100 to 4,000 U/g substrate of branching enzyme and 4-α-glucanotransferase react with a branched glucan which is used as substrate all at once or stepwise in any order; and terminating the reactions at a point in time after the high molecular weight glucan as described in any one of the technical aspects 1 to 5 is produced (hereinafter, first method), and 2) a method including: making 100 to 4,000 U/g substrate of branching enzyme react with a branched glucan which is used as substrate, and then making exo-type amylase react with the branched glucan; and terminating the reactions at a point in time after the high molecular weight glucan according to the present invention is produced (hereinafter, second method). Hereinafter are described the first and second methods for producing the high molecular weight glucan according to the present invention.

3-1. First Method

3-1-1. Substrate

The substrate used in the first method is a branched glucan. The branched glucan used in the present invention is a glucan in which linear chain glucan including D-glucoses linked by α-1,4-glucoside bonds is branched by α-1,6-glucoside bonds. In the present invention, the branched glucan may preferably be a glucan in which the linear chain glucan is not branched by any bonds but the α-1,6-glucoside bonds. If the substrate has a structural moiety branched by any bonds but the α-1,6-glucoside bonds, they may remain in the synthesized high molecular weight glucan. Such a structural moiety may lead to resistance to digestion, resulting in failure to obtain the high molecular weight glucan achieving high digestibility pursued by the present invention. Desirably, the branched glucan used as substrate is subjected to neither of isoamylase treatment nor pullulanase treatment.

The branch frequency in the branched glucan used as substrate is not particularly limited. As for its lower limit, the branch frequency may be, for example, greater than or equal to 3%, preferably greater than or equal to 4%, more preferably greater than or equal to 5%, or even more preferably greater than or equal to 6%. Since the branch frequency is typically not very high in native branched glucans, the branch frequency may be, for example, less than or equal to 10%, less than or equal to 9%, less than or equal to 8%, or less than or equal to 7%. The branch frequency in the branched glucan used as substrate may specifically range from 3% to 10%, preferably from 4% to 9%, or more preferably from 5% to 8%.

The average degree of polymerization in the branched glucan used as substrate is not particularly limited. As for its lower limit, for example, the average degree of polymerization may be greater than or equal to approximately 70, preferably greater than or equal to approximately 80, more preferably greater than or equal to approximately 90, or even more preferably greater than or equal to approximately 100. As for its upper limit, for example, the average degree of polymerization in the branched glucan used as substrate may be less than or equal to approximately $1\times10^7$, preferably less than or equal to approximately $3\times10^6$, more preferably less than or equal to approximately $1\times10^6$, even more preferably less than or equal to approximately $5\times10^5$, or most preferably less than or equal to approximately $3\times10^5$. The average degree of polymerization in the branched glucan used as substrate may specifically range from approximately 70 to approximately $1\times10^7$, preferably from approximately 80 to approximately $3\times10^6$, more preferably from approximately 90 to approximately $1\times10^6$, even more preferably approximately 100 to approximately $5\times10^5$, or most preferably from approximately 100 to approximately $3\times10^5$.

Suitable examples of the branched glucan used as substrate may include starches, amylopectins, glycogens, dextrins, enzymatically synthesized branched glucans, and highly-branched cyclic glucans. These branched glucans are hereinafter described in detail.

Starch

The "starch" described herein refers to a mixture of amylose and amylopectin. The starch described herein as substrate may preferably have a large content of amylopectin and may be any suitable one selected from typical starches that are commercially available. The proportion of amylose and amylopectin included in the starch depends on the type of a plant used to produce the starch. Starches obtained from glutinous rice and glutinous corns are mostly consisting of amylopectin. Starches solely consisting of amylose in the absence of amylopectin are not obtainable from typical plants. Starches are typically divided into native starches, starch degradation products, and modified starches. Among them, the substrate used in the present invention may be selected from native starches and their degraded products, or may preferably be selected from native starches.

The native starches may be divided into tuber starches and cereal starches, any one of which may be used as the substrate described herein. Examples of the tuber starches may include potato starches, tapioca starches, sweet potato starches, kudzu (Japanese arrowroot) starches, and warabi (Japanese bracken) starches. Examples of the cereal starches may include corn starches, wheat starches, and rice starches. Other examples of the native starches may include high-amylose starches (for example, high-amylose corn starches) and waxy starches. The starch described herein may be a soluble starch. The soluble starch may be a water-soluble starch obtained by subjecting a native starch to various treatments. The substrate used in the present invention may preferably be selected from waxy starches.

The starch used as substrate may be prepared in the form of starch granules. The "starch granules" described herein indicate starch molecules at least partly retaining its native crystalline structure. The starch granules may be unmodified starch granules or may be granules obtained by subjecting unmodified starch granules to a chemical modification or a physical treatment. When it is desirable to use an enzymatically modified starch classified as food, starch granules preferably used are typically raw starch granules obtained from plants, for example, starch granules yet to be gelatinized. Other examples of the starch granules may include any starch granules exhibiting such a property that a suspension containing the starch granules loses fluidity when the granules are burst by heating. The starch granules used as substrate may preferably have a large content of amylopectin.

Plants stored starch molecules as granules (i.e., large crystalline structure) in amyloplast, and they are called starch granules. The starch granules, in which starch molecules are linked by hydrogen bonds, are hardly directly soluble in water and are difficult to digest. The starch granules heated in water start to swell and eventually become colloidal as their molecules are loosened. This transformation is referred to as "gelatinization". The sizes and forms of starch granules depend on the type of a plant used to produce the starch granules. For example, corn starch granules may have an average granule size of approximately 12 µm to approximately 15 m, thus showing relatively small and substantially uniform granules, as compared with other starch granules. Granules of wheat and barley starches may be roughly divided into relatively large granules having an average granule size of approximately 20 m to 40 m, and relatively small granules sizes having an average granule size of several m. Rice starches have a compound grain structure composed of a large number of angular granules of a few m that are built up in amyloplast. Potato starch granules have an average granule size of approximately 40 am, which may be the largest among the starch raw materials typically available. The present invention may use, as substrate, any one(s) selected from the commercially available starch granules. Starch granules obtained from plants may be, for example, refined and prepared to be used as substrate.

Any starch granules composed of tightly bonded starch molecules may be hardly affected by an enzymatic behavior. In particular embodiments that pursue enzymatically modified starches handled as food, preferably, the starch granules used may be isolated from a plant or refined without being subjected to acid treatment, chemical modification, or heat treatment. The "unmodified" or "untreated" starch granules described herein refer to native starch granules that are not exposed to any treatments but treatments required to isolate the starch granules from the other natively coexisting components (for example, proteins, lipids). This description, therefore, exclude from the treatments of starch granules any steps of preparing the starch granules, for example, removal of impurity and refinement of a starch obtained from a plant. The starch granules may be any ones selected from the commercially accessible starch granules.

The starch granules are preferably not gelatinized. Any enzymatic behavior may be difficult to act upon starch granules at least partly retaining its native crystalline structure. As for the properties of starch granules, the suspension of starch granules may preferably lose fluidity. The suspension of starch granules, for example, can be prepared by follows. The starch granules added to 30° C. water to prepare a 40 wt. % aqueous suspension were heated for 10 minutes at 100° C. and then cooled to 60° C. In this description, "losing fluidity" or "no fluidity" means that, when a 100-mL glass beaker containing 50 g of a solution that has been heated for 10 minutes (60° C.) is reversed to afford unobstructed condition under the sample solution, and then left for one minute at 60° C., 20 wt. % or more of the solution (i.e., 10 g or more) remains inside the beaker. It may be difficult to evenly disperse any enzyme in a solution with no fluidity. On the other hand, "solution with fluidity" or "fluid solution" means that, when a 100-mL glass beaker containing a solution is reversed, 80% or more of the solution flows down out of the beaker under the gravity in one minute or less. Starches may be evenly dispersible in such a fluid solution when an enzyme is added to and stirred in this solution. Fluid solutions may be unlikely to clog or block any equipment in typical production lines.

A modified starch, if used as substrate, may preferably be subjected to at least one of a chemical modification and a physical treatment.

Examples of the chemically modified starches may include acetylated distarch adipate, acetylated oxidized starch, acetylated distarch phosphate, starch sodium octenyl succinate, starch acetate, oxidized starch, bleached starch, hydroxypropyl distarch phosphate, hydroxypropyl starch, distarch phosphate, monostarch phosphate, and phosphated distarch phosphate. The "acetylated distarch adipate" refers to a starch esterified with acetic anhydride and adipate anhydride. The "acetylated oxidized starch" refers to a starch modified with sodium hypochlorite and then esterified with acetic anhydride. The "acetylated distarch phosphate" refers to a starch esterified with sodium trimetaphosphate or oxyphosphorus chloride and with acetate anhydride or vinyl acetate. The "starch sodium octenyl succinate" refers to a starch esterified with octenyl succinic anhydride. The "starch acetate" refers to a starch esterified with acetate anhydride or vinyl acetate. The "oxidized starch" refers to a starch modified with sodium hypochlorite; equivalent to 1.1% or less of carboxy groups (may be referred to as carboxyl groups) determined by an analysis of carboxy groups in a sample starch performed pursuant to the purity testing method set forth in the announcement No. 485, Health, Labor and Welfare Ministry. None of the "bleached starches" having a content of carboxy groups within this range is included in the definition of "oxidized starch". The "bleached starch" refers to a starch modified with sodium hypochlorite and determined as containing 0.1% or less of carboxy groups by an analysis of carboxy groups in a sample starch performed pursuant to the purity testing method set forth in the announcement No. 485, Health, Labor and Welfare Ministry, and starches that can be tested negative in the "verification test (3)" for oxidized starch set forth in the announcement No. 485, Health, Labor and Welfare Ministry and that can rationally demonstrate that any changes in their properties such viscosity are irrelevant to oxidization. Starches changed in properties, such as viscosity, from their native states are included in the category of oxidized starch, regardless of the content of carboxy groups being 0.1% or less. In Japan, such starches are not handled as food but are handled as food additives. The "hydroxypropyl distarch phosphate" refers to a starch esterified with sodium trimetaphosphate or phosphorus oxychloride and then etherified with propylene oxide. The "hydroxypropyl starch" refers to a starch etherified with propylene oxide. The "distarch phosphate" refers to a starch esterified with sodium trimetaphosphate or phosphorus oxychloride. The "monostarch phosphate" refers to a starch esterified with orthophosphoric acid and its potassium salt or with sodium chloride or sodium tripolyphosphate. The "phosphated distarch phosphate" refers to a starch esterified with orthophosphoric acid and its potassium salt or sodium salt or sodium tripolyphosphate and further esterified with sodium trimetaphosphate or phosphorus oxychloride.

Examples of the starches subjected to the physical treatment may include heat-moisture treated starches and thermally inhibited starches. The "heat-moisture treated starch" refers to a modified starch obtained by heating a starch with a water content low enough not to gelatinize the starch. The "water content low enough not to gelatinize the starch" specifically indicates a water content of less than or equal to approximately 50 wt. %, preferably of approximately 5 wt.

% to 30 wt. %, more preferably of approximately 5 wt. % to 25 wt. %, or even more preferably of approximately 5 wt. % and 20 wt. %. The "thermally inhibited starch" refers to a modified starch enhanced in crystalline structure by further dry heating starch granules already dried and lowered in water content. The "starch granules dried and lowered in water content" specifically indicates that the water content of starch granules is less than approximately 1% or preferably substantially 0%.

The average degree of polymerization of the starch used as substrate is not particularly limited. For example, the average degree of polymerization may be greater than or equal to approximately $1 \times 10^3$, preferably greater than or equal to approximately $5 \times 10^3$, more preferably greater than or equal to approximately $1 \times 10^4$, or even more preferably greater than or equal to approximately $2 \times 10^4$. The upper limit is also not particularly limited for the average degree of polymerization of the starch used as substrate. For example, the average degree of polymerization may be less than or equal to approximately $1 \times 10^7$, preferably less than or equal to approximately $3 \times 10^6$, more preferably less than or equal to approximately $1 \times 10^6$, or even more preferably less than or equal to approximately $3 \times 10^5$. The average degree of polymerization of the starch used as substrate may be specifically approximately $1 \times 10^3$ to approximately $1 \times 10^7$, preferably approximately $5 \times 10^3$ to approximately $3 \times 10^6$, more preferably approximately $1 \times 10^4$ to approximately $1 \times 10^6$, or even more preferably approximately $2 \times 10^4$ to approximately $3 \times 10^5$.

Amylopectin

Amylopectin is a branched molecule in which glucose units linked by α-1,4-glucoside bonds are branched by α-1,6-glucoside bonds. The amylopectin is included in native starches. The amylopectin described herein may be a waxy corn starch solely consisting of amylopectin.

The average degree of polymerization of the amylopectin used as substrate is not particularly limited. For example, the average degree of polymerization may be greater than or equal to approximately $1 \times 10^3$, preferably greater than or equal to approximately $5 \times 10^3$, more preferably greater than or equal to approximately $1 \times 10^4$, or even more preferably greater than or equal to approximately $2 \times 10^4$. Further, no particular upper limit is set for the average degree of polymerization of the amylopectin used as substrate. For example, the average degree of polymerization may be less than or equal to approximately $1 \times 10^7$, preferably less than or equal to approximately $3 \times 10^6$, more preferably less than or equal to approximately $1 \times 10^6$, or even more preferably less than or equal to approximately $3 \times 10^5$. The average degree of polymerization of the amylopectin used as substrate may be specifically approximately $1 \times 10^3$ to approximately $1 \times 10^7$, preferably approximately $5 \times 10^3$ to approximately $3 \times 10^6$, more preferably approximately $1 \times 10^4$ to approximately $1 \times 10^6$, or even more preferably approximately $2 \times 10^4$ to approximately $3 \times 10^5$.

Glycogen

Glycogen is a type of glucan composed of glucoses and having a high frequency of branching. The glycogen is widely distributed in most of cells of animals as storage polysaccharide. The glycogen is also found in some plants, for example, seeds of sweet corn species among the corns. The glycogen is typically so structured that sugar chains of α-1,4-glucoside bonds of glucose having an average degree of polymerization of 12 to 18 are linked by α-1,6-glucoside bonds at the ratio of approximately one each for three glucose units. In the branched chains linked by α-1,6-glucoside bonds, similarly, sugar chains of α-1,4-glucoside bonds of glucose are linked by α-1,6-glucoside bonds. Thus, the glycogen has a network structure.

The glycogen used as substrate may be of animal origin or plant origin. The glycogen is known to be producible through enzymatic synthesis (Japanese Patent Laid-open Publication No. 2008-095117). The present invention may use, as substrate, a glycogen thus produced through enzymatic synthesis.

The lower-limit average degree of polymerization of the glycogen used as substrate is not particularly limited. For example, the average degree of polymerization may be greater than or equal to approximately 500, preferably greater than or equal to approximately $1 \times 10^3$, preferably greater than or equal to approximately $2 \times 10^3$, or more preferably greater than or equal to approximately $3 \times 10^3$. Further, no particular upper limit is set for the average degree of polymerization of the glycogen used as substrate. For example, the average degree of polymerization may be less than or equal to approximately $1 \times 10^7$, preferably less than or equal to approximately $3 \times 10^6$, more preferably less than or equal to approximately $1 \times 10^6$, or even more preferably less than or equal to approximately $3 \times 10^5$. The average degree of polymerization of the glycogen used as substrate may be specifically approximately 500 to approximately $1 \times 10^7$, preferably approximately $1 \times 10^3$ to approximately $3 \times 10^6$, more preferably approximately $2 \times 10^3$ to approximately $1 \times 10^6$, or even more preferably approximately $3 \times 10^3$ to approximately $3 \times 10^5$.

The glycogen used as substrate may be a chemically modified glycogen derivative. Examples of the glycogen derivative may include derivatives in which at least one of alcoholic hydroxyl groups of the glycogen is chemically modified by, for example, glycosylation, hydroxyalkylation, alkylation, acetylation, carboxymethylation, sulphation, or phosphorylation. The glycogen derivative may include one kind of chemical modification or two or more kinds of different chemical modifications in its one molecule each.

Dextrin

Dextrin is a type of glucan composed of glucoses and having a level of complexity between those of starch and maltose. The dextrin is producible by partially decomposing a starch using an acid, alkali, or enzyme.

No particular lower limit is set for the average degree of polymerization of the dextrin used as substrate. For example, the average degree of polymerization may be greater than or equal to approximately 50, preferably greater than or equal to approximately 60, more preferably greater than or equal to approximately 70, or even more preferably greater than or equal to approximately 80. Further, no particular upper limit is set for the average degree of polymerization of the dextrin used as substrate. For example, the average degree of polymerization may be less than or equal to approximately $1 \times 10^4$, preferably less than or equal to approximately $9 \times 10^3$, more preferably less than or equal to approximately $7 \times 10^3$, or even more preferably less than or equal to approximately $5 \times 10^3$. The average degree of polymerization of the dextrin used as substrate may be specifically approximately 50 to approximately $1 \times 10^4$, preferably approximately 60 to approximately $9 \times 10^3$, more preferably approximately 70 to approximately $7 \times 10^3$, or even more preferably approximately 80 to approximately $5 \times 10^3$.

The dextrin used as substrate may be a chemically modified dextrin derivative. Examples of the dextrin derivative may include derivatives in which at least one of alcoholic hydroxyl groups of the dextrin is chemically modified by, for example, glycosylation, hydroxyalkylation, alkylation, acetylation, carboxymethylation, sulphation, or phosphorylation. The dextrin derivative may include one kind of chemical modification or two or more kinds of different chemical modifications in its one molecule each.

Enzymatically Synthesized Branched Glucan

The enzymatically synthesized branched glucan refers to a branched glucan synthesized with the use of an enzyme(s). A glucan having a branching structure may be synthesized by adding a branching enzyme to a reaction solution in the process of synthesizing amylose using the SP-GP method (WO 02/097107 (Pages 127-134), H. Waldmann et al., Carbohydrate Research, 157 (1986) c4-c7). The frequency of branching may be suitably adjusted by changing the amount of the branching enzyme to be added.

No particular lower limit is set for the average degree of polymerization of the enzymatically synthesized branched glucan used as substrate. For example, the average degree of polymerization may be greater than or equal to approximately 70, preferably greater than or equal to approximately 80, more preferably greater than or equal to approximately 100, or even more preferably greater than or equal to approximately 200. Further, no particular upper limit is set for the average degree of polymerization of the enzymatically synthesized branched glucan used as substrate. For example, the average degree of polymerization may be less than or equal to approximately $2\times10^5$, preferably less than or equal to approximately $1\times10^5$, more preferably less than or equal to approximately $5\times10^4$, or even more preferably less than or equal to approximately $3\times10^4$. The average degree of polymerization of the enzymatically synthesized branched glucan; substrate may be specifically approximately 70 to approximately $2\times10^5$, preferably approximately 80 to approximately $1\times10^5$, more preferably approximately 100 to approximately $5\times10^4$, or even more preferably approximately 200 to approximately $3\times10^4$.

The enzymatically synthesized branched glucan; substrate, may be a chemically modified, enzymatically synthesized branched glucan derivative. Examples of such a branched glucan derivative may include derivatives in which at least one of alcoholic hydroxyl groups of the enzymatically synthesized branched glucan is chemically modified by, for example, glycosylation, hydroxyalkylation, alkylation, acetylation, carboxymethylation, sulphation, or phosphorylation. The enzymatically synthesized branched glucan derivative may include one kind of chemical modification or two or more kinds of different chemical modifications in its one molecule each.

Highly-Branched Cyclic Glucan

The highly-branched cyclic glucan is a glucan with an inner branched cyclic structural moiety and an outer branched structural moiety, which is produced by the method described in Japanese Patent No. 3107358. In this method described in Japanese Patent No. 3107358, BE, 4-α-glucanotransferase or cyclodextrin glucanotransferase (CGTase) is independently used for reaction, the obtained highly-branched cyclic glucan has a chain length distribution distinct from that of the high molecular weight glucan according to the present invention. The highly-branched cyclic glucan should have at least one branch in the whole molecules.

No particular lower limit is set for the average degree of polymerization in the whole molecules of the highly-branched cyclic glucan used as substrate. For example, the average degree of polymerization may be greater than or equal to approximately 50, preferably greater than or equal to approximately 60, more preferably greater than or equal to approximately 80, or even more preferably greater than or equal to approximately 100. Further, no particular upper limit is set for the average degree of polymerization in the whole molecules of the highly-branched cyclic glucan used as substrate. For example, the average degree of polymerization may be less than or equal to approximately $1\times10^4$, preferably less than or equal to approximately $7\times10^3$, more preferably less than or equal to approximately $5\times10^3$, or even more preferably less than or equal to approximately $4\times10^3$. The average degree of polymerization in the whole molecules of the highly-branched cyclic glucan; substrate, may be specifically approximately 50 to approximately $1\times10^4$, preferably approximately 60 to approximately $7\times10^3$, more preferably approximately 80 to approximately $5\times10^3$, or even more preferably approximately 100 to approximately $4\times10^3$.

No particular lower limit is set for the average degree of polymerization in the inner branched cyclic structural moiety present in the highly-branched cyclic glucan. For example, the average degree of polymerization may be greater than or equal to approximately 10, preferably greater than or equal to approximately 15, or more preferably greater than or equal to approximately 20. Further, no particular upper limit is set for the average degree of polymerization in the inner branched cyclic structural moiety present in the highly-branched cyclic glucan. For example, the average degree of polymerization may be less than or equal to approximately 500, preferably less than or equal to approximately 300, or more preferably less than or equal to approximately 100. The average degree of polymerization in the inner branched cyclic structural moiety may specifically range from approximately 10 to 500, preferably from approximately 15 to 300, or more preferably from approximately 20 to 100.

No particular lower limit is set for the average degree of polymerization in the outer branched structural moiety present in the highly-branched cyclic glucan. For example, the average degree of polymerization may be greater than or equal to approximately 40, preferably greater than or equal to approximately 100, or more preferably greater than or equal to approximately 300. Further, no particular upper limit is set for the average degree of polymerization in the outer branched structural moiety present in the highly-branched cyclic glucan. For example, the average degree of polymerization may be less than or equal to approximately $3\times10^3$, preferably less than or equal to approximately $1\times10^3$, or more preferably less than or equal to approximately 500. The average degree of polymerization in the outer branched structural moiety may specifically range from approximately 40 to approximately $3\times10^3$, preferably from approximately 100 to approximately $1\times10^3$, or more preferably from approximately 300 to approximately 500.

The inner branched cyclic structural moiety present in the highly-branched cyclic glucan may include at least one α-1,6-glucoside bond. The number of α-1,6-glucoside bonds may be, for example, one or more α-1,6-glucoside bond, five or more α-1,6-glucoside bonds, or 10 or more α-1,6-glucoside bonds. The number of α-1,6-glucoside bonds in the inner branched structural moiety may be, for example, less than or equal to approximately 200, less than or equal to approximately 50, less than or equal to approximately 30, less than or equal to approximately 15, or less than or equal to approximately 10. The number of α-1,6- glucoside bonds in the inner branched structural moiety may be 1 to 200, preferably 5 to 50, or more preferably 10 to 30.

The highly-branched cyclic glucan having a certain degree of polymerization may be singly used, or the highly-branched cyclic glucan may be a combination of two or more highly-branched cyclic glucans having different degrees of polymerization. When two or more highly-branched cyclic glucans having different degrees of polymerization are combined and used, the ratio of the largest and smallest degrees of polymerization may be less than or equal to approximately 100, preferably less than or equal to approximately 50, or more preferably less than or equal to approximately 10.

The highly-branched cyclic glucan used as substrate may preferably be a glucan including an inner branched cyclic structural moiety and an outer branched structural moiety, having a degree of polymerization of 50 to $5\times10^3$, and further characterized in that the inner branched cyclic structural moiety is a cyclic structural moiety formed by α-1,4-glucoside bonds and α-1,6-glucoside bonds, and the outer branched structural moiety is a non-cyclic structural moiety linked to the inner branched cyclic structural moiety. The degrees of polymerization of unit chains in the outer branched structural moiety may be, on average, greater than or equal to approximately 10 and preferably less than or equal to approximately 20.

The highly-branched cyclic glucan is commercially available from, for example, EZAKI GLICO CO., LTD., which is sold under the trade name of "Cluster Dextrin", which may be employed as substrate in the present invention.

The highly-branched cyclic glucan; substrate, may be a chemically modified, highly-branched cyclic glucan derivative. Examples of such a derivative may include derivatives in which at least one of alcoholic hydroxyl groups of the highly-branched cyclic glucan is chemically modified by, for example, glycosylation, hydroxyalkylation, alkylation, acetylation, carboxymethylation, sulphation, or phosphorylation. The highly-branched cyclic glucan derivative may include one kind of chemical modification or two or more kinds of different chemical modifications in its one molecule each.

3-1-2. Enzyme

Branching Enzyme (BE)

The branching enzyme (synthetic name: 1,4-α-D-glucan: 1,4-α-D-glucan, 6-α-D-(1,4-α-D-glucano)-transferase, EC 2.4.1.18; hereinafter may be referred to as BE) is an enzyme that cuts α-1,4-glucoside bond and transfers its reducing end to OH group at 6-position of another glucose residue to form α-1,6-glucoside bond. In the relevant technical field, BE may be called otherwise; 1,4-α-glucan branching enzyme, branch forming enzyme, or Q-enzyme. BE is widely distributed in animals, plants, filamentous fungi, ferments, and bacteria, and catalyzes branching, bonding, and synthesis of glycogens or starches.

BE used in the production of the high molecular weight glucan according to the present invention may preferably be heat-resistant BE. The heat-resistant BE includes BE having an optimal reaction temperature higher than or equal to 45° C. when the branching enzyme activity is measured at varying reaction temperatures.

The branching enzyme activity (BE activity) is the activity to decrease the absorbance at 660 nm of an amylose-iodine composite. This activity is exerted through the action of BE that cuts α-1,4-glucoside bond and transfers its reducing end to OH group at 6-position of another glucose residue to form α-1,6-glucoside bond and decrease the linear chain moiety of amylose.

BE activity measuring methods are the known techniques in the relevant technical field, an example of which is recited in Takata, H. et al., J. Appl. Glycosci., 2003.50:p. 15-20. The branching enzyme activity of BE may be measured as described below. First, 50 μL of an enzyme solution is added to 50 μL of a substrate solution (0.12% (w/v) amylose (Type III, available from Sigma Chemical Co.), and the reaction is initiated. The optimal reaction temperature of BE is set and kept throughout the reaction. After BE is acted upon the substrate for 10 minutes, 1 mL of 0.4 mM hydrochloric acid solution is added to the mixture to terminating the reaction. Then, 1 mL of an iodine solution is added to and stirred well with the mixture, and the absorbance at 660 nm is measured. A control solution is also prepared, to which the 0.4 mM hydrochloric acid solution is added before the enzyme solution is added. A substrate solution used then is prepared as follows; 200 μL of a 50 mM potassium phosphate buffer solution (pH 7.5) and 700 μL of distilled water are added to 100 μL of a 1.2% (w/v) amylose Type III solution (dissolved in dimethyl sulfoxide), and this mixture is stirred well. Buffer pH is adjusted so as to conform to the optimal reaction pH of BE. An iodine solution used then is prepared as follows; 0.5 mL of 1 N hydrochloric acid is mixed with 0.125 mL of a stock solution (aqueous solution containing 2.6 wt. % of 12 and 26 wt. % of KI) and is then further mixed with distilled water so as to amount to 65 mL. BE activity of the enzyme solution is calculated by the following formula based on the absorbance at 660 nm thus calculated.

$$BE \text{ activity (unit (U)/mL)} = \frac{\begin{pmatrix} \text{control solution, 660-nm absorbency} - \\ \text{sample solution, 660-nm absorbency} \end{pmatrix}}{(\text{control solution, 660-nm absorbency})} \times$$

$$100 \times \frac{1}{10} \times \frac{1000}{50} \qquad \text{Formula 6}$$

Further, BE activity per 1 g of the substrate solution can be calculated from the obtained BE activity. The activity of BE described herein is, on principle, BE activity thus calculated. BE activity is expressed in "unit" or "U".

Typically, the optimal reaction temperature of BE is approximately 45° C. to approximately 90° C. The "optimal reaction temperature" described herein indicates a temperature at which the activity is maximized when BE activity measuring method is conducted at varying temperatures, with any other conditions remaining unchanged. The optimal reaction temperature of BE used in the present invention may be higher than or equal to approximately 45° C., preferably higher than or equal to approximately 50° C., more preferably higher than or equal to approximately 55° C., even more preferably higher than or equal to approximately 60° C., or most preferably higher than or equal to approximately 65° C. No particular upper limit is set for the optimal reaction temperature of BE used in the present invention. For example, the optimal reaction temperature may be lower than or equal to approximately 90° C., lower than or equal to approximately 85° C., lower than or equal to approximately 80° C., or lower than or equal to approximately 75° C.

BE used in the present invention may desirably have its BE activity exerted at a temperature at which this enzyme is acted upon the substrate. In this description, "BE activity exerted at a temperature at which this enzyme is acted upon the substrate" means that BE activity is detectable when measured under the same conditions as in the described BE activity measuring method, except that this enzyme is acted upon the substrate at the temperature, instead of its optimal reaction temperature. BE activity at the temperature at which BE is acted upon the substrate may be greater than or equal to approximately 10 U/mL, preferably greater than or equal to approximately 20 U/mL, more preferably greater than or equal to approximately 30 U/mL, even more preferably greater than or equal to approximately 40 U/mL, or most preferably greater than or equal to approximately 50 U/mL. BE activity at the temperature at which BE is acted upon the substrate may preferably be higher, the upper limit of which is not particularly limited. For example, BE activity at the temperature at which BE is acted upon the substrate may be less than or equal to 500,000 U/mL, less than or equal to 200,000 U/mL, less than or equal to 100,000 U/mL, less than or equal to 80,000 U/mL, or less than or equal to 50,000 U/mL.

BE is not particularly limited insofar as it is classified in EC 2.4.1.18 established by the International Union of Biochemistry and Molecular Biology. BE may be selected from bacterial enzymes of, for example the *Aquifex, Rhodothermus, Bacillus*, and *Thermosynechococcus*. Preferably, BE used in the present invention may be an *Aquifex* bacterial enzyme.

Specific examples of bacteria from which BE used in the present invention is derived may include *Aquifex aeolicus, Aquifex pyrophilus, Rhodothermus obamensis, Rhodothermus marinus, Bacillus stearothermophilus, Bacillus caldovelox, Bacillus thermocatenulatus, Bacillus caldolyticus, Bacillus flavothermus, Bacillus acidocaldarius, Bacillus caldotenax, Bacillus smithii, Thermosynechococcus elongatus*, and *Escherichia coli*. Among them, preferable candidates may be *Aquifex aeolicus, Rhodothermus obamensis, Bacillus stearothermophilus, Bacillus caldovelox, Bacillus thermocatenulatus, Bacillus caldolyticus*, and *Escherichia coli*, and more preferable candidates may be *Aquifex aeolicus* and *Rhodothermus obamensis*. In recent studies, thermophile *Bacillus* bacteria may be often described as *Geobacillus* bacteri. For example, *Bacillus stearothermophilus* and *Geobacillus stearothermophilus* refer to the same bacterium.

In this description, an enzyme being "derived" from an organism includes but is not limited to the enzyme being directly isolated from the organism. It may also indicate use of the organism in some kind of form to acquire the enzyme. For example, genes that code an enzyme acquired from an organism are introduced into a host, and the host is then cultured to acquire the enzyme, which is also referred to as being "derived" from the organism.

BE used in the present invention may be modified BE in which one or two or more amino acid residues are substituted with, deleted from, added to, and/or inserted in the amino acid sequence of wild-type BE. For example, WO2000/058445, describes a modified product of *Rhodothermus obamensis* BE. BE activity of the modified BE may preferably be equal to or more powerful than that before being modified. In the modified BE, the substitution, deletion, addition, and/or insertion of amino acid residues may occur at the amino-terminal or carboxy-terminal position or any other positions, and the modified amino acid residues may be present one by one in a scattered manner or a few ones of the modified amino acid residues may be present in succession.

BE may be obtained by culturing bacteria that produce this enzyme or may be produced by a genetic engineering approach since the amino acid sequence and base sequence of BE are the known facts. For example, the following literatures report the methods for cloning the base sequence that codes *Aquifex aeolicus* VF5-derived native BE; Takata, H. et al., J. Appl. Glycosci., 2003.50, p. 15-20, and van der Maarel, M. J. E. C. et al., Biocatalysis and Biotransformation, 2003, Vol. 21, p. 199-207. Further, the following literatures report the methods for cloning *Rhodothermus obamensis* JCM 9785-derived native BE; Shinohara, M. L. et al., Appl. Microbiol. Biotechnol., 2001.57(5-6), p. 653-9, and Japanese Translation of PCT International Application Publication No. JP 2002-539822. BE according to the present invention may be selected from the commercial BE products.

4-α-glucanotransferase

4-α-glucanotransferase is an enzyme that transfers glucosyl or a unit of two or more glucoses from the non-reducing end of a donor molecule to the non-reducing end of an acceptor molecule. Possible candidates of 4-α-glucanotransferase used in the present invention may include enzyme entries EC 2.4.1.19 and EC 2.4.1.25 determined by the International Union of Biochemistry and Molecular Biology. The enzyme of the entry EC 2.4.1.25 (hereinafter, may be referred to as MalQ) is termed as amylomaltase, disproportionating enzyme, D-enzyme, or disproportionation enzyme. Microorganism MalQ is termed as amylomaltase, and plant MalQ is termed as D-enzyme. The enzyme of the entry EC 2.4.1.19 (hereinafter, may be referred to as CGTase) is termed as cyclodextrin glucanotransferase, which recognizes 6 to 8 glucose chains at the non-reducing end of a donor molecule and performs such a transfer reaction that circularize the relevant moiety so as to generate non-cyclic limit dextrin and cyclodextrin having a degree of polymerization of 6 to 8.

When 4-α-glucanotransferase is desirably MalQ, either one of amylomaltase and D-enzyme may be used. MalQ used in the present invention may be an enzyme, termed as glycogen debranching enzyme, which have both of 4-α-glucanotransferase activity and amylo-1,6-glucosidase activity (EC 3.2.1.33+EC 2.4.1.25).

When 4-α-glucanotransferase is desirably MalQ, either one of microorganism MalQ or plant MalQ may be used. Examples of the microorganism MalQ may include *Aquifex aeolicus, Streptococcus pneumoniae, Clostridium butylicum, Deinococcus radiodurans, Haemophilus influenzae, Mycobacterium tuberculosis, Thermococcus litralis, Thermotoga maritima, Thermotoga neapolitana, Chlamydia psittaci, Pyrococcus* sp., *Dictyoglomus thermophilum, Borrelia burgdorferi, Synechosystis* sp., *Escherichia coli, Saccharomyces cerevisiae, Thermus aquaticus*, and *Thermus thermophilus*. The plant MalQ may be acquired from tubers including potatoes, sweet potatoes, yams, cassava, cereals including corns, rice plants, and wheat, and beans including peas and soy beans. Of these examples, *Thermus aquaticus* may preferably be used.

When 4-α-glucanotransferase is desirably CGTase, for example, it may be selected 4-α-glucanotransferase derived from microorganism such as *Bacillus stearothrmophilus, Bacillus macerans*, or *Alkalophilic Bacillus* sp. A2-5a (FERM P-13864).

4-α-glucanotransferase activity is measured according to a method described below. In case MalQ is used, 120 μl of a reaction solution containing 10 w/v % maltotriose, 50 mM sodium acetate buffer solution, and an enzyme is incubated at 70° C. for 10 minutes and then heated at 100° C. for 10 minutes, and the reaction is terminated. Then, the amount of glucose in the reaction solution is measured by the glucose oxidase method. As for the unit amount of MalQ, 4-α-glucanotransferase activity of producing 1 μmol of glucose per minute is defined as 1 unit (or U). In CGTase is used, the amount of glucose is measured by Blue value method. Specifically, 250 μl of a reaction solution containing 1.2 w/v % soluble starch, 50 mM acetic acid buffer, and an enzyme is incubated at 40° C. for 10 minutes, and 500 μl of a solution that terminates the reaction (0.5 N acetic acid:0.5 N hydrochloric acid=5:1) is added to and stirred with the reaction solution. After the reaction is terminated, 5 ml of an 12 solution is added to 100 μl of the reaction solution, and the absorbance at 660 nm (A660) is measured. As for the unit amount of CGTase, 4-α-glucanotransferase activity of reducing A660 by 10% per minute is defined as 1 unit (or U). The reaction temperature and reaction pH, for example, during the measurement of 4-α-glucanotransferase activity may be suitably adjustable in accordance with the properties of this enzyme.

The optimal reaction temperature of 4-α-glucanotransferase is typically approximately 45° C. to approximately 90° C. The "optimal reaction temperature" described herein is a temperature at which the activity is maximized when 4-α-glucanotransferase activity measuring method is conducted at varying temperatures, with any other conditions remaining unchanged. The optimal reaction temperature of 4-α-glucanotransferase used in the present invention may be higher than or equal to approximately 45° C., preferably higher than or equal to approximately 50° C., more preferably higher than or equal to approximately 55° C., even more preferably higher than or equal to approximately 60° C., or most preferably higher than or equal to approximately 65° C. No particular upper limit is set for the optimal reaction temperature of 4-α-glucanotransferase used in the present invention. For example, the optimal reaction temperature may be lower than or equal to approximately 90° C., lower than or equal to approximately 85° C., lower than or equal to approximately 80° C., or lower than or equal to approximately 75° C.

4-α-glucanotransferase used in the present invention may desirably have 4-α-glucanotransferase activity at a temperature at which this enzyme is acted upon the substrate. In this description, "having 4-α-glucanotransferase activity at a temperature at which this enzyme is acted upon the substrate" means that 4-α-glucanotransferase activity is observed when measured under the same conditions as in the described 4-α-glucanotransferase activity measuring method, except for 10-minute incubation at the temperature at which this enzyme is acted upon the substrate instead of 10-minute incubation at 70° C. 4-α-glucanotransferase activity at the temperature at which this enzyme is acted upon the substrate may be greater than or equal to approximately 1 U/mL, preferably greater than or equal to approximately 2 U/mL, more preferably greater than or equal to approximately 5 U/mL, even more preferably greater than or equal to approximately 10 U/mL, or most preferably greater than or equal to approximately 20 U/mL. 4-α-glucanotransferase activity at the temperature at which this enzyme is acted upon the substrate may preferably be higher, the upper limit of which is not particularly limited. For example, 4-α-glucanotransferase activity at a temperature at which this enzyme is acted upon the substrate may be less than or equal to 5,000 U/mL, less than or equal to 2,000 U/mL, less than or equal to 1,000 U/mL, less than or equal to 500 U/mL, or less than or equal to 250 U/mL.

4-α-glucanotransferase used in the present invention may be modified 4-α-glucanotransferase in which one or two or more amino acid residues are substituted with, deleted from, added to, and/or inserted in the amino acid sequence of wild-type 4-α-glucanotransferase. 4-α-glucanotransferase activity of the modified 4-α-glucanotransferase may preferably be equal to or more powerful than that before being modified. In the modified 4-α-glucanotransferase, the substitution, deletion, addition, and/or insertion of amino acid residues may occur at the amino-terminal or carboxy-terminal position or any other positions, and the modified amino acid residues may be present one by one in a scattered manner or a few ones of the modified amino acid residues may be present in succession.

4-α-glucanotransferase may be isolated from microorganisms or plants that produce this enzyme or may be produced by a genetic engineering approach since its amino acid sequence and base sequence are the known facts.

The present invention may use a commercially available product of 4-α-glucanotransferase. Examples of a commercial CGTase product include *Bacillus stearothrmophilus* CGTase (available from, for example, Hayashibara Biochemical Laboratories, Inc., Okayama, Japan), and *Bacillus macerans* CGTase (available from, for example, Amano Enzyme Inc., sold under the trade name of Konchizyme), one of which may be selected and used.

3-1-3. Enzymatic Reaction

In the first method, 100 to 4,000 U/g substrate of BE and 4-α-glucanotransferase are reacted with a branched glucan as substrate all at once or stepwise in any order, and the reaction is terminated at a point in time after the high molecular weight glucan according to the present invention is produced.

Prior to the enzymatic reaction in the first method, a substrate solution is prepared. When a solid starch is used as substrate to prepare the substrate solution, the starch may be gelatinized by heating, or BE may be added to the starch before being gelatinized and this starch-BE mixture may be heated to a higher temperature to gelatinize the starch. Otherwise, the starch-liquefied solution obtained by, for example, a typical liquefying step using α-amylase may be used as substrate. BE and 4-α-glucanotransferase may preferably be used for the enzymatic reaction after the starch-liquefied solution (substrate solution) cooled to a lower temperature suitable.

The starch gelatinization start temperature can be measured by an amylograph. A method for measuring the starch gelatinization start temperature is recited on pages 194 to 197 of "Starch Science Encyclopedia" (edited by Fuwa et al., published by Asakura Publishing Co., Ltd., 2003).

Enzymes used for the enzymatic reaction in the first method are BE and 4-α-glucanotransferase adjusted the predetermined concentration. 4-α-glucanotransferase used in this method may be either one of MalQ or CGTase, or both of them may be used.

As for timings of adding the enzymes to be reacted with the substrate in the first method, the following manners 1 to 5 are suggested.

Manner 1: Add BE and 4-α-glucanotransferase both at the same time.

Manner 2: First, add 4-α-glucanotransferase alone, and then add BE at a point in time after the reaction of 4-α-glucanotransferase is progressed to a certain extent.

Manner 3: First, add BE alone, and then add 4-α-glucanotransferase at a point in time after the reaction of BE is progressed to a certain extent.

Manner 4: First, add 4-α-glucanotransferase alone, inactivate this enzyme at a point in time after the reaction is progressed to a certain extent, and then add BE.

Manner 5: First, add BE alone, inactivate this enzyme at a point in time after the reaction is progressed to a certain extent, and then add 4-α-glucanotransferase.

In any one of the manners 1 to 5, if necessary, at least one of the BE and 4-α-glucanotransferase may be added again at a point in time after the reaction(s) is progressed to a certain extent.

It is contemplated that, when BE and 4-α-glucanotransferase at predetermined concentrations are both reacted with the substrate at once as in the manner 1, the division into clusters and the transfer of glucan chains occur at the same time. When BE and 4-α-glucanotransferase are reacted with the substrate at once, the disproportionation reaction of 4-α-glucanotransferase may form a reaction site for BE reaction, thereby causing the transfer of glucan chains in the branched moiety. This may lead to synergetic catalysis of the branching reaction.

When 4-α-glucanotransferase is first reacted with the substrate as in the manners 2 and 4, the branched glucan may be divided into clusters of approximately 30,000 to 500,000 molecular weights, and the disproportionation reaction is considered to form long sugar chains and short sugar chains. Then, the reaction further progresses after BE of a predetermined concentration is added, which is considered to invite the transfer of glucan chains in the branched moiety and accordingly increase the branch frequency in the high molecular weight glucan to be obtained.

BE of a predetermined concentration first reacted with the substrate, as in the manners 3 and 5, is considered to invite the division into clusters and the transfer of glucan chains in the branched moiety. Then, the reaction of 4-α-glucanotransferase added later is considered to lead to the disproportionate reaction, which increases short chain lengths and long chain lengths.

The substrate concentration when the reaction is initiated may be suitably decided and set in accordance with the type of the substrate used. For example, the substrate concentration may be greater than or equal to approximately 50 g/l, preferably greater than or equal to approximately 100 g/l, or more preferably greater than or equal to approximately 150 g/l. The possible highest concentration of the substrate when the reaction is initiated may be suitably decided and set to an extent that the solution's viscosity is not alarmingly high. For example, the substrate concentration may be less than or equal to approximately 300 g/l, preferably less than or equal to approximately 250 g/l, or preferably less than or equal to approximately 200 g/l. The substrate concentration when the reaction is initiated may specifically range from 50 to 300 g/l, preferably from 100 to 250 g/l, or more preferably from 150 to 200 g/l.

The addition amount of BE is set to a value in the range of 100 to 4,000 U/g substrate. When BE is added in any amount of less than 100 U/g substrate, the reaction may not progress, and the action of such an inadequate amount of BE may fail to produce structural differences to the original substrate. Though the synergetic effect by combined use of BE and 4-α-glucanotransferase may provide a high molecular weight glucan structurally different to but somewhat close to the high molecular weight glucan according to the present invention, the obtained high molecular weight glucan may be digested faster than the desirable high molecular weight glucan with slow digestion. When BE is added in any amount of more than 4,000 U/g substrate, on the other hand, the synergetic effect by combined use of BE and 4-α-glucanotransferase may result in more short sugar chains and a higher branch frequency. This may lead to a higher content of indigestible components and fail to obtain the high molecular weight glucan according to the present invention. In view of more efficient production of the high molecular weight glucan according to the present invention, the amount of BE to be added may preferably be 150 to 3,000 U/g substrate or may more preferably be 200 to 2,000 U/g substrate.

The amount of 4-α-glucanotransferase to be added may be suitably decided and set in view of, for example, the type, reaction time, and reaction temperature of 4-α-glucanotransferase used then.

In case MalQ is solely used as 4-α-glucanotransferase, the amount of MalQ relative to the substrate in the solution when the reaction is initiated may be typically greater than or equal to 0.25 U/g substrate, preferably greater than or equal to 0.3 U/g substrate, or more preferably greater than or equal to 0.5 U/g substrate. The upper-limit amount of MalQ solely used may be suitably decided and set to an extent that the high molecular weight glucan according to the present invention is successfully synthesizable. The amount of MalQ may be typically less than or equal to approximately 50 U/g substrate, preferably less than or equal to approximately 10 U/g substrate, or more preferably less than or equal to approximately 1 U/g substrate. The amount of MalQ solely used may specifically range from 0.25 to 50 U/g substrate, preferably from 0.3 to 10 U/g substrate, or more preferably from 0.5 to 1 U/g substrate. The disproportionation reaction may be insufficient with less than 0.1 U/g substrate of MalQ, failing to achieve the synergetic effect expected when used with BE. On the other hand, the disproportionation reaction may overly progress with more than 50 U/g substrate of MalQ. In either case, the high molecular weight glucan according to the present invention may be difficult or impossible to obtain. Another problem with MalQ used in excess may be the formation of a polymer precipitate.

In case CGTase is solely used as 4-α-glucanotransferase, the amount of CGTase relative to the substrate in the solution when the reaction is initiated may be typically greater than or equal to 10 U/g substrate, preferably greater than or equal to 25 U/g substrate, or more preferably greater than or equal to 50 U/g substrate. The upper-limit amount of CGTase solely used may be suitably decided and set to an extent that the high molecular weight glucan according to the present invention is successfully synthesizable. The amount of CGTase may be typically less than or equal to 500 U/g substrate, preferably less than or equal to 250 U/g substrate, or more preferably less than or equal to 100 U/g substrate. The amount of CGTase solely used may specifically range from 10 to 500 U/g substrate, preferably from 25 to 250 U/g substrate, or more preferably from 50 to 100 U/g substrate. The disproportionation reaction may be insufficient with less than 10 U/g substrate of CGTase, failing to achieve the synergetic effect expected when used with BE. With more than 500 U/g substrate of CGTase, on the other hand, the disproportionation reaction may overly progress or cyclodextrin may be abundantly produced. In either case, the high molecular weight glucan according to the present invention may be difficult or impossible to obtain. Another problem with CGTase used in excess may be the formation of a polymer precipitate.

In case MalQ and CGTase are jointly used as 4-α-glucanotransferase, the amounts of these enzymes may be reduced as compared with when they are each solely used. The amounts of these enzymes to be added when they are jointly used may be specifically defined such that, when "MalQ % enzyme amount X" and "CGTase % enzyme amount Y" are summed, an obtained total value (X+Y) is greater than or equal to 100, preferably 100 to 5,000, more preferably 100 to 1,000, or even more preferably 100 to 500.

$$\text{MalQ \% enzyme amount } X = [x(\text{U/g substrate})/0.25 \ (\text{U/g substrate})] \times 100, \quad \text{Formula 7:}$$

where
x is the amount of MalQ used (U/g substrate), 0.25 is the reference amount of MalQ (=lower-limit value when MalQ is solely used)(U/g substrate).

$$\text{GTase \% enzyme amount } Y = [y(\text{U/g substrate})/10 \ (\text{U/g substrate})] \times 100,$$

where
y is the amount of CGTase used (U/g substrate), 10 is the reference amount of CGTase (=lower-limit value when CGTase is solely used)(U/g substrate).

In the case of 0.2 U/g substrate of MalQ and 5 U/G substrate of CGTase, for example, the MalQ % enzyme amount is 80, the CGTase % enzyme amount is 50, and the total value (X+Y) is 130.

The solution in which the enzymatic reaction is prompted (reaction solution) may include an optional buffer agent, if necessary, with an aim to adjust pH, on the condition that such an additional agent does not undermine the enzymatic reaction. The reaction solution pH, though adjustable to any value that allows the enzyme used then to maximize its activity, may preferably be close to the optimal pH value of the enzyme used then. When BE and 4-α-glucanotransferase are reacted in stepwise as described in the manners 2 to 5, the reaction solution pH may be adjusted to a value appropriate for BE when BE is reacted and adjusted to a value appropriate for 4-α-glucanotransferase when 4-α-glucanotransferase is reacted. The reaction solution pH may be typically greater than or equal to approximately 2, preferably greater than or equal to approximately 3, more preferably greater than or equal to approximately 4, even more preferably greater than or equal to approximately 5, particularly preferably greater than or equal to approximately 6, or most preferably greater than or equal to approximately 7. The upper-limit pH of the reaction solution may be decided and set suitably for properties of the enzyme used then. For example, the reaction solution pH may be typically less than or equal to approximately 13, preferably less than or equal to approximately 12, more preferably less than or equal to approximately 11, even more preferably less than or equal to approximately 10, particularly preferably less than or equal to approximately 9, or most preferably less than or equal to approximately 8. The reaction solution pH may be specifically in the range of 3, preferably in the range of +2, more preferably in the range of +1, or even more preferably in the range of +0.5 from the optimal pH of the enzyme used then.

The reaction temperature during the enzymatic reaction may be set to a suitable degree to an extent that each enzyme exerts its desirable activity. The reaction temperature may be, for example, higher than or equal to approximately 30° C., preferably higher than or equal to approximately 40° C., more preferably higher than or equal to approximately 50° C., even more preferably higher than or equal to approximately 55° C., particularly preferably higher than or equal to approximately 60° C., or most preferably higher than or equal to approximately 65° C. The possible highest reaction temperature may be optionally set unless any one of the enzymes is inactivated. For example, the reaction temperature may be lower than or equal to approximately 150° C., lower than or equal to approximately 140° C., lower than or equal to approximately 130° C., lower than or equal to approximately 120° C., lower than or equal to approximately 110° C., or lower than or equal to approximately 100° C. The reaction temperature may preferably be lower than or equal to approximately 90° C., more preferably lower than or equal to approximately 85° C., even more preferably lower than or equal to approximately 80° C., particularly preferably lower than or equal to approximately 75° C., or most preferably lower than or equal to approximately 70° C. The range of degrees of the reaction temperature may be, for example, approximately 30° C. to approximately 150° C., preferably approximately 40° C. to approximately 90° C., more preferably approximately 50° C. to approximately 85° C., even more preferably approximately 55° C. to approximately 80° C., particularly preferably approximately 60° C. to approximately 75° C., or most preferably approximately 65° C. to approximately 70° C. The reaction temperature may be regulated by any suitable one of the known heating means. The reaction solution may preferably be stirred while being heated, so that heat being applied is evenly transmitted to the whole solution.

When the reaction time set for the enzymatic reaction is too short, the high molecular weight glucan according to the present invention is possibly not obtainable. On the other hand, the enzymatic reaction, if continued over an extended period of time, becomes steady, ensuring successful production of the high molecular weight glucan pursued by the present invention. This, however, should be avoided because longer reaction time increases production costs. The enzymatic reaction, therefore, is desirably ended at an appropriate stage soon after the high molecular weight glucan according to the present invention is produced. The reaction time set for the enzymatic reaction may be adjusted in view of the type and amount of the substrate, the type and amount, reaction temperature, and remaining enzymatic activity of the enzyme used then, and timing to add the enzyme.

Examples of the reaction time in the manner 1 after the addition of BE and 4-α-glucanotransferase both to the reaction solution may include 1 hour or more, preferably 2 hours or more, more preferably 5 hours or more, even more preferably 10 hours or more, or most preferably 24 hours or more. While any particular upper limit is not necessarily set for the reaction time, for example, 100 hours or less, preferably 72 hours or less, more preferably 48 hours or less, or even more preferably 36 hours or less may be set as the reaction time. The reaction time may be specifically 1 to 100 hours, preferably 5 to 72 hours, more preferably 10 to 48 hours, or even more preferably 24 to 36 hours.

Examples of the reaction time in the manner 2 after the addition of 4-α-glucanotransferase and before the addition of BE to the reaction solution may include 0.5 hours or more, preferably 0.75 hours or more, more preferably 1 hour or more, or even more preferably 2 hours or more. While any particular upper limit is not necessarily set for the reaction time, for example, 24 hours or less, preferably 12 hours or less, more preferably 8 hours or less, or even more preferably 4 hours or less may be set as the reaction time. The reaction time may be specifically 0.5 to 24 hours, preferably 0.75 to 12 hours, more preferably 1 to 8 hours, or even more preferably 2 to 4 hours.

Examples of the reaction time in the manner 2 after the addition of BE to the reaction solution may include 1 hour or more, preferably 5 hours or more, more preferably 10 hours or more, or even more preferably 24 hours or more. While any particular upper limit is not necessarily set for the reaction time, for example, 100 hours or less, preferably 72 hours or less, more preferably 48 hours or less, or even more preferably 36 hours or less may be set as the reaction time. The reaction time may be specifically 1 to 100 hours, preferably 5 to 72 hours, more preferably 10 to 48 hours, or even more preferably 24 to 36 hours.

Examples of the reaction time in the manner 3 after the addition of BE and before the addition of 4-α-glucanotransferase to the reaction solution may include 0.5 hours or more, preferably 0.75 hours or more, more preferably 1 hour or more, or even more preferably 2 hours or more. While any particular upper limit is not necessarily set for the reaction time, for example, 24 hours or less, preferably 12 hours or less, more preferably 8 hours or less, or even more preferably 4 hours or less may be set as the reaction time. The reaction time may be specifically 0.5 to 24 hours, preferably 0.75 to 12 hours, more preferably 1 to 8 hours, or even more preferably 2 to 4 hours.

Examples of the reaction time in the manner 3 after the addition of 4-α-glucanotransferase to the reaction solution may include 1 hour or more, preferably 5 hours or more, more preferably 10 hours or more, or even more preferably 24 hours or more. While any particular upper limit is not necessarily set for the reaction time, for example, 100 hours or less, preferably 72 hours or less, more preferably 48 hours or less, or even more preferably 36 hours or less may be set as the reaction time. The reaction time may be specifically 1 to 100 hours, preferably 5 to 72 hours, more preferably 10 to 48 hours, or even more preferably 24 to 36 hours.

Examples of the reaction time in the manner 4 before the enzyme inactivation starts after the addition of 4-α-glucanotransferase to the reaction solution may include 1 hour or more, preferably 4 hours or more, more preferably 12 hours or more, or even more preferably 24 hours or more. While any particular upper limit is not necessarily set for the reaction time, for example, 72 hours or less, preferably 60 hours or less, more preferably 48 hours or less, or even more preferably 36 hours or less may be set as the reaction time. The reaction time may be specifically 1 to 72 hours, preferably 4 to 60 hours, more preferably 12 to 48 hours, or even more preferably 24 to 36 hours.

Examples of the reaction time in the manner 4 after the addition of BE to the reaction solution may include 1 hour or more, preferably 5 hours or more, more preferably 10 hours or more, or even more preferably 24 hours or more. While any particular upper limit is not necessarily set for the reaction time, for example, 100 hours or less, preferably 72 hours or less, more preferably 48 hours or less, or even more preferably 36 hours or less may be set as the reaction time. The reaction time may be specifically 1 to 100 hours, preferably 5 to 72 hours, more preferably 10 to 48 hours, or even more preferably 24 to 36 hours.

Examples of the reaction time in the manner 5 before the enzyme inactivation starts after the addition of 4-α-glucanotransferase to the reaction solution may include 1 hour or more, preferably 4 hours or more, more preferably 12 hours or more, or even more preferably 24 hours or more. While any particular upper limit is not necessarily set for the reaction time, for example, 72 hours or less, preferably 60 hours or less, more preferably 48 hours or less, or even more preferably 36 hours or less may be set as the reaction time. The reaction time may be specifically 1 to 72 hours, preferably 4 to 60 hours, more preferably 12 to 48 hours, or even more preferably 24 to 36 hours.

Examples of the reaction time in the manner 5 after the addition of BE to the reaction solution may include 1 hour or more, preferably 5 hours or more, more preferably 10 hours or more, or even more preferably 24 hours or more. While any particular upper limit is not necessarily set for the reaction time, for example, 100 hours or less, preferably 72 hours or less, more preferably 48 hours or less, or even more preferably 36 hours or less may be set as the reaction time. The reaction time may be specifically 1 to 100 hours, preferably 5 to 72 hours, more preferably 10 to 48 hours, or even more preferably 24 to 36 hours.

When, as in the manner 1, BE and 4-α-glucanotransferase are added and reacted at once in the reaction solution and the substrate used then is starch granules, for example, a mixture containing BE, 4-α-glucanotransferase, and starch granules is prepared at a temperature lower than a temperature at which the starch granules start to be gelatinized, and the mixture is kept at the temperature or elevated to a temperature lower than the starch gelatinizing-start temperature, higher than the mixture-preparing temperature, and high enough to allow BE and 4-α-glucanotransferase to advance their reactions (hereinafter, may be referred to as embodiment A). The temperature at which the starch granules start to be gelatinized may differ with a plant from which the starch granules used are obtained, its harvest time, and location of its plantation. Starches listed below start to be gelatinized at the following temperatures, typical corn starch: approximately 70.7° C., waxy corn starch (sticky corn): approximately 67.5° C., rice starch: approximately 73.5° C., potato starch: approximately 62.6° C., tapioca starch: approximately 68.4° C., mung bean starch: approximately 71.0° C.

In the embodiment A, the temperature lower than the gelatinizing-start temperature at which the mixture containing BE, 4-α-glucanotransferase, and starch granules is prepared may be suitably decided and set in accordance with the starch granules used then. For example, the mixture-preparing temperature may be higher than or equal to approximately 0° C., preferably higher than or equal to approximately 10° C., more preferably higher than or equal to approximately 15° C., even more preferably higher than or equal to approximately 20° C., or most preferably higher than or equal to approximately 25° C. The possible highest temperature at which the mixture is prepared is also not particularly limited unless it is higher than the starch gelatinizing-start temperature. For example, the mixture-preparing temperature may be lower than or equal to approximately 67.5° C., preferably lower than or equal to approximately 60° C., more preferably lower than or equal to approximately 50° C., even more preferably lower than or equal to approximately 40° C., or most preferably lower than or equal to approximately 35° C. The mixture-preparing temperature may specifically range from approximately 0 to approximately 67.5° C., preferably from approximately 10 to approximately 60° C., more preferably from approximately 15 to approximately 50° C., even more preferably from approximately 20 to approximately 40° C., or most preferably from approximately 25 to approximately 35° C.

In the embodiment A, the temperature high enough to allow the enzyme advance its reaction (i.e., temperature lower than the starch gelatinizing-start temperature and higher than the mixture-preparing temperature) may be suitably decided and set in accordance with the optimal reaction temperature of the enzyme used then. For example, the temperature at which the enzymatic reaction is progressed may be higher than or equal to approximately 30° C., preferably higher than or equal to approximately 35° C., more preferably higher than or equal to approximately 40° C., even more preferably higher than or equal to approximately 45° C., or most preferably higher than or equal to approximately 50° C. The possible highest temperature that allows the enzyme to advance its reaction may be suitable decided and set in accordance with properties of the enzyme used then. For example, the upper-limit temperature may be lower than or equal to approximately 80° C., lower than or equal to approximately 75° C., lower than or equal to approximately 70° C., lower than or equal to approximately 65° C., lower than or equal to approximately 60° C., lower than or equal to approximately 55° C., or lower than or equal to approximately 50° C. The temperature at which the enzymatic reaction is progressed may specifically range from approximately 30 to approximately 80° C., preferably from approximately 35 to approximately 75° C., more preferably from approximately 40 to approximately 75° C., even more preferably from approximately 45 to approximately 75° C., or most preferably from approximately 50 to approximately 75° C. This reaction temperature may be kept at a certain temperature or may be gradually elevated to higher degrees.

The enzymatic reaction may be performed by any suitable one of the known enzymatic reaction devices, for example, a known stainless steel reaction tank equipped with a hot water jacket and a stirring device.

After the high molecular weight glucan according to the invention is produced through the enzymatic reaction, the reaction solution, if necessary, may be heated at approximately 100° C. for 60 minutes to inactivate the enzymes in the reaction solution. The reaction solution may be stored without the enzymes being inactivated or may be handled in a purifying process of the high molecular weight glucan according to the invention.

3-1-4. Purifying Process

The high molecular weight glucan according to the invention produced through the enzymatic reaction may be subjected to a purifying process, if necessary. Examples of impurity removed in the purifying process may include BE, 4-α-glucanotransferase, low molecular weight glucan possibly produced as bi-product, and inorganic salts.

For purification of the high molecular weight glucan according to the invention may be used an organic solvent-used precipitation method (T. J. Schoch et al., J. American Chemical Society, 64, 2957 (1942)). Examples of the organic solvent usable in the purification method may include acetone, n-amylalcohol, pentazole, n-propylalcohol, n-hexylalcohol, 2-ethyl-1-butanol, 2-ethyl-1-hexanol, lauryl alcohol, cyclohexahol, n-butyl alcohol, 3-pentanol, 4-methyl-2-pentanol, d, 1-borneol, α-terpineol, isobutyl alcohol, sec-butyl alcohol, 2-methyl-1-butanol, isoamyl alcohol, tert-amyl alcohol, menthol, methanol, ethanol, and ether.

To purify the high molecular weight glucan according to the present invention, the high molecular weight glucan dissolved in water may be directly subjected to a separation treatment, instead of being precipitated, to remove the impurity such as BE, 4-α-glucanotransferase, low molecular weight glucan possibly produced as bi-product, and inorganic salts. Examples of the separation treatment may include chromatography, and membrane fractionation using ultrafilter membrane. The ultrafilter membrane usable in the purifying process may be selected from ultrafilter membranes with molecular cutoff of approximately $1\times10^3$ to $1\times10^4$, preferably approximately $5\times10^3$ to $5\times10^4$, or more preferably approximately $1\times10^4$ to $3\times10^4$ (for example, "UF membrane unit" available from Daicel Corporation). A carrier that may be used in chromatography may be selected from, for example, carries respectively for gel filtration chromatography, ligand exchange chromatography, ion exchange chromatography, and hydrophobic chromatography.

3-2. Second Method

3-2-1. Substrate

The substrate used in the second method is also the branched glucan. Suitable examples of the substrate used in the second method are similar to those described in the first method.

3-2-2. Enzyme

Branching Enzyme (BE)

The properties and possible origins of BE used in the second method are similar to those described in the first method.

Exo-Type Amylase

β-amylase is an exo-type amylase that sequentially hydrolyzes α-1,4-glucoside bonds per maltose from non-reducing ends.

The exo-type amylase used in the present invention may be any one selected from, for example, β-amylase, glucoamylase, and α-glucosidase. A preferable exo-type amylase among these examples is one not having the hydrolytic activity of α-1,6-glucoside bonds or one less active in hydrolyzing α-1,6-glucoside bonds, and a more preferable one is β-amylase, glucoamylase not having the hydrolytic activity of α-1,6-glucoside bonds, or α-glucosidase not having the hydrolytic activity of α-1,6-glucoside bonds. The most preferable exo-type amylase is β-amylase.

The origin of the exo-type amylase used in the present invention is not particularly limited. The exo-type amylase may be derived from any one of plants including wheat, barley, soybeans, and sweet potatoes, bacteria, and fungi.

In the present invention, a unit (or U) amount of β-amylase indicates an amount of enzyme that produces 1 μmol of maltose in one minute from a soluble starch, and a unit (or U) amount of glucoamylase indicates an amount of enzyme that produces 10 mg of glucose in 30 minutes from a soluble starch. Further, a unit (or U) amount of α-glucosidase indicates an amount of enzyme that liberates 1 μmol of 4-nitrophenol in one minute from p-nitrophenyl-α-D-glucopyranoside.

The optimal reaction temperature of the exo-type amylase may differ with its origin. For example, β-amylase derived from sweet potatoes may have an optimal reaction temperature of approximately 60° C. to 70° C. The "optimal reaction temperature" means a temperature at which the activity is maximized when the described exo-amylase activity measuring method is conducted at varying temperatures, with any other conditions remaining unchanged. The soybean-derived exo-type amylase used in the present invention may preferably have an optimal reaction temperature higher than or equal to approximately 30° C., more preferably higher than or equal to approximately 35° C., even more preferably higher than or equal to approximately 37° C., particularly preferably higher than or equal to approximately 40° C., or most preferably higher than or equal to approximately 45° C. The possible highest optimal reaction temperature of the exo-type amylase used in the present invention is also not particularly limited. For example, the optimal reaction temperature may be lower than or equal to approximately 65° C., lower than or equal to approximately 60° C., lower than or equal to approximately 55° C., or lower than or equal to approximately 50° C.

Exo-type amylase used in the present invention may be a modified enzyme in which one or two or more amino acid residues are substituted with, deleted from, added to, and/or inserted in the amino acid sequence of wild-type, exo-type amylase. Exo-type amylase activity of the modified exo-type amylase may preferably be equal to or more powerful than that before being modified. In the modified exo-type amylase, the substitution, deletion, addition, and/or insertion of amino acid residues may occur at the amino-terminal or carboxy-terminal position or any other positions, and the modified amino acid residues may be present one by one in a scattered manner or a few ones of the modified amino acid residues may be present in succession.

Exo-type amylase may be isolated from plants, bacteria, or fungi that produce this enzyme or may be produced by a genetic engineering approach since its amino acid sequence and base sequence are the known facts.

There are commercial products of exo-type amylase, for example, soybean-derived β-amylase (β-amylase #1500, available from Nagase ChemteX Corporation). Any suitable one of these commercially produced β-amylase products may be used in the present invention.

3-2-3. Enzymatic Reaction

The second method makes 100 to 4,000 U/g substrate of branching enzyme react with the branched glucan as substrate, and then makes exo-type amylase react with the branched glucan, and then terminates the reaction at a point in time after the high molecular weight glucan according to the present invention is produced.

The second method starts with preparing a substrate solution subjected to the enzymatic reaction. The substrate solution may be prepared in a manner similar to the first method.

Enzymes used for the enzymatic reaction according to the second method are BE and exo-type amylase at the predetermined concentration. As for timings of adding the enzymes to be reacted with the substrate in the second method, the following manners I and II are suggested.

Manner I: First, add BE alone, and then add exo-type amylase at a point in time after the reaction of BE is progressed to a certain extent.

Manner II: First, add BE alone, inactivate this enzyme at a point in time after the reaction is progressed to a certain extent, and then add exo-type amylase.

Of the manners I and II, the manner II may preferably be employed in view of more efficient production of the high molecular weight glucan according to the present invention.

In either one of the manners I and II, if necessary, at least one of BE and exo-type amylase may be added again at a point in time after the reaction(s) is progressed to a certain extent.

It is contemplated that the division into clusters and the transfer of glucan chains in the branched moiety both occur when BE is first reacted with the substrate as in the manners I and II, and shorter chain lengths increase when exo-type amylase is later reacted with the substrate.

The substrate concentration when the reaction is initiated may be suitably decided and set in accordance with the type of the substrate used then. Possible specific ranges of the substrate concentration in this method are similar to those suggested in the description of the first method.

The amount of BE to be added is also similar to that of the first method.

The amount of exo-type amylase to be added may be suitably decided and set in view of the type, reaction time, and reaction temperature of exo-type amylase used then. For example, the amount of exo-type amylase, relative to the amount of substrate in the solution when the reaction starts, may be typically greater than or equal to approximately 0.5 U/g substrate, preferably greater than or equal to approximately 1.0 U/g substrate, or more preferably greater than or equal to approximately 1.5 U/g substrate. The largest amount of exo-type amylase to be added may be suitably decided and set to an extent that the high molecular weight glucan according to the present invention is synthesizable, for example, typically less than or equal to approximately 150 U/g substrate, preferably less than or equal to approximately 75 U/g substrate, or more preferably less than or equal to approximately 15 U/g substrate. The amount of exo-type amylase to be added may specifically range from approximately 0.5 to 150 U/g substrate, preferably from approximately 1.0 to 75 U/g substrate, or more preferably from approximately 1.5 to 15 U/g substrate. Less than approximately 0.5 U/g substrate of the exo-type amylase may be inadequate to fully hydrolyze the substrate, failing to obtain the high molecular weight glucan according to the present invention. On the other hand, more than approximately 150 U/g substrate of exo-type amylase may lead to excessive hydrolysis of the substrate, similarly failing to obtain the high molecular weight glucan according to the present invention.

The solution in which the enzymatic reaction is prompted (reaction solution) may include an optional buffer agent, if necessary, with an aim to adjust pH, on the condition that such an additional agent does not undermine the enzymatic reaction. The reaction solution pH, though adjustable to any value that allows the enzyme used then to maximize its activity, may preferably be close to the optimal pH value of the enzyme used then. In the second method, pH may be adjusted to a value suitable for the enzyme used then, specifically, pH value suitable for BE when this enzyme is reacted, and pH value suitable for exo-type amylase when this enzyme is reacted. Specific pH ranges of the reaction solution are similar to those described in the first method.

The reaction temperature during the enzymatic reaction may be suitably adjusted within a range of degrees that allow the enzyme used then to exert its desirable activity.

In the manners I and II, the reaction temperature after the addition of BE and before the addition of exo-type amylase may be set to degrees similar to those described in the first method.

The reaction temperatures in the manners I and II after the addition of exo-type amylase may be higher than or equal to approximately 25° C., preferably higher than or equal to approximately 30° C., or more preferably higher than or equal to approximately 35° C. The possible highest reaction temperatures in the manners I and II are also not particularly limited unless the enzymes are inactivated, for example, lower than or equal to approximately 40° C. or preferably lower than or equal to approximately 37° C. The suitable temperature range may be approximately 25° C. to approximately 30° C., preferably approximately 30° C. to approximately 37° C., or more preferably approximately 35° C. to approximately 37° C.

The enzymatic reaction time, if too short, may fail to produce the high molecular weight glucan according to the present invention. On the other hand, the enzymatic reaction, if too long, may also fail to produce the high molecular weight glucan according to the present invention as a result of the substrate being overly hydrolyzed by exo-type amylase. The enzymatic reaction, therefore, is desirably ended at an appropriate stage soon after the high molecular weight glucan according to the present invention is produced. The reaction time set for the enzymatic reaction may be adjusted in view of the type and amount of the substrate, the type and amount, reaction temperature, and remaining enzymatic activity of the enzyme used then, and timing to add the enzyme.

Specifically, the reaction time after the addition of BE and before the addition of exo-type amylase may be 1 hour more, preferably 10 hours or more, more preferably 18 hours or more, or even more preferably 24 hours or more. This reaction time, though its upper limit is not necessarily set, may be, for example, 100 hours or less, preferably 72 hours or less, more preferably 48 hours or less, or even more preferably 36 hours or less. The reaction time may specifically range from 1 to 100 hours, preferably from 10 to 72 hours, more preferably from 18 to 48 hours, or even more preferably from 24 to 36 hours.

The reaction time after the addition of exo-type amylase may be 0.25 hours more, preferably 0.5 hours or more, more preferably 0.75 hours or more, or even more preferably 1 hour or more. This reaction time, though its upper limit is not necessarily set, may be, for example, 2.75 hours or less, preferably 2.25 hours or less, more preferably 2 hours or less, or even more preferably 1.5 hours or less. The reaction time may specifically range from 0.25 to 2.75 hours, preferably from 0.5 to 2.25 hours, more preferably from 0.75 to 2 hours, or even more preferably from 1 to 1.5 hours.

The enzymatic reaction may be performed by any suitable one of the known enzymatic reaction devices, for example, a known stainless steel reaction tank equipped with a hot water jacket and a stirring device.

After the high molecular weight glucan according to the invention is produced by the second method, the reaction solution, if necessary, may be heated at approximately 100° C. for 60 minutes to inactivate the enzymes in the reaction solution. The reaction solution may be stored without the enzymes being inactivated or may be handled in a purifying process of the high molecular weight glucan according to the invention.

3-2-4. Purifying Process

Specifics of the purifying process are similar to those described in the first method.

Working Examples

The present invention is hereinafter described in further detail in working examples illustrated below. The present invention, however, should not be construed as being limited to the working examples.

Referring to an obtained analysis result of unit chain length distribution, "$DP_{X-Y}$" represents an integrated value of peak areas for degrees of polymerization of X to Y, and "$DP_{1-5}$", for example, represents an integrated value of peak areas for degrees of polymerization of 1 to 5.

Referring to the analysis result of unit chain length distribution, "$DP_{X-Y}$ ratio" represents the ratio (%) of an integrated value of peak areas for degrees of polymerization of X to Y to an integrated value of peak areas for degrees of polymerization of 1 to 50, and "$DP_{1-5}$", for example, represents the ratio (%) of an integrated value of peak areas for degrees of polymerization of 1 to 5 to an integrated value of peak areas for degrees of polymerization of 1 to 50.

Referring to the analysis result of unit chain length distribution, "Top peak ratio (%)" represents the ratio (%) of a largest peak area among peak areas for degrees of polymerization of 1 to 50 to an integrated value of peak areas for degrees of polymerization of 1 to 50.

Test Method (1) Molecular Weight Measurement for High Molecular Weight Glucan

The weight-average molecular weight of the high molecular weight glucan was measured by the GPC-MALS method. In the GPC-MALS method, the molecular weight was analyzed with an analyzer in which the following devices are combined; multi-angle light scattering instrument (MALS, available from HELEOS II, WYATT TECHNOLOGY), differential refractive index detector (RID-20A, available from Shimadzu Corporation), and high performance liquid chromatography (HPLC) system (OHPAK SB-804HQ or SB-806M HQ, available from SHOWA DENKO K.K.). The solvent used in the analysis was a 100 mM sodium nitrate aqueous solution. First, 50 mg of a high molecular weight glucan in the form of powder was dissolved in 10 mL of the 100 mM sodium nitrate aqueous solution for sample adjustment. The sample was filtered through a filter having the pore size of 0.45 µm, and 100 µL of the obtained filtrate was injected into the HPLC system.

The multi-angle light scattering instrument is configured to measure the intensity of scattered light (Rayleigh scattering measurement) generated when a sample for measurement is irradiated with light (static light scattering). The intensity of scattered light is associated with the magnitude of molecular weight. Interference increases with larger molecular weights and diminishes with smaller molecular weights, which allows an absolute molecular weight to be measured. A relationship among the intensity of scattered light, scattering angle, and molecular weight is basically expressed by the following formula.

$$\frac{KC}{R(\theta)} = \frac{1}{MwP(\theta)} + 2A_2C, \qquad \text{Formula 8}$$

where $R(\theta)$ is Rayleigh ratio of excess scattering, C is sample concentration (g/mL), Mw is weight-average molecular weight, A2 is second virial coefficient, K (optical parameter)=$(dn/dc)^2$×optical constant, $P(\theta)$ is a function that depends on angle of scattering light, and dn/dc value is index of refraction increment.

The index of refraction depends on a material(s) used, and dn/dc value=0.142 of standard polymer pullulan (available from SHOWA DENKO K.K.) was used in this measurement.

The differential refractive index detector was used to measure the concentrations of sample solutions based on differences in index of refraction of light. The average molecular weight of the sample solutions was calculated from measured values of the sample solution concentration separated by the GPC and of the weight-average molecular weight.

(2) Measurement of Branch Frequency in High Molecular Weight Glucan

The branch frequency in the high molecular weight glucan was calculated by measuring the number of α-1,6-glucoside bonds and the total number of glucose units in molecule. The number of α-1,6-glucoside bonds was calculated as equivalent to the measurement of the non-reducing ends in the glucan. For this measurement of the non-reducing ends, 10 U/mL of *Pseudomonas isoamylase* (available from Megazyme Corporation) was reacted with a 0.25 w/v % high molecular weight glucan at 37° C. for 18 hours in a 20 mM acetic acid buffer (pH 5.5), and a reducing power after the reaction was measured by an altered Park-Johnson method (Hizukuri et al., Starch, Vol., 35, pp. 348-350 (1983)).

The total number of molecular glucose units was obtained by a total sugar amount measurement. Specifically, 10 U/mL of *Pseudomonas isoamylase* (available from Megazyme Corporation), 20 U/mL of bacterial α-amylase (NAGASE & CO., LTD.), and 10 U/mL of *Rhizopus glucoamylase* (available from TOYOBO CO., LTD.) were reacted with a 0.25 w/v % high molecular weight glucan at 37° C. for 18 hours in a 20 mM acetic acid buffer (pH 5.5) until they were fully hydrolyzed to glucose. Then, the amount of glucose was measured by the glucose oxidase method (Glucose CII Test Wako, available from Wako Pure Chemical Corporation).

Then, the branch frequency was calculated by the formula illustrated earlier based on the number of α-1,6-glucoside bonds and the total number of glucose units in molecule.

(3) Measurement of Unit Chain Length Distribution

The linear α-1,4-glucans (unit chain lengths) in molecule of a high molecular weight glucan were separated by length (degree of polymerization) to analyze the concentration distribution of unit chain lengths for different degrees of polymerization. First, 10 U/mL of *Pseudomonas isoamylase* (available from Megazyme Corporation) was reacted with a 0.25 w/v % high molecular weight glucan at 37° C. for 18 hours in a 20 mM acetic acid buffer (pH 5.5) to fully hydrolyze α-1,6-glucocyl bonds of the high molecular weight glucan. Then, the obtained isoamylase-digested product was used to analyze the unit chain length distribution using the HPAEC-PAD method.

The HPAEC-PAD method used an HPAEC-PAD device available from Dionex Corporation (liquid feeding system: DX300, detector: PAD-2, column: Carbo PAC PA100). The conditions for elution were rate of flow: 1 L/min., NaOH concentration: 150 mM, sodium acetate concentration: 0 min.-50 mM, 2 min.-50 mM, 27 min.-350 mM (Gradient curve No. 4), 52 min.-850 mM (Gradient curve No. 8), and 54 min.-850 mM. The programs of Gradient curves No. 4 and No. 8 are preinstalled programs of the Dionex ICS-3000 system.

The obtained unit chain length distribution was analyzed as follows. The ratio of unit chain lengths for different degrees of polymerization in molecule of the high molecular weight glucan was converted based on a total peak area value for degrees of polymerization of 1 to 50 making up 100%. A graphical presentation on which the degree of polymerization and the ratio of unit chain lengths were respectively plotted on lateral axis and vertical axis was used for comparison of the structural features of the high molecular weight glucans in view of the unit chain lengths. Peaks for degrees of polymerization over 50 were substantially not detected in most of the high molecular weight glucan molecules, and any peaks for degrees of polymerization over 50 detected in some high molecular weight glucan molecules were barely the detection limits.

Further, the "slope of 20%-60% cumulative plotting" was calculated based on the obtained unit chain length distribution.

(4) Analysis of High Molecular Weight Glucan End Structure Using Methylation Method The end structure of the high molecular weight glucan was analyzed by a methylation method. The methylation method followed the technique recited in Hakomori's Journal of Biochemistry, 1964, 55(2), p 205-208. In this method, a solution was prepared by adding 1 g of dimethyl sulfoxide (DMSO) to 20 mg of sodium hydroxide. Then, 1 mg of the high molecular weight glucan was put in a test tube, and 500 μL of the prepared solution 200 μL of methyl iodide were added to this solution in the mentioned order, and the resulting solution was stirred for 15 minutes at room temperature to be methylated. Then, water and chloroform were added to the methylated solution, which was subjected to liquid-liquid extraction three times to collect chloroform phase, and the solvent was eliminated with an evaporator. Then, 500 μL of 2 M trifluoroacetic acid was added to the methylated high molecular weight glucan, and this mixture was stirred at 90° C. for one hour to be hydrolyzed. Then, 200 μL of toluene was added to the resulting mixture, from which the solvent was then eliminated with an evaporator. The hydrolyzed mixture was then mixed with 500 μL of a 250 mM hydrogenated sodium borate aqueous solution containing and then stirred overnight at room temperature to induce a reductive reaction. Then, acetic acid was added to the resulting mixture until bubbles came down. This mixture was then mixed with 200 μL of toluene, from which the solvent was then eliminated with an evaporator. Lastly, 200 μL of pyridine and 200 μL of acetic anhydride were added to the mixture, which was stirred for 20 minutes at 90° C. to be acetylated. After the reaction occurred, the resulting solution was mixed with 200 μL of toluene, from which the solvent was then eliminated with an evaporator. Then, water and chloroform were added to the acetylated solution, which was subjected to liquid-liquid extraction three times to collect chloroform phase, and the solvent was eliminated with an evaporator. As a result, partially methylated glucan was obtained.

The partial methylated glucan was analyzed by the gas chromatography-mass spectroscopy analysis. The analysis used GC-MS-QP2010Plus (available from, Shimadzu Corporation), and the column used was DB-225 (available from J&W Scientific, Inc.). The conditions for analysis were carrier gas: helium, column temperature: 170° C. elevated to 210° C. (rate of temperature increase: 3° C./min., vaporizing chamber temperature: 230° C., detector temperature: 230° C. The samples were dissolved in chloroform.

(5) Analysis of the Bonding Mode of High Molecular Weight Glucan Using Enzymatic Method The bonding mode of the high molecular weight glucan was analyzed by an enzymatic method. Isoamylase hydrolyzes α-1,6-glucoside bond, while α-amylase and β-amylase hydrolyze α-1,4-glucoside bond. Isoamylase cannot hydrolyze α-1,6-glucoside bond at a non-reducing end. It was determined by reacting these three different enzymes whether any glucoside bonds but the α-1,4-glucoside bond or α-1,6-glucoside bond were present and whether any non-reducing ends were branched.

First, 10 U/mL of *Pseudomonas isoamylase* (available from Megazyme Corporation) was reacted with a 0.25 w/v % high molecular weight glucan at 37° C. for 18 hours in a 20 mM acetic acid buffer (pH 5.5), and 20 U/mL of bacterial α-amylase (available from Nagase ChemteX Corporation) and 30 U/mL of soybean (β-amylase (available from Nagase ChemteX Corporation) were further reacted with the high molecular weight glucan at 37° C. for 18 hours. The obtained enzyme hydrolyzate was analyzed under the same conditions as in the HPAEC-PAD method described in "3) measurement of unit chain length distribution".

(6) In Vitro Digestibility Test

This digestibility testing used a hydrolysis test designed to imitate in vivo digestion system of carbohydrate. The method proposed by Englyst et al., (European Journal of Clinical Nutrition, 1992, 46S33-S50) was altered and used in this test. Specifically, this method measures over time an amount of glucose hydrolyzed and released by the digestive enzymes (porcine pancreas α-amylase and rat small intestine mucosa enzyme). The digestive enzymes and test materials were prepared as follows. Porcine pancreas α-amylase obtained from Sigma Chemical Co. was suspended in a 50 mM acetic acid buffer (pH 5.5) and prepared into an enzyme solution of 250 U/mL activity. Further, 150 mg of rat small intestine acetone powder obtained from Sigma Chemical Co. was suspended in 3 mL of a 50 mM acetic acid buffer (pH 5.5), and a centrifuge supernatant was obtained as an extract of rat small intestine acetone power, which was used as a rat small intestine mucosa enzyme solution. The high molecular weight glucan to be measured was adjusted to 5 w/v % with distilled water and then heated at 100° C. for five minutes to be fully dissolved. The activity of α-glucosidase included in 50 mg/mL of the rat small intestine acetone power was 0.3 U/mL.

This test was performed according to the following steps. First, 100 µL of an aqueous solution containing a 5 w/v % high molecular weight glucan or some other sample having the same concentration, 20 µL of a 1M acetic acid buffer (pH 5.5), and 716 µL of distilled water were mixed. Then, the respective enzyme solutions (4 µL of α-amylase (1 U/mL) and 160 µL of the rat small intestine enzyme solution (α-glucosidase: 0.05 U/mL) were added to the mixture to start the reaction. The reaction temperature then was set to 37° C., and 100 µL of the reaction solution was collected in 0 minute, 10 minutes, 20 minutes, 30 minutes, 60 minutes, 90 minutes, and 120 minutes after the reaction was initiated. The collected samples were immediately treated at 100° C. for 5 minutes to terminate the reaction. The glucose concentrations of these reaction-termination solutions were quantitatively determined by Glucose CII Test Wako available from Wako Pure Chemical Corporation.

Then, an initial digestion rate coefficient k observed in 30 minutes after the reaction was initiated was calculated from the obtained digestibility test result by using the formula described earlier and Butterworth et al., Logarithm of the slope (LOS) plotting (Carbohydrate Polymers 87 (2012), 2189-2197).

Further, the percentage (%) of the rapid-digestible fractions, slow-digestible fractions and indigestible fractions included in the high molecular weight glucan and other samples were calculated from the obtained digestibility test result by using the formula described earlier.

(7) Measurement of Changes in Blood Glucose Levels and Insulin Levels after Oral Ingestion A crossover open trial was performed on enrolled subjects; healthy adults who fasted (except water) for 10 hours or more. The subjects were orally administered with 50 g of the high molecular weight glucan; test sample, or glucose; control sugar, and their blood glucose levels and blood insulin levels were measured during fasting and also measured in 10 minutes, 20 minutes, 30 minutes, 45 minutes, 60 minutes, 75 minutes, 90 minutes, and 120 minutes after the ingestion.

Enzyme Preparation (1) Production of *Aquifex Aeolicus* BE

An enzyme solution containing *Aquifex aeolicus* BE (AqBE) (AqBE enzyme solution) was obtained by using *E. coli* TG1 strain that holds recombinant plasmid pAQBE1 and according to the method described in the production example 1 of Japanese Patent Laid-open Publication No. 2008-95117.

(2) Production of *Thermus Aquaticus* Amylomaltase

An enzyme solution containing *Thermus aquaticus* amylomaltase (TaqMalQ) (TaqMalQ enzyme solution) was obtained by using *E. coli* MC1061 strain that holds plasmid pFGQ8 described in Terada et al. (Applied and Environmental Microbiology, vol. 65, 910-915 (1999)) and according to the method described in that literature.

(3) CGTase and β-Glucosidase

CGTase (Konchizyme, Amano Enzyme Inc.) and (β-amylase (#1500, available from Nagase ChemteX Corporation) were purchased to prepare enzyme solutions respectively containing CGTase and β-amylase.

Working Examples 1

Production of High Molecular Weight Glucan Using Waxy Corn Starch, AqBE and TaqMalQ A gelatinized fluid was obtained as follows. First, 200 g of waxy corn starch (available from Sanwa Starch Co., Ltd.) was suspended in 1 L of a 20 mM citric acid buffer solution (pH 7.5), and this suspension was heated to 100° C. to be gelatinized. The waxy corn starch used then had the branch frequency of 6.5%, average degree of polymerization of approximately $1 \times 10^5$, and weight-average molecular weight of approximately $2 \times 10^7$. The gelatinized fluid was cooled to approximately 70° C. AqBE enzyme solution was added to the cooled gelatinized fluid to a concentration of 200 U/g substrate (working example 1-1), 300 U/g substrate (working example 1-2), 700 U/g substrate (working example 1-3), 1,000 U/g substrate (working example 1-4), or 2,000 U/g substrate (working example 1-5). At the same time, TaqMalQ enzyme solution was also added to the gelatinized fluid to a concentration of 0.5 U/g substrate. And then the mixture reacted at 70° C. for 24 hours. Also, AqBE enzyme solution and TaqMalQ enzyme solution were added at the same time to the gelatinized fluid cooled to approximately 70° C. to a concentration of, respectively, 200 U/g substrate and 0.25 U/g substrate, and then reacted at 70° C. for 24 hours (working example 1-6). After the reaction was over, the reaction solutions were heated at 100° C. for 20 minutes and then passed through activated carbon, positive ion exchange chromato-column, and negative ion exchange chromato-column. The collected solutions were frozen and dried to obtain high molecular weight glucans in the form of powder.

Figure 2:
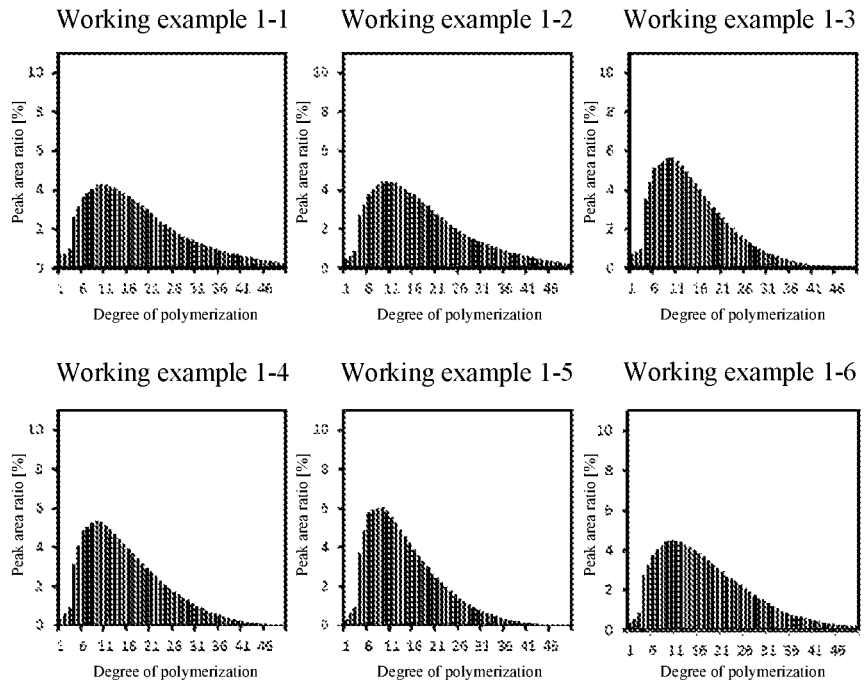
FIG. 2 presents graphs that illustrate unit chain length distributions of high molecular weight glucans obtained in working examples 1.

Table 1 shows the concentrations of enzymes used to produce the high molecular weight glucans and the measurement results of weight-average molecular weights, branch frequencies, and reducing sugar levels of the obtained high molecular weight glucans. Table 2 shows the analysis results of unit chain length distributions of the obtained high molecular weight glucans. FIG. 2 shows the unit chain length distribution graphs of the obtained high molecular weight glucans. All of the unit chain length distributions of the obtained high molecular weight glucans according to the working examples 1-1 to 1-6 exhibit peaks representing higher concentrations in a region of shorter chain lengths with degrees of polymerization of approximately 5 to 15 and also in a region of longer chain lengths with degrees of polymerization of 25 or more, and these distributions are gently curved on the whole, with no prominent peak. This result suggests that these high molecular weight glucans are structurally distinct from the known branched glucans.

The end structures in the high molecular weight glucans of the working examples 1-3 and 1-6 were analyzed by the methylation method. The analysis result shows no partially methylated sugar resulting from end-branching structure, which demonstrates that no end-branching structure was present in the high molecular weight glucans of the working examples 1-3 and 1-6. For comparison, highly-branched dextrin HBD-20 (available from Matsutani Chemical Industry Co., Ltd.) known to have α-1,6-branching structure at non-reducing ends was analyzed to determine its end structure using the methylation method, in which partial methylated sugar resulting from end-branching structure was detected.

Figure 3:
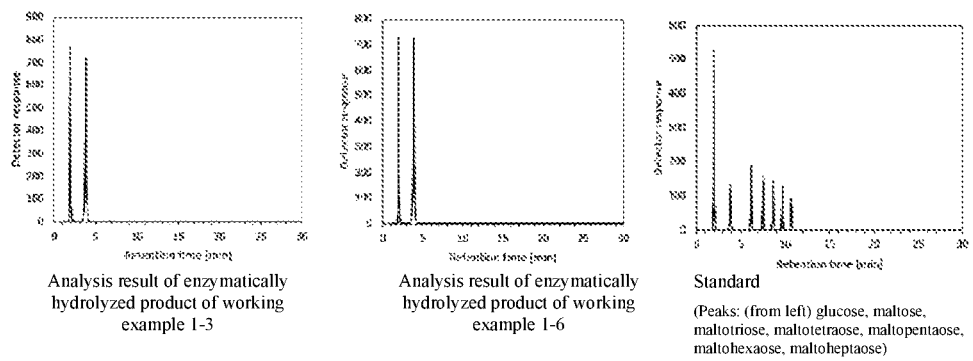
FIG. 3 presents graphs that illustrate an analysis result by an enzymatic method of linking modes of the high molecular weight glucans obtained in working examples 1-3 and 1-6 (product analysis results).

FIG. 3 is graphs showing the analysis result of enzymatic hydrolysate of the high molecular weight glucans in order to analyze the bonding mode of the high molecular weight glucans of the working examples 1-3 and 1-6. The peaks of the enzymatically hydrolyzed products of the high molecular weight glucans of the working examples 1-3 and 1-6 were only glucose and maltose, as is known from FIG. 3. This result suggests that the linking modes of these high molecular weight glucans were limited to α-1,4-glucoside bonds and α-1,6-glucoside bonds and that no α-1,6-glucoside bond was present at non-reducing ends of sugar chains.

TABLE 1

| | | Working example | | | | | |
|---|---|---|---|---|---|---|---|
| | | 1-1 | 1-2 | 1-3 | 1-4 | 1-5 | 1-6 |
| Concentration of enzyme used | AqBE concentration (U/g substrate) | 200 | 300 | 700 | 1000 | 2000 | 200 |
| | TaqMalQ concentration (U/g substrate) | 0.5 | 0.5 | 0.5 | 0.5 | 0.5 | 0.25 |
| Properties of produced high molecular weight glucan | Weight-average molecular weight | 168,600 | 164,900 | 158,400 | 163,600 | 164,400 | 171,200 |
| | Branch frequency (%) | 8.0 | 8.6 | 9.8 | 10.1 | 11.2 | 7.7 |
| | Reducing sugar level (DE) (%) | 0.14 | 0.13 | 0.65 | 0.09 | 0.08 | 0.13 |

TABLE 2

| | Working example | | | | | |
|---|---|---|---|---|---|---|
| | 1-1 | 1-2 | 1-3 | 1-4 | 1-5 | 1-6 |
| $(DP_{1-5}/DP_{6-10}) \times 100$ (%) | 40.7 | 37.9 | 39.3 | 34.9 | 35.1 | 37.1 |
| $(DP_{11-15}/DP_{6-10}) \times 100$ (%) | 101.3 | 99.8 | 90.8 | 90.1 | 82.7 | 101.4 |
| $(DP_{16-20}/DP_{6-10}) \times 100$ (%) | 83.4 | 80.3 | 64.6 | 66.0 | 55.2 | 82.9 |
| $(DP_{21-25}/DP_{6-10}) \times 100$ (%) | 60.3 | 57.2 | 42.1 | 44.1 | 33.3 | 61.2 |
| $(DP_{26-30}/DP_{6-10}) \times 100$ (%) | 40.7 | 38.6 | 25.7 | 26.9 | 18.0 | 41.7 |
| $(DP_{31-35}/DP_{6-10}) \times 100$ (%) | 28.5 | 26.7 | 15.2 | 14.8 | 9.0 | 25.7 |
| $(DP_{36-40}/DP_{6-10}) \times 100$ (%) | 19.8 | 18.1 | 8.9 | 6.9 | 3.7 | 15.0 |
| $DP_{1-5}$ ratio (%) | 8.1 | 7.9 | 9.9 | 9.0 | 10.4 | 7.8 |
| $DP_{1-7}$ ratio (%) | 15.6 | 15.6 | 19.7 | 18.9 | 22.0 | 15.5 |
| $DP_{1-10}$ ratio (%) | 28.1 | 28.7 | 35.2 | 34.8 | 39.9 | 28.7 |
| $DP_{11-24}$ ratio (%) | 46.8 | 47.4 | 48.1 | 49.8 | 49.0 | 49.1 |
| $DP_{6-10}$ ratio (%) | 20.0 | 20.8 | 25.2 | 25.8 | 29.5 | 20.9 |
| $DP_{6-15}$ ratio (%) | 40.2 | 41.6 | 48.1 | 49.0 | 54.0 | 42.1 |
| $DP_{6-40}$ ratio (%) | 86.6 | 87.5 | 87.6 | 90.0 | 89.2 | 89.5 |
| $\{(DP_{1-10}) + (DP_{25-50})\}/DP_{11-24}$ | 1.1 | 1.1 | 1.1 | 1.0 | 1.0 | 1.0 |
| Top peak ratio (%) | 4.3 | 4.4 | 5.2 | 5.4 | 6.0 | 4.5 |
| Slope of 20%-60% cumulative plotting | 3.9 | 4.1 | 5.0 | 5.1 | 5.9 | 4.2 |

Comparative Examples 1

Production of Branched Glucan Using AqBE Alone

A gelatinized fluid was obtained as follows. First, 200 g of waxy corn starch (available from Sanwa Starch Co., Ltd.) was suspended in 1 L of a 20 mM citric acid buffer solution (pH 7.5), and this suspension was heated to 100° C. to be gelatinized (comparative example 1-1). The waxy corn starch used then had the branch frequency of 6.5%, average degree of polymerization of approximately $1 \times 10^5$, and weight-average molecular weight of approximately $2 \times 10^7$. The gelatinized fluid was cooled to approximately 70° C. AqBE enzyme solution was added to the cooled gelatinized fluid to the concentration of 50 U/g substrate (comparative example 1-2), 100 U/g substrate (comparative example 1-3), 200 U/g substrate (comparative example 1-4), 500 U/g substrate (comparative example 1-5), 700 U/g substrate (comparative example 1-6), 5,000 U/g substrate (comparative example 1-7), or 10,000 U/g substrate (comparative example 1-8), and then reacted at 70° C. for 24 hours. Then, the reaction solutions were heated at 100° C. for 20 minutes and then passed through activated carbon, positive ion exchange chromato-column, and negative ion exchange chromato-column. The collected solutions were frozen and dried to obtain branched glucans in the form of powder.

Figure 4:
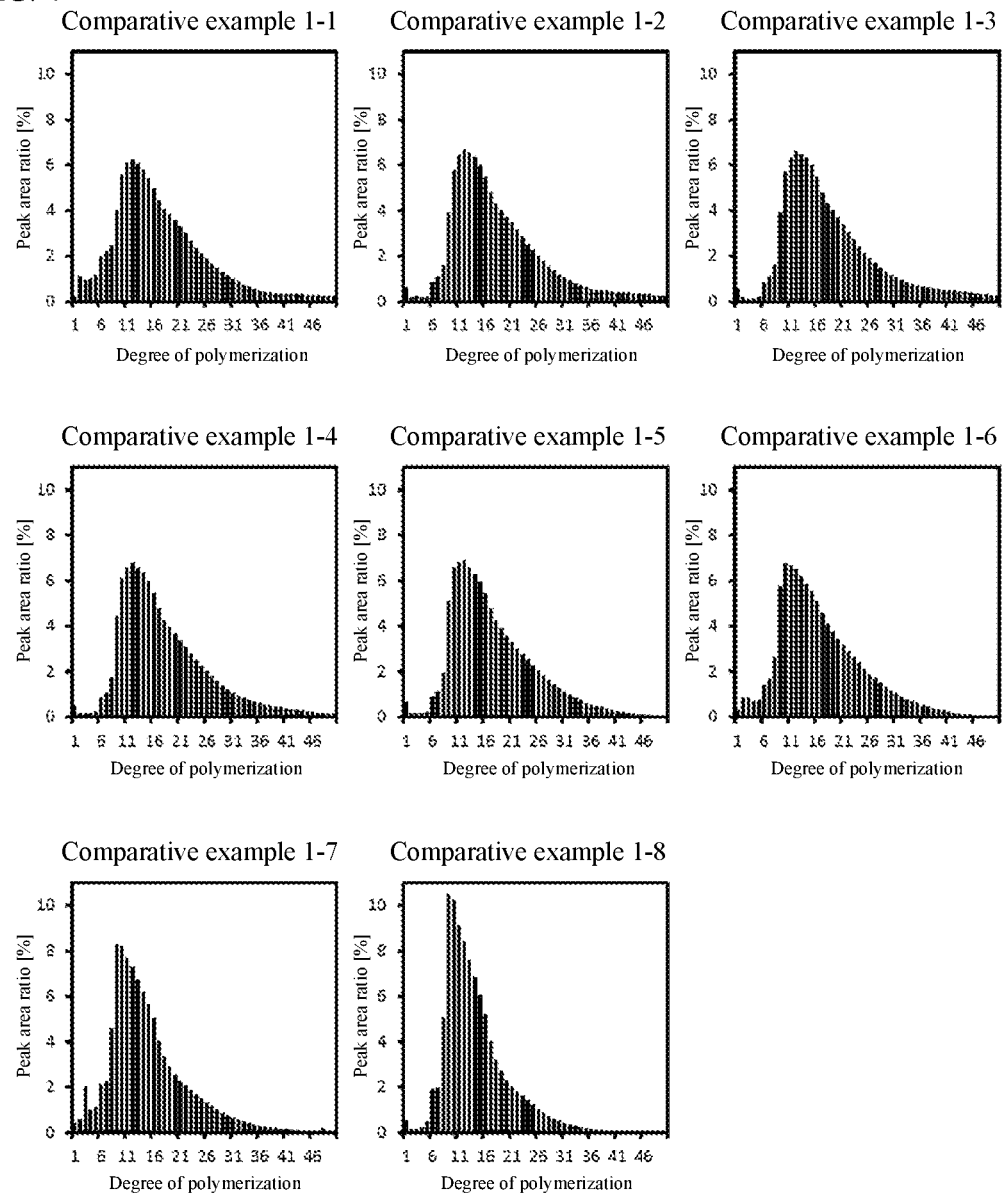
FIG. 4 presents graphs that illustrate unit chain length distributions of branched glucans obtained in comparative examples 1.

Table 3 shows the concentrations of enzymes used to produce the branched glucans and the measurement result of weight-average molecular weights, branch frequencies, and reducing sugar levels of the obtained branched glucans. Table 4 shows the analysis results of unit chain length distributions of the obtained branched glucans. FIG. 4 shows the unit chain length distribution graphs of the obtained branched glucans. In all of the unit chain length distributions of the obtained branched glucans according to the comparative examples 1-1 to 1-8, peaks representing higher concentrations are localized in a region of degrees of polymerization of approximately 11 to 16. Thus, none of the unit chain length distributions of these branched glucans was found to fulfill the properties i) to iii).

approximately $1\times10^5$, and weight-average molecular weight of approximately $2\times10^7$. The gelatinized fluid was cooled to approximately 70° C. AqBE enzyme solution was added to the cooled gelatinized fluid to the concentration of 50 U/g substrate (comparative example 2-1) or 5,000 U/g substrate (comparative example 2-2), and TaqMalQ enzyme solution was added at the same time to the fluid to the concentration of 0.5 U/g substrate, which were reacted at 70° C. for 24 hours. Then, the reaction solutions were heated at 100° C. for 20 minutes and then passed through activated carbon, positive ion exchange chromato-column, and negative ion exchange chromato-column. The collected solutions were frozen and dried to obtain branched glucans in the form of powder.

TABLE 3

| | | Comparative Example | | | | | | | |
|---|---|---|---|---|---|---|---|---|---|
| | | 1-1 | 1-2 | 1-3 | 1-4 | 1-5 | 1-6 | 1-7 | 1-8 |
| Concentration of enzyme used | AqBE concentration (U/g substrate) | — | 50 | 100 | 200 | 500 | 700 | 5,000 | 10,000 |
| Properties of produced branched glucan | Weight-average molecular weight | 4,960,000 | 312,400 | 249,900 | 187,400 | 151,000 | 140,100 | 132,000 | 121,100 |
| | Branch frequency (%) | 6.5 | 6.3 | 6.6 | 6.7 | 7.5 | 8.6 | 9.9 | 10.5 |
| | Reducing sugar level (DE) (%) | 0.49 | 0.10 | 0.05 | 0.06 | 0.02 | 0.49 | 0.53 | 0.16 |

TABLE 4

| | Comparative Example | | | | | | | |
|---|---|---|---|---|---|---|---|---|
| | 1-1 | 1-2 | 1-3 | 1-4 | 1-5 | 1-6 | 1-7 | 1-8 |
| $(DP_{1-5}/DP_{6-10}) \times 100$ (%) | 26.6 | 9.4 | 7.9 | 8.3 | 8.4 | 18.1 | 20.0 | 5.1 |
| $(DP_{11-15}/DP_{6-10}) \times 100$ (%) | 183.3 | 243.9 | 241.3 | 227.6 | 208.9 | 169.5 | 132.1 | 128.1 |
| $(DP_{16-20}/DP_{6-10}) \times 100$ (%) | 128.9 | 169.1 | 168.8 | 155.5 | 140.8 | 115.1 | 70.1 | 58.6 |
| $(DP_{21-25}/DP_{6-10}) \times 100$ (%) | 82.9 | 107.8 | 103.6 | 98.1 | 88.4 | 72.0 | 36.5 | 26.9 |
| $(DP_{26-30}/DP_{6-10}) \times 100$ (%) | 45.1 | 59.1 | 56.9 | 55.3 | 51.7 | 41.1 | 19.6 | 12.4 |
| $(DP_{31-35}/DP_{6-10}) \times 100$ (%) | 22.7 | 29.9 | 31.8 | 29.2 | 26.7 | 21.4 | 9.2 | 4.6 |
| $(DP_{36-40}/DP_{6-10}) \times 100$ (%) | 11.5 | 17.0 | 21.1 | 17.4 | 12.9 | 10.0 | 4.0 | 1.4 |
| $DP_{1-5}$ ratio (%) | 4.3 | 1.2 | 1.0 | 1.2 | 1.3 | 3.3 | 5.1 | 1.5 |
| $DP_{1-7}$ ratio (%) | 8.4 | 3.1 | 2.9 | 3.1 | 3.3 | 6.3 | 9.4 | 5.4 |
| $DP_{1-10}$ ratio (%) | 20.4 | 14.3 | 14.1 | 15.3 | 16.8 | 21.4 | 30.4 | 31.1 |
| $DP_{11-24}$ ratio (%) | 61.5 | 66.0 | 65.2 | 65.7 | 65.7 | 62.5 | 59.1 | 62.1 |
| $DP_{6-10}$ ratio (%) | 16.1 | 13.1 | 13.1 | 14.1 | 15.5 | 18.1 | 25.4 | 29.6 |
| $DP_{6-15}$ ratio (%) | 45.6 | 45.1 | 44.7 | 46.2 | 47.9 | 48.8 | 58.9 | 67.6 |
| $DP_{6-40}$ ratio (%) | 92.5 | 95.2 | 94.8 | 96.4 | 97.6 | 95.8 | 94.2 | 98.4 |
| $\{(DP_{1-10}) + (DP_{25-50})\}/DP_{11-24}$ | 0.6 | 0.5 | 0.5 | 0.5 | 0.5 | 0.6 | 0.7 | 0.6 |
| Top peak ratio (%) | 6.2 | 6.7 | 6.6 | 6.8 | 6.9 | 6.7 | 8.3 | 10.5 |
| Slope of 20%-60% cumulative plotting | 5.9 | 6.4 | 6.3 | 6.4 | 6.4 | 6.3 | 7.7 | 8.8 |

Comparative Examples 2

Figure 5:
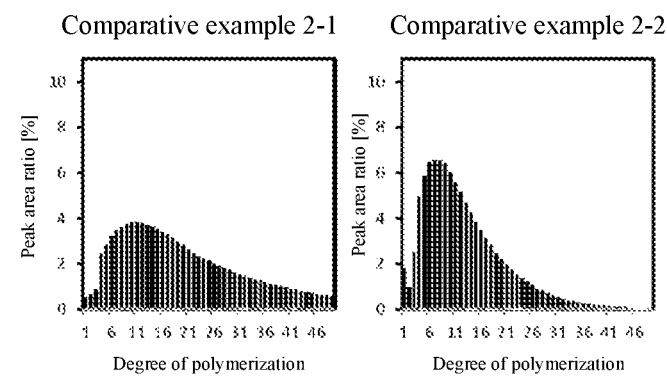
FIG. 5 presents graphs that illustrate unit chain length distributions of branched glucans obtained in comparative examples 2.

Production of Branched Glucan Using Waxy Corn Starch and Small or Excess Quantities of AqBE and TaqMalQ A gelatinized fluid was obtained as follows. First, 200 g of waxy corn starch (available from Sanwa Starch Co., Ltd.) was suspended in 1 L of a 20 mM citric acid buffer solution (pH 7.5), and this suspension was heated to 100° C. to be gelatinized. The waxy corn starch used then had the branch frequency of 6.5%, average degree of polymerization of Table 5 shows the concentrations of enzymes used to produce the branched glucans and the measurement result of weight-average molecular weights, branch frequencies, and reducing sugar levels of the obtained branched glucans. Table 6 shows the analysis results of unit chain length distributions of the obtained branched glucans. FIG. 5 shows the unit chain length distribution graphs of the obtained branched glucans. Neither of the unit chain length distributions of the comparative examples 2-1 and 2-2 was found to fulfill the properties (i) to (iii).

TABLE 5

|  |  | Comparative Example | |
|---|---|---|---|
|  |  | 2-1 | 2-2 |
| Concentration of enzyme used | AqBE concentration (U/g substrate) | 50 | 5,000 |
|  | TaqMalQ concentration (U/g substrate) | 0.5 | 0.5 |
| Properties of produced branched glucan | Weight-average molecular weight | 221,900 | 207,600 |
|  | Branch frequency (%) | 6.5 | 12.5 |
|  | Reducing sugar level (DE) (%) | 0.06 | 0.07 |

TABLE 6

|  | Comparative Example | |
|---|---|---|
|  | 2-1 | 2-1 |
| $(DP_{1-5}/DP_{6-10}) \times 100$ (%) | 40.1 | 50.4 |
| $(DP_{11-15}/DP_{6-10}) \times 100$ (%) | 103.6 | 73.6 |
| $(DP_{16-20}/DP_{6-10}) \times 100$ (%) | 87.0 | 43.7 |
| $(DP_{21-25}/DP_{6-10}) \times 100$ (%) | 65.5 | 23.9 |
| $(DP_{26-30}/DP_{6-10}) \times 100$ (%) | 50.4 | 12.4 |
| $(DP_{31-35}/DP_{6-10}) \times 100$ (%) | 38.5 | 6.0 |
| $(DP_{36-40}/DP_{6-10}) \times 100$ (%) | 29.2 | 2.7 |
| $DP_{1-5}$ ratio (%) | 7.1 | 16.0 |
| $DP_{1-7}$ ratio (%) | 13.7 | 29.0 |
| $DP_{1-10}$ ratio (%) | 24.8 | 47.9 |
| $DP_{11-24}$ ratio (%) | 43.3 | 43.7 |
| $DP_{6-10}$ ratio (%) | 17.7 | 31.8 |
| $DP_{6-15}$ ratio (%) | 36.1 | 55.2 |
| $DP_{6-40}$ ratio (%) | 84.0 | 83.5 |
| $\{(DP_{1-10}) + (DP_{25-50})\}/DP_{11-24}$ | 1.3 | 1.3 |
| Top peak ratio (%) | 3.8 | 6.5 |
| Slope of 20%-60% cumulative plotting | 3.6 | 6.4 |

Comparative Example 3

Analysis of Enzymatically Synthesized Branched Glucan

The weight-average molecular weight, branch frequency, reducing sugar level, and unit chain length distribution were measured for the enzymatically synthesized branched glucan obtained by the method described in Japanese Patent Laid-open Publication No. 2008-95117.

Figure 6:
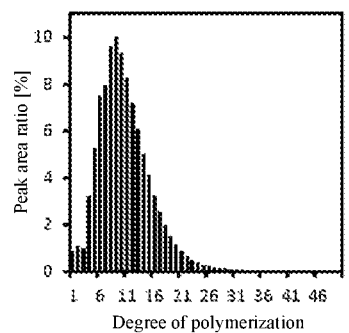
FIG. 6 presents a graph that illustrates a unit chain length distribution of enzymatically synthesized branched glucan obtained in a comparative example 3.

Table 7 shows the measurement result of the weight-average molecular weight, frequency of branching, and reducing sugar level of the enzymatically synthesized branched glucan. Table 8 shows the analysis result of the unit chain length distribution of the enzymatically synthesized branched glucan. FIG. 6 shows the unit chain length distribution graph of the enzymatically synthesized branched glucan. In the unit chain length distribution of the enzymatically synthesized branched glucan according to the comparative example 3, peaks representing higher concentrations are localized in a region of degrees of polymerization of approximately 11 to 16. Thus, this branched glucan was not found to fulfill the properties (i) to (iii).

TABLE 7

|  | Comparative Example 3 |
|---|---|
| Weight-average molecular weight | 3,477,000 |
| Branch frequency (%) | 12.8 |
| Reducing sugar level (DE) (%) | 1.30 |

TABLE 8

|  | Comparative Example 3 |
|---|---|
| $(DP_{1-5}/DP_{6-10}) \times 100$ (%) | 25.6 |
| $(DP_{11-15}/DP_{6-10}) \times 100$ (%) | 69.0 |
| $(DP_{16-20}/DP_{6-10}) \times 100$ (%) | 23.2 |
| $(DP_{21-25}/DP_{6-10}) \times 100$ (%) | 5.7 |
| $(DP_{26-30}/DP_{6-10}) \times 100$ (%) | 1.5 |
| $(DP_{31-35}/DP_{6-10}) \times 100$ (%) | 0.5 |
| $(DP_{36-40}/DP_{6-10}) \times 100$ (%) | 0.2 |
| $DP_{1-5}$ ratio (%) | 11.3 |
| $DP_{1-7}$ ratio (%) | 26.8 |
| $DP_{1-10}$ ratio (%) | 55.7 |
| $DP_{11-24}$ ratio (%) | 43.1 |
| $DP_{6-10}$ ratio (%) | 44.3 |
| $DP_{6-15}$ ratio (%) | 74.9 |
| $DP_{6-40}$ ratio (%) | 88.6 |
| $\{(DP_{1-10}) + (DP_{25-50})\}/DP_{11-24}$ | 1.3 |
| Top peak ratio (%) | 10.0 |
| Slope of 20%-60% cumulative plotting | 9.7 |

Comparative Examples 4

Analysis of Native Glycogen

The weight-average molecular weight, branch frequency, reducing sugar level, and unit chain length distribution were measured for bovine liver glycogen (available from Sigma Chemical Co.) and oyster glycogen (available from MB Biomedicals, LLC).

Figure 7:
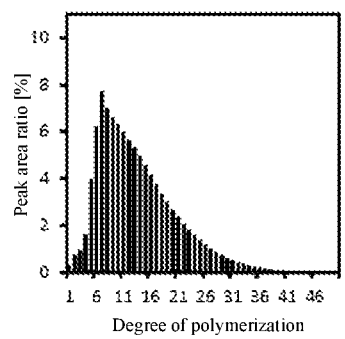
FIG. 7 presents graphs that illustrate unit chain length distributions of native glycogens obtained in comparative examples 4.
Figure 7:
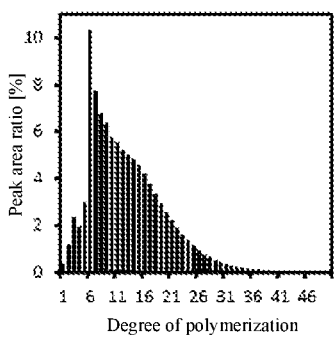

Table 9 shows the measurement result of the weight-average molecular weights, frequencies of branching, and reducing sugar levels of these native glycogens. Table 10 shows the analysis result of the unit chain length distributions of the native glycogens. FIG. 7 shows the unit chain length distributions of the native glycogens. In the unit chain length distributions of the native glycogens according to the comparative examples 4-1 and 4-2, peaks representing higher concentrations are localized in a region of degrees of polymerization of approximately 11 to 16. Thus, neither of these native glycogens was found to fulfill the properties (i) to (iii).

TABLE 9

|  | Comparative Example | |
|---|---|---|
|  | 4-1 | 4-2 |
| Origin | Bovine liver | Oyster |
| Weight-average molecular weight | 1,825,000 | 5,359,000 |
| Branch frequency (%) | 13.6 | 13.1 |
| Reducing sugar level (DE) (%) | 0.21 | 0.15 |

TABLE 10

|  | Comparative Example | |
|---|---|---|
|  | 4-1 | 4-2 |
| $(DP_{1-5}/DP_{6-10}) \times 100$ (%) | 22.1 | 23.5 |
| $(DP_{11-15}/DP_{6-10}) \times 100$ (%) | 78.1 | 68.0 |
| $(DP_{16-20}/DP_{6-10}) \times 100$ (%) | 49.8 | 45.2 |
| $(DP_{21-25}/DP_{6-10}) \times 100$ (%) | 26.7 | 21.9 |
| $(DP_{26-30}/DP_{6-10}) \times 100$ (%) | 12.6 | 8.7 |
| $(DP_{31-35}/DP_{6-10}) \times 100$ (%) | 5.2 | 2.9 |
| $(DP_{36-40}/DP_{6-10}) \times 100$ (%) | 1.5 | 0.9 |
| $DP_{1-5}$ ratio (%) | 7.4 | 8.7 |
| $DP_{1-7}$ ratio (%) | 21.3 | 26.7 |

TABLE 10-continued

|  | Comparative Example | |
| --- | --- | --- |
|  | 4-1 | 4-2 |
| $DP_{1-10}$ ratio (%) | 41.2 | 45.5 |
| $DP_{11-24}$ ratio (%) | 50.8 | 48.7 |
| $DP_{6-10}$ ratio (%) | 33.7 | 36.9 |
| $DP_{6-15}$ ratio (%) | 60.1 | 61.9 |
| $DP_{6-40}$ ratio (%) | 92.4 | 91.2 |
| $\{(DP_{1-10}) + (DP_{25-50})\}/DP_{11-24}$ | 1.0 | 1.1 |
| Top peak ratio (%) | 7.7 | 10.3 |
| Slope of 20%-60% cumulative plotting | 6.4 | 5.9 |

Working Example 2

Production of High Molecular Weight Glucan Using Tapioca Starch, AqBE, and TaqMalQ A gelatinized fluid was obtained as follows. First, 200 g of tapioca starch (available from Tokai Denpun Co., Ltd.) was suspended in 1 L of a 20 mM citric acid buffer solution (pH 7.5), and this suspension was heated to 100° C. to be gelatinized. The tapioca starch used then had the branch frequency of 4.8%, average degree of polymerization of approximately $3 \times 10^4$, and weight-average molecular weight of approximately $5 \times 10^6$. The gelatinized fluid was cooled to approximately 70° C. AqBE enzyme solution was added to the cooled gelatinized fluid to the concentration of 1,400 U/g substrate, and TaqMalQ enzyme solution was also added at the same time to the concentration of 0.25 U/g substrate, and then reacted at 70° C. for 24 hours. Then, the reaction solution was heated at 100° C. for 20 minutes and then passed through activated carbon, positive ion exchange chromato-column, and negative ion exchange chromato-column. The collected solution was frozen and dried to obtain a high molecular weight glucan in the form of powder.

Figure 8:
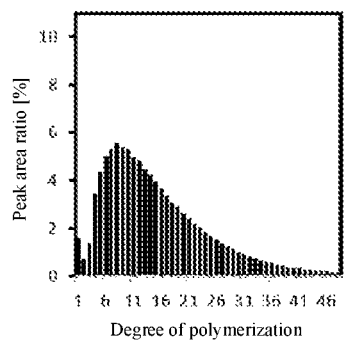
FIG. 8 presents a graph that illustrates a unit chain length distribution of a high molecular weight glucan obtained in a working example 2.

Table 11 shows the concentrations of enzymes used to produce the high molecular weight glucan and the measurement results of the weight-average molecular weight, branch frequency, and reducing sugar level of the obtained high molecular weight glucan. Table 12 shows the analysis result of the unit chain length distribution of the obtained high molecular weight glucan. FIG. 8 shows the unit chain length distribution graph of the obtained high molecular weight glucan. The high molecular weight glucan according to the working example 2 exhibits peaks representing higher concentrations in a region of shorter chain lengths with degrees of polymerization of approximately 5 to 15 and in a region of longer chain lengths with degrees of polymerization of 25 or more, and this distribution is gently curved on the whole, with no prominent peak. This result suggests that this high molecular weight glucan is structurally distinct from the known branched glucans.

TABLE 11

|  |  | Working Example 2 |
| --- | --- | --- |
| Concentration of enzyme used | AqBE concentration (U/g substrate) | 1,400 |
|  | TaqMalQ concentration (U/g substrate) | 0.25 |
| Properties of produced high molecular weight glucan | Weight-average molecular weight | 149,800 |
|  | Frequency of branching (%) | 9.6 |

TABLE 11-continued

|  | Working Example 2 |
| --- | --- |
| Reducing sugar level (DE) (%) | 0.33 |

TABLE 12

|  | Working example 2 |
| --- | --- |
| $(DP_{1-5}/DP_{6-10}) \times 100$ (%) | 43.0 |
| $(DP_{11-15}/DP_{6-10}) \times 100$ (%) | 84.6 |
| $(DP_{16-20}/DP_{6-10}) \times 100$ (%) | 58.5 |
| $(DP_{21-25}/DP_{6-10}) \times 100$ (%) | 37.7 |
| $(DP_{26-30}/DP_{6-10}) \times 100$ (%) | 23.1 |
| $(DP_{31-35}/DP_{6-10}) \times 100$ (%) | 13.7 |
| $(DP_{36-40}/DP_{6-10}) \times 100$ (%) | 7.8 |
| $DP_{1-5}$ ratio (%) | 11.4 |
| $DP_{1-7}$ ratio (%) | 21.6 |
| $DP_{1-10}$ ratio (%) | 37.8 |
| $DP_{11-24}$ ratio (%) | 46.2 |
| $DP_{6-10}$ ratio (%) | 26.5 |
| $DP_{6-15}$ ratio (%) | 48.8 |
| $DP_{6-40}$ ratio (%) | 86.1 |
| $\{(DP_{1-10}) + (DP_{25-50})\}/DP_{11-24}$ | 1.2 |
| Top peak ratio (%) | 5.5 |
| Slope of 20%-60% cumulative plotting | 5.0 |

Working Examples 3

Production of High Molecular Weight Glucan Using Waxy Corn Starch, AqBE, and CGTase A gelatinized fluid was obtained as follows. First, 200 g of waxy corn starch (available from Sanwa Starch Co., Ltd.) was suspended in 1 L of a 20 mM citric acid buffer solution (pH 7.5), and this suspension was heated to 100° C. to be gelatinized. The waxy corn starch used then had the branch frequency of 6.5%, average degree of polymerization of approximately $1 \times 10^5$, and weight-average molecular weight of approximately $2 \times 10^7$. The gelatinized fluid was cooled to approximately 70° C. AqBE enzyme solution was added to the cooled gelatinized fluid to the concentration of 700 U/g substrate, and CGTase enzyme solution was also added at the same time to the concentration of 10 U/g substrate (working example 3-1) or 50 U/g substrate (working example 3-2), and then reacted at 60° C. for 24 hours. Then, the reaction solutions were heated at 100° C. for 20 minutes and then passed through activated carbon, positive ion exchange chromato-column, and negative ion exchange chromato-column. The collected solutions were frozen and dried to obtain high molecular weight glucans in the form of powder.

Figure 9:
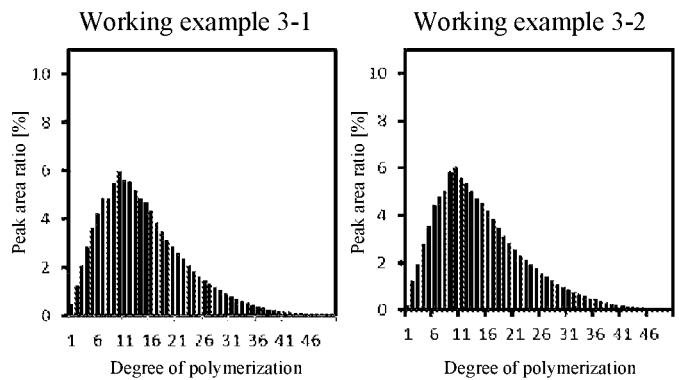
FIG. 9 presents graphs that illustrate unit chain length distributions of high molecular weight glucans obtained in working examples 3.

Table 13 shows the concentrations of enzymes used to produce the high molecular weight glucans and the measurement results of the weight-average molecular weights, frequencies of branching, and reducing sugar levels of the obtained high molecular weight glucans. Table 14 shows the analysis result of the unit chain length distributions of the obtained high molecular weight glucans. FIG. 9 shows the unit chain length distribution graphs of the high molecular weight glucans. Similarly to the working examples 1 and 2, the high molecular weight glucans obtained in the working examples 3 exhibit peaks representing higher concentrations in a region of shorter chain lengths with degrees of polymerization of approximately 5 to 15 and in a region of longer chain lengths with degrees of polymerization of 25 or more, and these distributions are gently curved on the whole, with no prominent peak.

TABLE 13

|  |  | Working example | |
|---|---|---|---|
|  |  | 3-1 | 3-2 |
| Concentration of enzyme used | AqBE concentration (U/g substrate) | 700 | 700 |
|  | CGTase concentration (U/g substrate) | 10 | 50 |
| Properties of produced high molecular weight glucan | Weight-average molecular weight | 145,100 | 121,300 |
|  | Branch frequency (%) | 8.3 | 10.1 |
|  | Reducing sugar level (DE) (%) | 0.07 | 0.49 |

TABLE 14

|  | Working example | |
|---|---|---|
|  | 3-1 | 3-2 |
| $(DP_{1-5}/DP_{6-10}) \times 100$ (%) | 40.2 | 36.9 |
| $(DP_{11-15}/DP_{6-10}) \times 100$ (%) | 102.1 | 96.6 |
| $(DP_{16-20}/DP_{6-10}) \times 100$ (%) | 69.4 | 67.1 |
| $(DP_{21-25}/DP_{6-10}) \times 100$ (%) | 41.1 | 40.6 |
| $(DP_{26-30}/DP_{6-10}) \times 100$ (%) | 23.1 | 23.7 |
| $(DP_{31-35}/DP_{6-10}) \times 100$ (%) | 11.5 | 12.3 |
| $(DP_{36-40}/DP_{6-10}) \times 100$ (%) | 5.1 | 5.3 |
| $DP_{1-5}$ ratio (%) | 10.2 | 9.6 |
| $DP_{1-7}$ ratio (%) | 19.2 | 18.7 |
| $DP_{1-10}$ ratio (%) | 35.5 | 35.5 |
| $DP_{11-24}$ ratio (%) | 52.2 | 51.3 |
| $DP_{6-10}$ ratio (%) | 25.3 | 25.9 |
| $DP_{6-15}$ ratio (%) | 51.1 | 51.0 |
| $DP_{6-40}$ ratio (%) | 89.1 | 89.7 |
| $\{(DP_{1-10}) + (DP_{25-50})\}/DP_{11-24}$ | 0.9 | 0.9 |
| Top peak ratio (%) | 5.8 | 6.0 |
| Slope of 20%-60% cumulative plotting | 5.5 | 5.4 |

Working Examples 4

Production of High Molecular Weight Glucan Using Waxy Corn Starch, AqBE, MalQ, and CGTase A gelatinized fluid was obtained as follows. First, 200 g of waxy corn starch (available from Sanwa Starch Co., Ltd.) was suspended in 1 L of a 20 mM citric acid buffer solution (pH 7.5), and this suspension was heated to 100° C. to be gelatinized. The waxy corn starch used then had the branch frequency of 6.5%, average degree of polymerization of approximately $1 \times 10^5$, and weight-average molecular weight of approximately $2 \times 10^7$. The gelatinized fluid was cooled to approximately 60° C. AqBE enzyme solution was added to the cooled gelatinized fluid to the concentration of 700 U/g substrate. The following enzyme solutions were also added at the same time to the gelatinized solution; CGTase enzyme solution and TaqMalQ enzyme solution to the concentrations of, respectively, 2 U/g substrate and 0.2 U/g substrate (working example 4-1), and CGTase enzyme solution and TaqMalQ solution to the concentrations of, respectively, 5 U/g substrate and 0.2 U/g substrate (working example 4-2), and then reacted at 60° C. for 24 hours. Then, the reaction solution was heated at 100° C. for 20 minutes and then passed through activated carbon, positive ion exchange chromato-column, and negative ion exchange chromato-column. The collected solutions were frozen and dried to obtain high molecular weight glucans in the form of powder.

Figure 10:
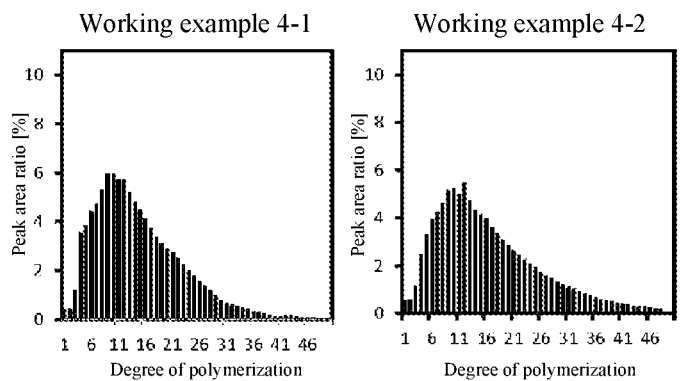
FIG. 10 presents graphs that illustrate unit chain length distributions of high molecular weight glucans obtained in working examples 4.

Table 15 shows the concentrations of enzymes used to produce the high molecular weight glucans and the measurement results of the weight-average molecular weights, branch frequencies, and reducing sugar levels of the obtained high molecular weight glucans. Table 16 shows the analysis result of the unit chain length distributions of the obtained high molecular weight glucans. FIG. 10 shows the unit chain length distributions graphs of the obtained high molecular weight glucans. The high molecular weight glucans according to the working examples 4 exhibit peaks representing higher concentrations in a region of shorter chain lengths with degrees of polymerization of approximately 5 to 15 and in a region of longer chain lengths with degrees of polymerization of 25 or more, and these distributions are gently curved on the whole, with no prominent peak.

TABLE 15

|  |  | Working example | |
|---|---|---|---|
|  |  | 4-1 | 4-2 |
| Concentration of enzyme used | AqBE concentration (U/g substrate) | 700 | 700 |
|  | TaqMalQ concentration (U/g substrate) | 0.2 | 0.2 |
|  | CGTase concentration (U/g substrate) | 2 | 5 |
| Properties of produced high molecular weight glucan | Weight-average molecular weight | 159,100 | 150,500 |
|  | Branch frequency (%) | 8.6 | 8.9 |
|  | Reducing sugar level (DE) (%) | 0.34 | 0.34 |

TABLE 16

|  | Working example | |
|---|---|---|
|  | 4-1 | 4-2 |
| $(DP_{1-5}/DP_{6-10}) \times 100$ (%) | 35.8 | 34.8 |
| $(DP_{11-15}/DP_{6-10}) \times 100$ (%) | 98.2 | 102.2 |
| $(DP_{16-20}/DP_{6-10}) \times 100$ (%) | 65.2 | 73.0 |
| $(DP_{21-25}/DP_{6-10}) \times 100$ (%) | 42.9 | 49.0 |
| $(DP_{26-30}/DP_{6-10}) \times 100$ (%) | 21.9 | 31.8 |
| $(DP_{31-35}/DP_{6-10}) \times 100$ (%) | 9.8 | 19.8 |
| $(DP_{36-40}/DP_{6-10}) \times 100$ (%) | 4.0 | 12.0 |
| $DP_{1-5}$ ratio (%) | 9.4 | 8.0 |
| $DP_{1-7}$ ratio (%) | 18.5 | 16.2 |
| $DP_{1-10}$ ratio (%) | 35.7 | 31.2 |
| $DP_{11-24}$ ratio (%) | 52.4 | 49.9 |
| $DP_{6-10}$ ratio (%) | 26.3 | 23.1 |
| $DP_{6-15}$ ratio (%) | 52.1 | 46.8 |
| $DP_{6-40}$ ratio (%) | 89.9 | 89.7 |
| $\{(DP_{1-10}) + (DP_{25-50})\}/DP_{11-24}$ | 0.9 | 1.0 |
| Top peak ratio (%) | 5.9 | 5.4 |
| Slope of 20%-60% cumulative plotting | 5.4 | 4.8 |

Comparative Examples 5

Production of Branched Glucan Using Waxy Corn Starch, AqBE, and Small Quantity of MalQ or CGTase A gelatinized fluid was obtained as follows. First, 200 g of waxy corn starch (available from Sanwa Starch Co., Ltd.) was suspended in 1 L of a 20 mM citric acid buffer solution (pH 7.5), and this suspension was heated to 100° C. to be gelatinized. The waxy corn starch used then had the branch frequency of 6.5%, average degree of polymerization of approximately $1 \times 10^5$, and weight-average molecular weight of approximately $2 \times 10^7$. The gelatinized fluid was cooled to approximately 60° C. The AqBE enzyme solution was added to the cooled gelatinized fluid to the concentration of 700 U/g substrate. The following enzyme solutions were also added at the same time to the gelatinized solution; TaqMalQ enzyme solution to the concentration of 0.2 U/g substrate (comparative example 5-1) or CGTase enzyme solution to the concentration of 5 U/g substrate (comparative example 5-2), or CGTase enzyme solution to the concentration of 2 U/g substrate and TaqMalQ solution to the concentration of 0.1 U/g substrate (comparative example 5-3), and then reacted 60° C. for 24 hours. Then, the reaction solutions were heated at 100° C. for 20 minutes and then passed through activated carbon, positive ion exchange chromato-column, and negative ion exchange chromato-column. The collected solutions were frozen and dried to obtain branched glucans in the form of powder.

Figure 11:
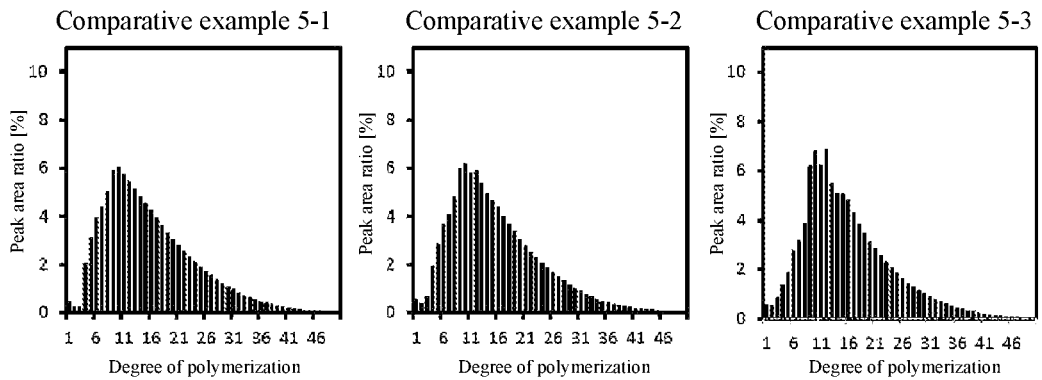
FIG. 11 presents graphs that illustrate unit chain length distributions of branched glucans obtained in comparative examples 5.

Table 17 shows the concentrations of enzymes used to produce the branched glucans and the measurement results of the weight-average molecular weights, branch frequencies, and reducing sugar levels of the obtained branched glucans. Table 18 shows the analysis result of the unit chain length distributions of the obtained branched glucans. FIG. 11 shows the unit chain length distribution graphs of the obtained branched glucans. In the case of the branched glucans according to the comparative examples 5-1 to 5-3, the disproportionation reaction by MalQ and/or CGTase has not progressed sufficiently, and none of these branched glucans was found to fulfill the properties (i) to (iii).

Working Examples 5

Production of High Molecular Weight Glucan Using Waxy Corn Starch, AqBE and B-Amylase A gelatinized fluid was obtained as follows. First, 200 g of waxy corn starch (available from Sanwa Starch Co., Ltd.) was suspended in 1 L of a 20 mM citric acid buffer solution (pH 7.5), and this suspension was heated to 100° C. to be gelatinized. The waxy corn starch used then had the branch frequency of 6.5%, average degree of polymerization of approximately $1 \times 10^5$, and weight-average molecular weight of approximately $2 \times 10^7$. The gelatinized fluid was cooled to approximately 70° C. The AqBE enzyme solution was added to the cooled gelatinized fluid to the concentration of 100 U/g substrate, and then reacted 70° C. for 24 hours. This reaction solution was heated at 100° C. for 20 minutes to inactivate BE and then cooled to 37° C. Then, (β-amylase enzyme solution was added to the solution to the concentration of 15 U/g substrate and reacted at 37° C. for one hour (working example 5-1), or two hours (working example 5-2). After the reaction was over, the reaction solutions were heated at 100° C. for 20 minutes and then passed through activated carbon, positive ion exchange chromato-column, and negative ion exchange chromato-column. Then, an equivalent ethanol was added to each of the collected solutions, from which a precipitate was centrifugally collected (ethanol precipitation). The ethanol precipitation was performed three times each, and the collected precipitate was dissolved in water. The solutions thus obtained were frozen and dried to obtain high molecular weight glucans in the form of powder.

Figure 12:
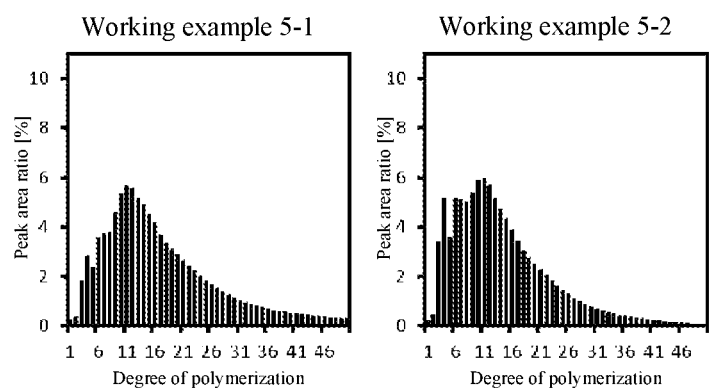
FIG. 12 presents graphs that illustrate unit chain length distributions of high molecular weight glucans obtained in working examples 5.

Table 19 shows the concentrations of enzymes used to produce the high molecular weight glucans and the measurement results of the weight-average molecular weights, branch frequencies, reducing sugar levels, and yields of the obtained high molecular weight glucans. Table 20 shows the analysis result of the unit chain length distributions of the obtained high molecular weight glucans. FIG. 12 shows the unit chain length distribution graphs of the obtained high molecular weight glucans.

The high molecular weight glucans obtained in the working examples 5-1 and 5-2 exhibit peaks representing higher concentrations in a region of shorter chain lengths with degrees of polymerization of approximately 5 to 15 and in a region of longer chain lengths with degrees of polymerization of 25 or more, and these distributions are gently curved on the whole, with no prominent peak. However, the yields of these high molecular weight glucans were not very

TABLE 17

| | | Comparative Example | | |
|---|---|---|---|---|
| | | 5-1 | 5-2 | 5-3 |
| Concentration of enzyme used | AqBE concentration (U/g substrate) | 700 | 700 | 700 |
| | TaqMalQ concentration (U/g substrate) | 0.2 | 0.0 | 0.1 |
| | CGTase concentration (U/g substrate) | 0 | 5 | 2 |
| Properties of produced branched glucan | Weight-average molecular weight | 161,700 | 155,300 | 146,200 |
| | Branch frequency (%) | 7.6 | 7.8 | 7.1 |
| | Reducing sugar level (DE) (%) | 0.22 | 0.30 | 0.64 |

TABLE 18

| | Comparative Example | | |
|---|---|---|---|
| | 5-1 | 5-2 | 5-3 |
| $(DP_{1-5}/DP_{6-10}) \times 100$ (%) | 24.0 | 25.9 | 22.7 |
| $(DP_{11-15}/DP_{6-10}) \times 100$ (%) | 101.4 | 107.8 | 125.9 |
| $(DP_{16-20}/DP_{6-10}) \times 100$ (%) | 71.8 | 74.4 | 85.5 |
| $(DP_{21-25}/DP_{6-10}) \times 100$ (%) | 46.2 | 46.5 | 50.9 |
| $(DP_{26-30}/DP_{6-10}) \times 100$ (%) | 27.3 | 26.8 | 28.5 |
| $(DP_{31-35}/DP_{6-10}) \times 100$ (%) | 14.4 | 13.6 | 15.3 |
| $(DP_{36-40}/DP_{6-10}) \times 100$ (%) | 6.6 | 6.2 | 6.9 |
| $DP_{1-5}$ ratio (%) | 6.1 | 6.4 | 5.2 |
| $DP_{1-7}$ ratio (%) | 14.4 | 14.2 | 11.1 |
| $DP_{1-10}$ ratio (%) | 31.4 | 31.1 | 27.9 |
| $DP_{11-24}$ ratio (%) | 53.6 | 54.7 | 57.9 |
| $DP_{6-10}$ ratio (%) | 25.3 | 24.7 | 22.8 |
| $DP_{6-15}$ ratio (%) | 50.9 | 51.4 | 51.5 |
| $DP_{6-40}$ ratio (%) | 93.0 | 92.8 | 94.1 |
| $\{(DP_{1-10}) + (DP_{25-50})\}/DP_{11-24}$ | 0.9 | 0.8 | 0.7 |
| Top peak ratio (%) | 6.0 | 6.2 | 6.8 |
| Slope of 20%-60% cumulative plotting | 5.3 | 5.5 | 5.9 | high because a large amount of maltose was by-produced as a result of using (β-amylase to produce these high molecular weight glucans.

TABLE 19

|  |  | Working example | |
|---|---|---|---|
|  |  | 5-1 | 5-2 |
| Concentration and reaction time of enzyme used | AqBE concentration (U/g substrate) | 100 | 100 |
|  | β-amylase concentration (U/g substrate) | 15 | 15 |
|  | β-amylase reaction time (hr) | 1 | 2 |
| Properties of produced high molecular weight glucan | Weight-average molecular weight | 266,000 | 247,000 |
|  | Branch frequency (%) | 7.8 | 8.8 |
|  | Reducing sugar level (DE) (%) | 0.12 | 0.17 |

TABLE 20

|  | Working example | |
|---|---|---|
|  | 5-1 | 5-2 |
| $(DP_{1-5}/DP_{6-10}) \times 100$ (%) | 35.8 | 47.9 |
| $(DP_{11-15}/DP_{6-10}) \times 100$ (%) | 122.9 | 97.4 |
| $(DP_{16-20}/DP_{6-10}) \times 100$ (%) | 81.5 | 58.7 |
| $(DP_{21-25}/DP_{6-10}) \times 100$ (%) | 52.7 | 34.3 |
| $(DP_{26-30}/DP_{6-10}) \times 100$ (%) | 32.8 | 18.8 |
| $(DP_{31-35}/DP_{6-10}) \times 100$ (%) | 20.7 | 10.2 |
| $(DP_{36-40}/DP_{6-10}) \times 100$ (%) | 14.1 | 5.7 |
| $DP_{1-5}$ ratio (%) | 7.5 | 12.7 |
| $DP_{1-7}$ ratio (%) | 14.7 | 22.9 |
| $DP_{1-10}$ ratio (%) | 28.4 | 39.1 |
| $DP_{11-24}$ ratio (%) | 52.0 | 49.0 |
| $DP_{6-10}$ ratio (%) | 20.9 | 26.5 |
| $DP_{6-15}$ ratio (%) | 46.6 | 52.3 |
| $DP_{6-40}$ ratio (%) | 88.8 | 86.0 |
| $\{(DP_{1-10}) + (DP_{25-50})\}/DP_{11-24}$ | 0.9 | 1.0 |
| Top peak ratio (%) | 5.7 | 5.9 |
| Slope of 20%-60% cumulative plotting | 5.1 | 5.6 |

Comparative Examples 6

Production if Branched Glucan Using Waxy Corn Starch, AqBE, and B-Amylase, with Long-Hour B-Amylase Treatment A gelatinized fluid was obtained as follows. First, 200 g of waxy corn starch (available from Sanwa Starch Co., Ltd.) was suspended in 1 L of a 20 mM citric acid buffer solution (pH 7.5), and this suspension was heated to 100° C. to be gelatinized. The waxy corn starch used then had the branch frequency of 6.5%, average degree of polymerization of approximately $1 \times 10^5$, and weight-average molecular weight of approximately $2 \times 10^7$. The gelatinized fluid was cooled to approximately 70° C. AqBE enzyme solution was added to the cooled gelatinized fluid to the concentration of 100 U/g substrate, and then reacted at 70° C. for 24 hours. This reaction solution was heated at 100° C. for 20 minutes to inactivate the BE and then cooled to 37° C. Then, (β-amylase enzyme solution was added to the solution to the concentration of 15 U/g substrate and reacted at 37° C. for 3 hours (comparative example 6-1), 4 hours (comparative example 6-2), or 6 hours (comparative example 6-3). After the reaction was over, the reaction solutions were heated at 100° C. for 20 minutes and then passed through activated carbon, positive ion exchange chromato-column, and negative ion exchange chromato-column. Then, an equivalent ethanol was added to each of the collected solutions, from which a precipitate was centrifugally collected (ethanol precipitation). The ethanol precipitation was performed three times each, and the collected precipitate was dissolved in water. The solutions thus obtained were frozen and dried to obtain branched glucans in the form of powder.

Figure 13:
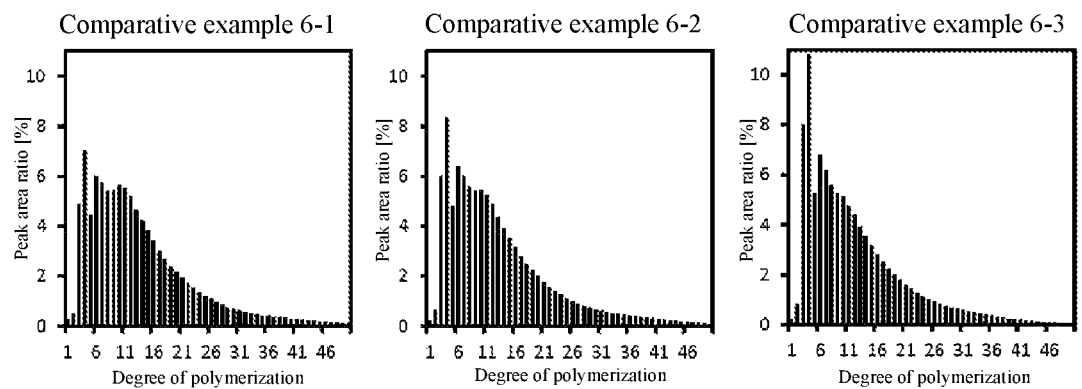
FIG. 13 presents graphs that illustrate unit chain length distributions of branched glucans obtained in comparative examples 6.

Table 21 shows the concentrations of enzymes used to produce the branched glucans and the measurement results of the weight-average molecular weights, branch frequencies, reducing sugar levels, and yields of the obtained branched glucans. Table 22 shows the analysis result of the unit chain length distributions of the obtained branched glucans. FIG. 13 shows the unit chain length distribution graphs of the obtained branched glucans. In the branched glucans of the comparative examples 6-1 to 6-3, peaks representing higher concentrations are localized in a region of degrees of polymerization of approximately 16 or less. Thus, none of the unit chain length distributions of these branched glucans was found to fulfill the properties (i) to (iii)

TABLE 21

|  |  | Comparative Example | | |
|---|---|---|---|---|
|  |  | 6-1 | 6-2 | 6-3 |
| Concentration and reaction time of enzyme used | AqBE concentration (U/g substrate) | 100 | 100 | 100 |
|  | β-amylase concentration (U/g substrate) | 15 | 15 | 15 |
|  | β-amylase reaction time (hr) | 3 | 4 | 6 |
| Properties of produced branched glucan | Weight-average molecular weight | 230,800 | 221,150 | 214,050 |
|  | Branch frequency (%) | 10.3 | 11.1 | 13.0 |
|  | Reducing sugar level (DE) (%) | 0.27 | 0.28 | 0.22 |

TABLE 22

|  | Comparative Example | | |
|---|---|---|---|
|  | 6-1 | 6-2 | 6-3 |
| $(DP_{1-5}/DP_{6-10}) \times 100$ (%) | 60.5 | 69.1 | 86.9 |
| $(DP_{11-15}/DP_{6-10}) \times 100$ (%) | 82.8 | 75.8 | 68.5 |
| $(DP_{16-20}/DP_{6-10}) \times 100$ (%) | 48.3 | 43.7 | 39.3 |
| $(DP_{21-25}/DP_{6-10}) \times 100$ (%) | 27.2 | 24.5 | 22.2 |

TABLE 22-continued

| | Comparative Example | | |
|---|---|---|---|
| | 6-1 | 6-2 | 6-3 |
| $(DP_{26-30}/DP_{6-10}) \times 100$ (%) | 14.9 | 13.8 | 13.2 |
| $(DP_{31-35}/DP_{6-10}) \times 100$ (%) | 9.0 | 8.8 | 8.4 |
| $(DP_{36-40}/DP_{6-10}) \times 100$ (%) | 6.0 | 6.0 | 4.8 |
| $DP_{1-5}$ ratio (%) | 17.1 | 19.9 | 25.1 |
| $DP_{1-7}$ ratio (%) | 28.8 | 32.3 | 38.0 |
| $DP_{1-10}$ ratio (%) | 45.2 | 48.7 | 53.9 |
| $DP_{11-24}$ ratio (%) | 43.4 | 40.3 | 36.5 |
| $DP_{6-10}$ ratio (%) | 28.2 | 28.8 | 28.8 |
| $DP_{6-15}$ ratio (%) | 51.5 | 50.6 | 48.6 |
| $DP_{6-40}$ ratio (%) | 81.2 | 78.4 | 74.0 |
| $\{(DP_{1-10}) + (DP_{25-50})\}/DP_{11-24}$ | 1.3 | 1.5 | 1.7 |
| Top peak ratio (%) | 7.0 | 8.3 | 10.8 |
| Slope of 20%-60% cumulative plotting | 5.5 | 5.4 | 5.6 |

Working Example 6

In Vitro Digestibility Test

An in vitro digestibility test was performed on the branched glucans of the working examples 1 to 5, branched glucans of the comparative examples 1, 2, 5, and 6, enzymatically synthesized glucan of the comparative example 3, and native glycogens of the comparative examples 4. From the results, their initial digestion rate coefficients k, the percentage of rapid-digestible fractions, the percentage of slow-digestible fractions, and the percentage of indigestible fractions were calculated.

Table 23 shows the obtained result. In all of the high molecular weight glucans obtained in the working examples, the initial digestion rate coefficient k was less than 0.029, and the percentage of the indigestible fraction was less than 10%. In the branched glucans of the comparative examples, however, the initial digestion rate coefficient k was 0.029 or more, or the percentage of the indigestible fraction was 10% or more with the initial digestion rate coefficient k of less than 0.029. In the enzymatically synthesized glucan and the native glycogens, the initial digestion rate coefficient k was 0.029 or more, and the percentage of the indigestible fraction was 10% or more.

TABLE 23

| | Working example | | | | | | |
|---|---|---|---|---|---|---|---|
| | 1-1 | 1-2 | 1-3 | 1-4 | 1-5 | 1-6 | 2 |
| Initial digestion rate coefficient k | 0.027 | 0.027 | 0.025 | 0.025 | 0.025 | 0.027 | 0.028 |
| Indigestible fraction (%) | 3.5 | 3.9 | 4.0 | 7.9 | 9.9 | 3.3 | 2.6 |
| Rapid-digestible fraction (%) | 40.5 | 39.6 | 37.2 | 39.6 | 38.6 | 39.4 | 43.0 |
| Slow-digestible fraction (%) | 55.9 | 56.5 | 58.7 | 52.6 | 51.5 | 57.3 | 54.4 |

| | Working example | | | | | | Comparative Example |
|---|---|---|---|---|---|---|---|
| | 3-1 | 3-2 | 4-1 | 4-2 | 5-1 | 5-2 | 1-1 |
| Initial digestion rate coefficient k | 0.028 | 0.028 | 0.028 | 0.028 | 0.028 | 0.028 | 0.040 |
| Indigestible fraction (%) | 2.2 | 4.5 | 4.7 | 6.3 | 1.1 | 2.2 | 0.5 |
| Rapid-digestible fraction (%) | 41.4 | 41.1 | 43.1 | 40.9 | 41.5 | 42.3 | 54.7 |
| Slow-digestible fraction (%) | 56.5 | 54.4 | 52.2 | 52.8 | 57.4 | 55.5 | 44.8 |

| | Comparative Example | | | | | | |
|---|---|---|---|---|---|---|---|
| | 1-2 | 1-3 | 1-4 | 1-5 | 1-6 | 1-7 | 1-8 |
| Initial digestion rate coefficient k | 0.035 | 0.032 | 0.032 | 0.033 | 0.032 | 0.034 | 0.03 |
| Indigestible fraction (%) | 2.2 | 2.6 | 2.6 | 2.5 | 3 | 1.8 | 4.6 |
| Rapid-digestible fraction (%) | 49.4 | 46.5 | 45.7 | 47.7 | 46.6 | 48.4 | 44.2 |
| Slow-digestible fraction (%) | 48.4 | 50.9 | 51.7 | 49.7 | 50.4 | 49.8 | 51.1 |

| | Comparative Example | | | | | | |
|---|---|---|---|---|---|---|---|
| | 2-1 | 2-2 | 3 | 4-1 | 4-2 | 5-1 | 5-2 |
| Initial digestion rate coefficient k | 0.032 | 0.022 | 0.030 | 0.029 | 0.029 | 0.033 | 0.031 |
| Indigestible fraction (%) | 2.2 | 22.7 | 16.4 | 10.4 | 12.6 | 0.8 | 2.5 |
| Rapid-digestible fraction (%) | 45.8 | 36 | 41.2 | 45.5 | 44.3 | 45.0 | 44.8 |
| Slow-digestible fraction (%) | 52.0 | 41.3 | 42.5 | 44.1 | 43.1 | 54.2 | 52.7 |

TABLE 23-continued

| | Comparative Example | | | |
|---|---|---|---|---|
| | 5-3 | 6-1 | 6-2 | 6-3 |
| Initial digestion rate coefficient k | 0.031 | 0.026 | 0.025 | 0.023 |
| Indigestible fraction (%) | 1.7 | 10.9 | 11.3 | 13.7 |
| Rapid-digestible fraction (%) | 45.5 | 39.5 | 37.9 | 36.4 |
| Slow-digestible fraction (%) | 52.8 | 49.6 | 50.7 | 49.8 |

Working Example 7

Changes in Blood Glucose Levels and Blood Insulin Levels after Ingestion (Test for Comparison Between Working Example 1-3 and Glucose)

The high molecular weight glucans of the working example 1-3 and glucose were used to perform a crossover open trial on 10 healthy subjects, which measured the subjects' blood glucose levels and blood insulin levels after oral ingestion.

The subjects fasted for 10 hours or more excluding water before the digestion test.

Figure 14:
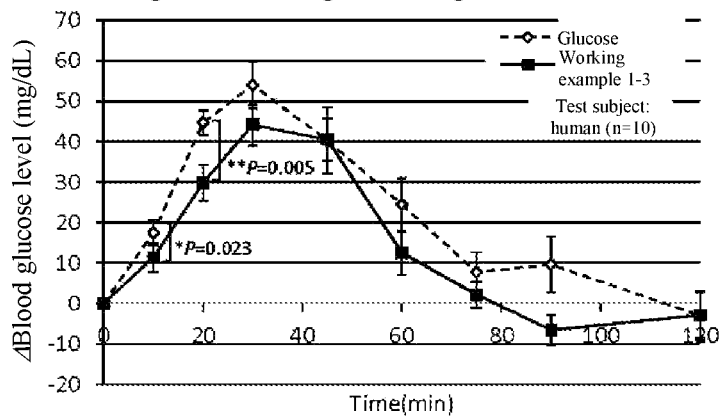
FIG. 14 presents graphs that illustrate time-dependent change and blood concentration—area under the curve (AUC) of blood glucose level/blood insulin level when glucose and the high molecular weight glucan of the working example 1-3 are orally ingested.
Figure 14:
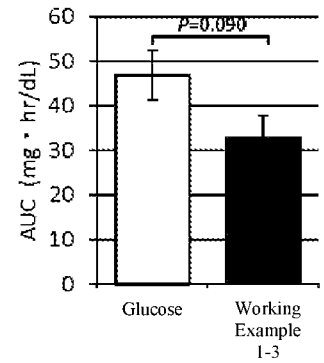
Figure 14:
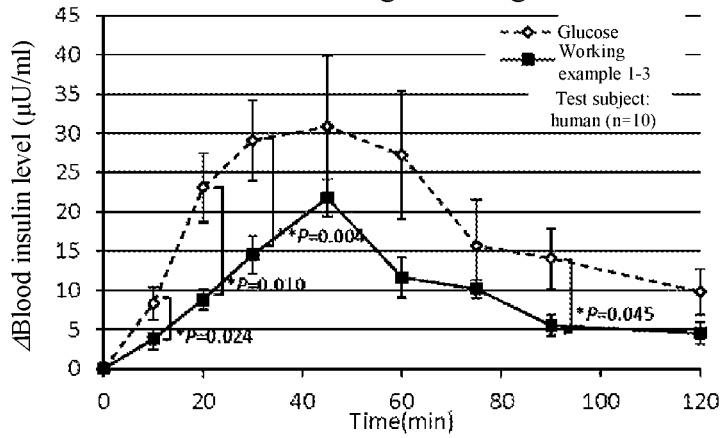
Figure 14:
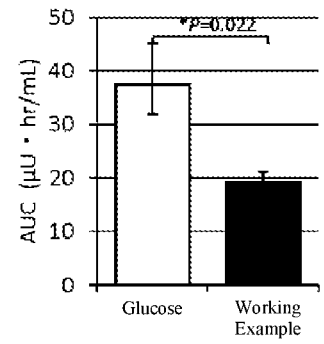

FIG. 14 shows a graph plotted with change values from fasting blood glucose and blood insulin levels before ingestion, and a graph calculated the area under the curve (AUC) of the blood glucose and blood insulin levels plotting charts.

According to this result, the high molecular weight glucans of the working example 1-3, as compared with glucose, exhibit significantly low values of rise in blood glucose level in 10 minutes and 20 minutes after ingestion, strongly indicating slow rise in blood glucose level in an early stage after intake. As for the AUC values of the blood glucose levels, no significant difference is found between glucose and the high molecular weight glucans of the working example 1-3, which suggests very efficient digestibility of the high molecular weight glucans of the working example 1-3 into glucose.

Also, the high molecular weight glucans of the working example 1-3, as compared with glucose, exhibit significantly low values of rise in blood insulin level in 10 minutes, 20 minutes, 30 minutes, and 90 minutes after ingestion, which strongly indicates slow insulin secretion after the ingestion. Further, the AUC value of blood insulin level after ingesting the high molecular weight glucans of the working example 1-3 exhibit significantly low as compared with the AUC of that after ingesting glucose. This result finds that the high molecular weight glucans are less likely to induce insulin secretion.

Thus, it was confirmed that the high molecular weight glucan characterized by a specific unit chain length distribution as defined in the present invention caused to be slow rise in the initial blood glucose levels and insulin secretion levels after ingestion.

Working Example 8

Changes in Blood Glucose Levels and Blood Insulin Levels after Ingestion (Test for Comparison Between Working Example 1-1 and Comparative Example 1-3)

The high molecular weight glucan of the working example 1-1 and the branched glucan of the comparative example 1-3 were used to perform a crossover open trial on one healthy subject, which measured the subject's blood glucose level and blood insulin level after oral ingestion. The subject fasted for 10 hours or more excluding water before the digestion test.

Figure 15:
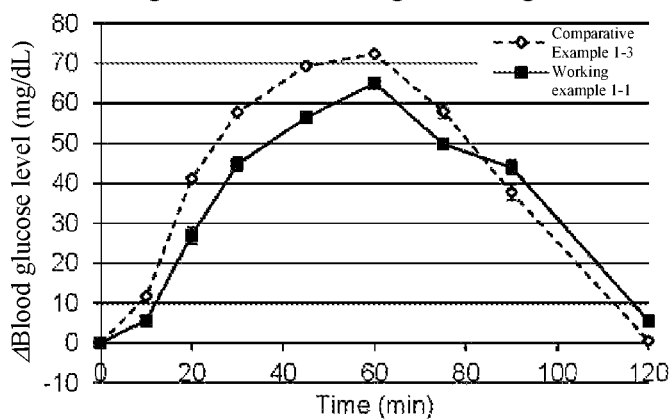
FIG. 15 presents graphs that illustrate time-dependent change and blood concentration—area under the curves (AUC) of blood glucose level/blood insulin level when the high molecular weight glucan of the working example 1-3 and the branched glucan of the comparative example 1-3 are orally ingested.
Figure 15:
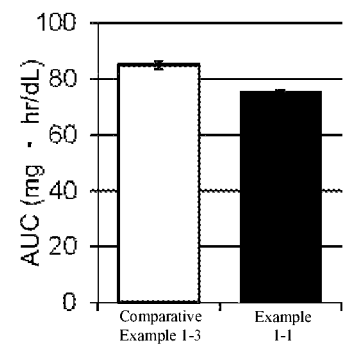
Figure 15:
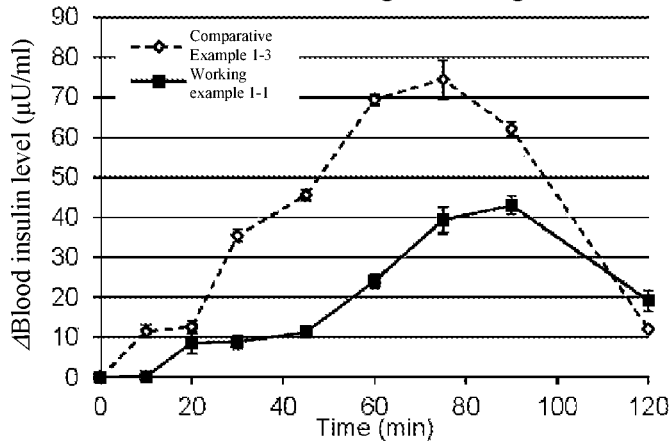
Figure 15:
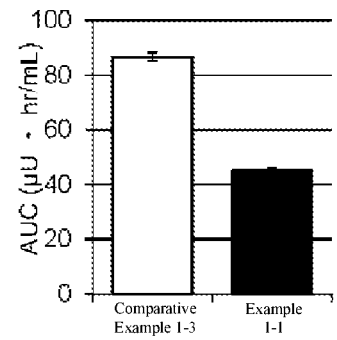

FIG. 15 shows a graph plotted with change values from fasting blood glucose and blood insulin levels before ingestion, and a graph calculated the area under the curve (AUC) of the blood glucose and blood insulin levels plotting charts.

According to this result, the high molecular weight glucan of the working example 1-1, as compared with the branched glucan of the comparative example 1-3, exhibits low values of blood glucose rise in an early stage up to 30 minutes after ingestion. This high molecular weight glucan is thus found to be slowly digested. Further, the high molecular weight glucan of the working example 1-1, as compared with the branched glucan of the comparative example 1-3, exhibits low values of blood insulin rise in an early stage up to 30 minutes after the ingestion. This high molecular weight glucan is thus found to be moderate in insulin secretion. On the other hand, AUC value of the blood glucose levels after ingesting the high molecular weight glucan of the working example 1-1 is approximately 90% of that of the branched glucan of the comparative example 1-3, and these polymer and branched glucans had comparable digestibility. The blood insulin AUC value of the high molecular weight glucan of the working example 1-1 is as low as approximately 50% of that of the branched glucan of the comparative example 1-3. This result finds that the high molecular weight glucan of the working example 1-1 is less likely to induce insulin secretion.

These results confirmed that the high molecular weight glucan characterized by a specific unit chain length distribution as defined by the present invention caused to be slow rise in the initial blood glucose levels and insulin secretion levels after ingestion.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A high molecular weight glucan having a structure in which a branched chain of α-1,6-glucoside bonds is linked to a main chain of α-1,4-glucoside bonds,
the high molecular weight glucan having an average molecular weight of 10,000 to 500,000,
wherein the following properties (i) to (iii) are fulfilled by HPAEC-PAD analysis of unit chain length distributions obtained after the α-1,6-glucoside bonds are hydrolyzed by isoamylase to a linear unit chain length,
(i) the ratio of the total value of the peak areas for degrees of polymerization of 1 to 5 to the total value of the peak areas for degrees of polymerization of 6 to 10 is 33% to 50%,
(ii) the ratio of the total value of the peak areas for degrees of polymerization of 11 to 15 to the total value of the peak areas for degrees of polymerization of 6 to 10 is 80% to 125%, and
(iii) the ratio of the total value of the peak areas for degrees of polymerization of 26 to 30 to the total value of the peak areas for degrees of polymerization of 6 to 10 is 16% to 43%.

2. The high molecular weight glucan according to claim 1, wherein at least one of the following properties (iv) to (vii) is further fulfilled by HPAEC-PAD analysis of unit chain length distributions,
(iv) the ratio of the total value of the peak areas for degrees of polymerization of 16 to 20 to the total value of the peak areas for degrees of polymerization of 6 to 10 is 53% to 85%,
(v) the ratio of the total value of the peak areas for degrees of polymerization of 21 to 25 to the total value of the peak areas for degrees of polymerization of 6 to 10 is 31% to 62%,
(vi) the ratio of the total value of the peak areas for degrees of polymerization of 31 to 35 to the total value of the peak areas for degrees of polymerization of 6 to 10 is 8% to 30%, and
(vii) the ratio of the total value of the peak areas for degrees of polymerization of 36 to 40 to the total value of the peak areas for degrees of polymerization of 6 to 10 is 3% to 21%.

3. The high molecular weight glucan according to claim 1, wherein an initial in vitro digestion rate coefficient, k, of an enzymatic hydrolysis reaction of the high molecular weight glucan by α-amylase and α-glucosidase enzymes is less than 0.029, and the ratio of indigestible components at 120 minutes after start of the enzymatic hydrolysis reaction is less than 10%,
wherein the enzymatic hydrolysis reaction is conducted at 37° C. in a mixture of: i) 100 μL of a 5 w/v % aqueous solution of the high molecular weight glucan; ii) 20 μL of a 1M acetic acid buffer at pH 5.5; iii) 716 μL of distilled water; iv) 4 μL of a porcine pancreatic a-amylase solution comprising 250 units/mL; and v) 160 μL of a rat small intestine acetone powder in a concentration equivalent to 0.3 units/mL of α-glucosidase activity, and
wherein k is calculated according to Formula 1:

$\ln(1-C_t)=-kt,$ wherein:
t is the hydrolysis reaction time in minutes;
$C_t$ is (amount of glucose produced in t minutes)/(total amount of glucose in the high molecular weight glucan); and
k is a slope of a primary regression line when time t is plotted versus $\ln(1-C_t)$ for the first 30 minutes of the enzymatic hydrolysis reaction.

4. The high molecular weight glucan according to claim 3, wherein a ratio of the high molecular weight glucan hydrolyzed within 20 minutes from the start of the enzymatic hydrolysis reaction is less than 45%, and a ratio of the high molecular weight glucan hydrolyzed from 20 minutes to 120 minutes after the start of the enzymatic hydrolysis reaction is greater than or equal to 50%.

5. The high molecular weight glucan according to claim 1, wherein a non-reducing end of the main chain of the α-1,4-glucoside bond does not have a branching structure formed by the α-1,6-glucoside bond.

6. A food or a drink, or both, comprising the high molecular weight glucan according to claim 1.

7. A method for controlling a rise in blood glucose level or in blood insulin level, or both, comprising administering the food or the drink according to claim 6 to a subject in need thereof.

8. An infusion comprising the high molecular weight glucan according to claim 1.

9. A pharmaceutical product comprising the high molecular weight glucan according to claim 1.

10. A method for producing the high molecular weight glucan according to claim 1, the method comprising:
making 100 to 4,000 U/g substrate of branching enzyme and 4-α-glucanotransferase react to a branched glucan used as substrate at the same time or stepwisely in any order; and
terminating the reactions at a point in time after the high molecular weight glucan is produced.

11. A method for producing the high molecular weight glucan according to claim 1, the method comprising:
making 100 to 4,000 U/g substrate of a branching enzyme react with a branched glucan which is used as substrate, and then making an exo-type amylase react with the branched glucan which is used as substrate; and
terminating the reactions at a point in time after the high molecular weight glucan is produced.

12. The method according to claim 10, wherein the 4-a-glucanotransferase is amylomaltase or cyclodextrin glucanotransferase, or both.

13. The method according to claim 11, wherein the exo-type amylase is β-amylase.

14. The method according to claim 10, wherein the branched glucan is waxy starch.

* * * * *